US012780827B2

(12) United States Patent
Yang et al.

(10) Patent No.: US 12,780,827 B2
(45) Date of Patent: Nov. 3, 2026

(54) PIM KINASE INHIBITOR

(71) Applicant: Hangzhou Biosun Pharmaceutical Co., Ltd., Zhejiang (CN)

(72) Inventors: Xin Yang, Zhejiang (CN); Rong Cui, Zhejiang (CN); Jianming Yin, Zhejiang (CN); Mei Zheng, Zhejiang (CN); Nanyu Chen, Zhejiang (CN); Yubin Lv, Zhejiang (CN)

(73) Assignee: Hangzhou Biosun Pharmaceutical Co., Ltd., Zhejiang (CN)

( * ) Notice: Subject to any disclaimer, the term of this patent is extended or adjusted under 35 U.S.C. 154(b) by 522 days.

(21) Appl. No.: 18/263,936

(22) PCT Filed: Jan. 29, 2022

(86) PCT No.: PCT/CN2022/074876

§ 371 (c)(1),
(2) Date: Aug. 2, 2023

(87) PCT Pub. No.: WO2022/166860

PCT Pub. Date: Aug. 11, 2022

(65) Prior Publication Data

US 2024/0124469 A1 Apr. 18, 2024

(30) Foreign Application Priority Data

Feb. 8, 2021 (CN) ........................ 202110172000.X
Nov. 19, 2021 (CN) ........................ 202111376097.2
Jan. 11, 2022 (CN) ........................ 202210025780.X

(51) Int. Cl.
*C07D 487/04* (2006.01)
*C07D 471/04* (2006.01)
*C07D 519/00* (2006.01)

(52) U.S. Cl.
CPC ......... *C07D 487/04* (2013.01); *C07D 471/04* (2013.01); *C07D 519/00* (2013.01)

(58) Field of Classification Search
CPC ... C07D 487/04; C07D 471/04; C07D 519/00
See application file for complete search history.

(56) References Cited

U.S. PATENT DOCUMENTS

2007/0093490 A1 4/2007 Prien et al.
2011/0021513 A1 1/2011 Durand-Reville et al.
2012/0058997 A1 3/2012 Xu et al.

FOREIGN PATENT DOCUMENTS

CA 2620534 C * 5/2014 ............. A61P 43/00
CN 101594909 A 12/2009
CN 101600718 A 12/2009
WO 2007025540 A2 3/2007
WO 2013013188 A1 1/2013
WO WO-2016161248 A1 * 10/2016 ......... A61K 31/5025

OTHER PUBLICATIONS

Brown; Bioisosteres in Medicinal Chemistry, Wiley-VCH, 2012 (Year: 2012).*
Brown, N.; Bioisosteres in Medicinal Chemistry, Wiley-VCH, 2012 (Year: 2012).*
Pastor, et al.; Bioorganic & Medicinal Chemistry Letters; v22, pp. 1591-1597; 2012 (Year: 2012).*
Asati et al., PIM kinase inhibitors; Structural and pharmacological perspectives; European Journal of Medicinal Chemistry, Accepted Manuscript; Mar. 19, 2019; pp. 1-73.
Bullock et all., Structural Basis of Inhibitor Specificity of the Human Protooncogene Proviral Insertion Site in Molongey Murine Leukemia Virus (PIM-1) Kinase; J. Med. Chem, 2005, vol. 48, pp. 7604-7614.
Bouloc et al., Synthesis and in vitro evaluation of imidazopyridazines as novel inhibitors of the malarial kinase PfPK7; Bioorganic & Medicinal Chemistry Letters; 2008, vol. 18, pp. 5294-5298.
Chapman et al., Substituted imidazopyridazines are potent and selective inhibitors of Plasmodium falciparum calcium-dependent protein kinase 1 (PFCDPK1); Bioorganic & Medicinal Chemistry Letters, 2023, pp. 3064-3069.
Doudou et al., Inhibitors of PIM-1 Kinase: A Computational Analysis of the Binding Free Energies of a Range of Imidazo [1,2-b] Pyridazines; J. Chem Inf. Model; 2010, vol. 50, pp. 368-379.
Jeyapal et al., Potential Pharmacological Inhibitors of Pim Kinase Under Clinical Trials; Anti-Cancer Agents in Medicinal Chemistry; 2018, vol. 18, pp. 1100-1114.
Large et al., Imidazopyridazines as potent inhibitors of Plasmodium falciparum calcium-dependent protein kinase 1 (PfCDPK1): Preparation and evaluation of pyrazole linked analogues; Bioorganic & Medicinal Chemistry Letters, 2013, vol. 23, pp. 6019-6024.

(Continued)

*Primary Examiner* — Jeffrey S Lundgren
*Assistant Examiner* — W. Justin Youngblood
(74) *Attorney, Agent, or Firm* — Tracey S. Truitt; Sandberg Phoenix & von Gontard, PC

(57) ABSTRACT

A compound having a structure as shown in general formula (I), a deuterated compound, a stereoisomer, or a pharmaceutically acceptable salt thereof, a pharmaceutical composition comprising same, and use thereof. The compound has a good PIM kinase inhibitory effect, is a novel and ideal PIM inhibitor having high activity and low toxicity, and can be used for treating and/or preventing hematoma such as acute myeloid leukemia, bone marrow fibrosis and chronic lymphocytic leukemia, solid tumors such as gastric cancer and prostate cancer, and other diseases.

(I)

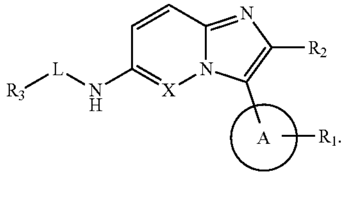

21 Claims, No Drawings

(56) References Cited

OTHER PUBLICATIONS

Pogacic et al., Structural Analysis Idenifies Imidazo{1,2-b]Pyridazines as PIM Kinase Inhibitors with In vitro Antileukemic Activity; Cancer Research, Jul. 15, 2007, vol. 67, No. 14, pp. 6916-6924.
Sahu et al., QSAR studies on imidazopyridazine derivatives a PfPK7 inhibitors; Molecular Simulation; Aug. 2011, vol. 37, No. 9, pp. 752-765.
Shimizu et al., Discovery of imidazo[1,2-b]pyridazines as IKKB inhibitors. Part 3: Exploration of effective compounds in arthritis models. Bioorganic & Medicinal Chemistry Letters; 2011, vol. 21, pp. 4550-4555.
Pastor et al., Hit to lead evaluation of 1,2,3,-triazolo[4,5b]pyridines as PIM kinase inhibitors; Bioorganic & Medicinal Chemistry Letters, 2012, vol. 22, pp. 1591-1597.
Registry 1, RN 2650928-82-9 Registry.
Registry 2, RN 1033244-93-7 Registry.

* cited by examiner

PIM KINASE INHIBITOR

CROSS-REFERENCE TO RELATED APPLICATION(S)

This application is a national phase application of International Patent Application No. PCT/CN2022/074876 (published as WO 2022/166860), filed Jan. 29, 2022, which claims priority to CN Application Serial No. 202110172000.X, filed Feb. 8, 2021, CN application Serial No. 202111376097.2, filed Nov. 19, 2021, and CN application Serial No. 202210025780.X, filed Jan. 11, 2022, all of which are hereby incorporated by reference in their entireties.

TECHNICAL FIELD

The present invention belongs to the field of medicinal chemistry, and relates to a PIM kinase inhibitor, a pharmaceutical composition thereof, a preparation method therefor, and use thereof in the preparation of a medicament for preventing and/or treating an indication related to a PIM signaling pathway.

BACKGROUND

The proviral integration site of Moloney murine leukemia virus (PIM) kinase is a serine/threonine protein kinase, and consists of three subtypes, PIM1, PIM2, and PIM3. PIM1 and PIM2 are highly expressed in hematological and solid tumors, and PIM3 is highly express in hepatocellular carcinoma, pancreatic cancer, and colon cancer.

The PIM kinase is a downstream molecule of the JAK/STAT pathway, and the JAK pathway plays an important role in autoimmune diseases. It has been shown in the literature that the PIM-1 inhibitor is effective in a mouse model of inflammatory bowel disease. This suggests the application of the PIM kinase inhibitor in autoimmune diseases.

In addition, the PIM kinase can regulate cell proliferation, growth, and invasiveness by phosphorylating a series of downstream signal molecules such as p53, BAD, and MYC, and plays an important role in the occurrence and development of tumors. It has been found in pre-clinical researches that the PIM inhibitor has therapeutic effects on both the hematological tumor such as acute myeloid leukemia, myelofibrosis, and chronic lymphocytic leukemia, and the solid tumor such as gastric cancer and prostate cancer. This suggests the role of the PIM inhibitor in the treatment of tumors.

Sumitomo Dainippon Pharma has developed a PIM inhibitor TP-3654 (WO2013013188), which, however, has low cell inhibitory activity, high toxicity, and low bioavailability. Therefore, there is an urgent need to provide a more effective PIM inhibitor.

SUMMARY

In the view of the above technical problems, a first aspect of the present invention provides a compound having a structure represented by general formula (I), or a deuteride, a stereoisomer, or a pharmaceutically acceptable salt thereof:

(I)

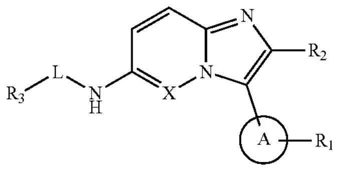

wherein:

- ring A is 5- to 6-membered heterocyclyl, 5- to 6-membered aryl, or 5-to 6-membered heteroaryl, the 5- to 6-membered heterocyclyl or 5- to 6-membered heteroaryl comprising at least 1 heteroatom selected from N, O, and S;
- X is CH or N;
- L is a chemical bond or methylene;
- $R_1$ is selected from hydrogen, halogen, hydroxyl, carboxyl, cyano $-NH_2$, $-C_1$-$C_3$ alkyl, $-O(C$-$C_6$ alkyl) halogen-substituted $-C_1$-$C_3$ alkyl, halogen-substituted $-O(C_1$-$C_3$ alkyl), and $-NH(C_1$-$C_6$ alkyl), $-N(C_1$-$C_6$ alkyl$)_2$, methanesulfonyl, and 5- to 6-membered heteroaryl; when $R_1$ is 5- to 6-membered heteroaryl, the group is optionally substituted with 0-3 $R^b$;
- $R_2$ is selected from hydrogen, halogen, hydroxyl, carboxyl, cyano, $-NH_2$, $-C_1$-$C_6$ alkyl, $-O(C_1$-$C_6$ alkyl), $-NH(C_1$-$C_6$ alkyl), trifluoromethyl, trifluoromethyloxy, and $-COOR^c$;
- $R_3$ is selected from 3- to 10-membered saturated or unsaturated hydrocarbyl (including linear or branched alkyl or heteroalkyl), monocyclic or bicyclic cycloalkyl or heterocyclyl, and monocyclic or bicyclic aryl or heteroaryl, the heteroalkyl, heterocyclyl, or heteroaryl comprising at least 1 heteroatom selected from N, O, and S;
- $R_3$ is optionally substituted with 1-3 $R^a$;
- $R^a$ is selected from hydrogen, halogen, hydroxyl, carboxyl, cyano, $-NH_2$, $-C_1$-$C_6$ alkyl, $-C_3$-$C_6$ cycloalkyl, $-O(C_1$-$C_6$ alkyl), $-NH(C_1$-$C_6$ alkyl), trifluoromethyl, trifluoromethyloxy, and $-O(C_1$-$C_6$ alkylene)-OH;
- $R^b$ and $R^c$ are each independently selected from halogen and $-C_1$-$C_3$ alkyl.

In certain embodiments according to the present invention, the compound having the structure represented by general formula (I), or the deuteride, the stereoisomer, or the pharmaceutically acceptable salt thereof provided by the present invention may further be as follows:

- ring A is 5- to 6-membered aryl or 5- to 6-membered heteroaryl, the 5- to 6-membered heteroaryl comprising at least 1 heteroatom selected from N, O, and S;
- X is CH or N;
- L is a chemical bond or methylene;
- $R_1$ is selected from hydrogen, halogen, hydroxyl, cyano, $-NH_2$, $-C_1$-$C_6$ alkyl, $-O(C_1$-$C_6$ alkyl), $-NH(C_1$-$C_6$ alkyl), trifluoromethyl, and trifluoromethyloxy;
- $R_2$ is selected from hydrogen, halogen, hydroxyl, carboxyl, cyano, $-NH_2$, $-C_1$-$C_6$ alkyl, $-O(C_1$-$C_6$ alkyl), $-NH(C_1$-$C_6$ alkyl), trifluoromethyl, and trifluoromethyloxy;
- $R_3$ is selected from linear or branched alkyl or heteroalkyl, monocyclic or bicyclic cycloalkyl or heterocyclyl, and monocyclic or bicyclic aryl or heteroaryl, the heteroalkyl, heterocyclyl, or heteroaryl comprising at least 1 heteroatom selected from N, O, and S;
- $R_3$ is optionally substituted with 1-3 $R^a$;

$R^a$ is selected from hydrogen, halogen, hydroxyl, carboxyl, cyano, —$NH_2$, —$C_1$-$C_6$ alkyl, —O($C_1$-$C_6$ alkyl), —NH($C_1$-$C_6$ alkyl), trifluoromethyl, trifluoromethyloxy, and —($C_1$-$C_6$ alkylene)—OH.

In certain embodiments according to the present invention, the compound having the structure represented by general formula (I), or the deuteride, the stereoisomer, or the pharmaceutically acceptable salt thereof provided by the present invention may further be as follows:

ring A is phenyl or 5- to 6-membered heteroaryl, the 5- to 6-membered heteroaryl comprising 1 heteroatom selected from N, O, and S;

X is a N atom;

L is a chemical bond or methylene;

$R_1$ is selected from hydrogen, trifluoromethyl, and trifluoromethyloxy;

$R_2$ is selected from hydrogen;

$R_3$ is selected from 3- to 10-membered monocyclic or bicyclic cycloalkyl or heterocyclyl, the heterocyclyl comprising at least 1 heteroatom selected from N, O, and S;

$R_3$ is optionally substituted with 1-3 $R^a$;

$R^a$ is selected from hydrogen, halogen, hydroxyl, carboxyl, cyano, —$NH_2$, —$C_1$-$C_6$ alkyl, —O($C_1$-$C_6$ alkyl), —NH($C_1$-$C_6$ alkyl), trifluoromethyl, trifluoromethyloxy, and —($C_1$-$C_6$ alkylene)—OH.

In certain embodiments according to the present invention, the compound provided by the present invention further has a structure represented by general formula (II):

(II)

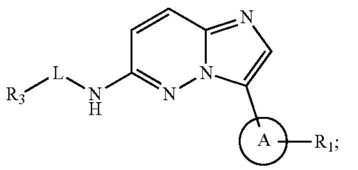

wherein:

ring A is a phenyl ring or 5-membered heteroaryl, the 5-membered heteroaryl optionally comprising 1-2 heteroatoms selected from N, O, and S;

L is a chemical bond or methylene;

$R_1$ is selected from hydrogen, halogen, hydroxyl, cyano, carboxyl, —$NH_2$, —$C_1$-$C_3$ alkyl, —$C_1$-$C_3$ alkoxy, halogen-substituted —$C_1$-$C_3$ alkyl, halogen-substituted —$C_1$-$C_3$ alkoxy, and 5-membered heteroaryl comprising 1 heteroatom selected from N, O, and S;

$R_3$ is selected from 6- to 7-membered monocyclic cycloalkyl or heterocyclyl, the heterocyclyl optionally comprising 0-1 heteroatoms selected from N, O, and S; or $R_3$ is selected from 8- to 9-membered bicyclic cycloalkyl or heterocyclyl, the heterocyclyl optionally comprising 0-1 heteroatoms selected from N, O, and S, and the bicyclic ring being a spiro ring or a bridged ring;

$R_3$ is optionally substituted with one $R^a$;

$R^a$ is selected from hydrogen, halogen, hydroxyl, carboxyl, —$C_1$-$C_6$ alkyl, —$C_3$-$C_8$ cycloalkyl, and —($C_1$-$C_6$ alkylene)—OH.

In certain embodiments according to the present invention, the compound having the structure represented by general formula (II), or the deuteride, the stereoisomer, or the pharmaceutically acceptable salt thereof provided by the present invention may further be as follows:

ring A is selected from phenyl, thienyl, and thiazolyl; ring A is substituted with $R_1$;

$R_1$ is selected from hydrogen, —$C_1$-$C_3$ alkyl substituted with 1-3 halogens, and 5-membered heteroaryl comprising 1 heteroatom selected from N, O, and S.

In some preferred embodiments, ring A is selected from

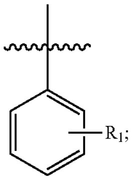

L is a chemical bond or methylene;

$R_1$ is selected from hydrogen, trifluoromethyl, and

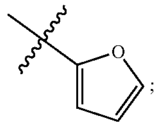 [SMILES: *c1ccco1]

$R_3$ is selected from

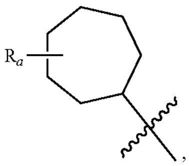
,
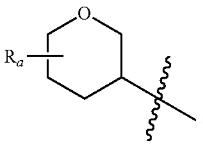
, and
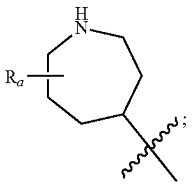

or $R_3$ is selected from 8- to 9-membered bicyclic cycloalkyl or heterocyclyl, the heterocyclyl optionally comprising 1 heteroatom selected from N, O, and S, and the bicyclic ring being a spiro or bridged ring; the $R_3$ is optionally substituted with one $R^a$;

the $R^a$ is selected from hydrogen, hydroxyl, —$C_1$-$C_3$ alkyl, —$C_3$-$C_6$ cycloalkyl, and —($C_1$-$C_6$ alkylene)—OH.

In some more preferred embodiments, $R_3$ is selected from

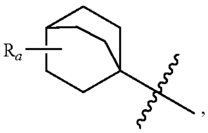
,
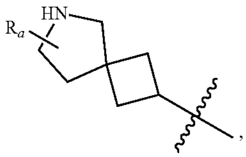
, and

-continued

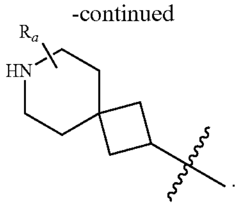

In some more preferred embodiments, the $R^a$ is selected from hydrogen, hydroxyl, methyl, cyclopropyl, -methylenehydroxyl, and —$C(CH_3)_2$—OH.

In certain embodiments according to the present invention, the compound having the structure represented by general formula (II), or the deuteride, the stereoisomer, or the pharmaceutically acceptable salt thereof provided by the present invention may further be as follows:

ring A is selected from

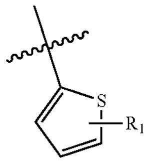

and

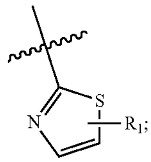

L is a chemical bond;

$R_1$ is selected from hydrogen and trifluoromethyl;

$R_3$ is selected from

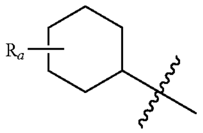

,

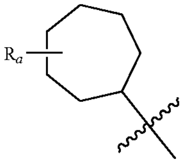

,

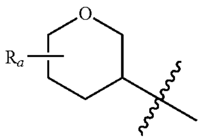

, and

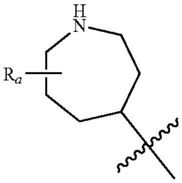

;

or $R_3$ is selected from 8- to 9-membered bicyclic cycloalkyl or heterocyclyl, the heterocyclyl optionally comprising 1 heteroatom selected from N, O, and S, and the bicyclic ring being a spiro or bridged ring; the $R_3$ is optionally substituted with one $R^a$;

$R^a$ is selected from hydrogen, hydroxyl, —$C_1$-$C_3$ alkyl, —$C_3$-$C_6$ cycloalkyl, and —($C_1$-$C_6$ alkylene)—OH.

In some preferred embodiments, $R_3$ is selected from

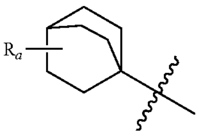

and

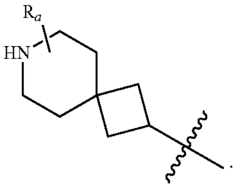

.

In some preferred embodiments, $R^a$ is selected from hydrogen, hydroxyl, methyl, cyclopropyl, -methylenehydroxyl, and —$C(CH_3)_2$—OH.

In some more preferred embodiments, $R_3$ is selected from

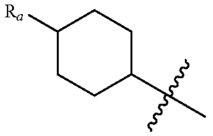

,

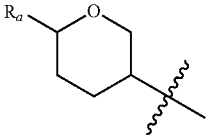

,

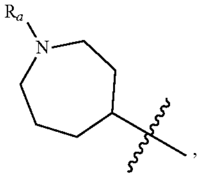

,

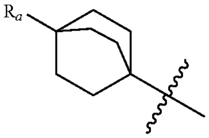

, and

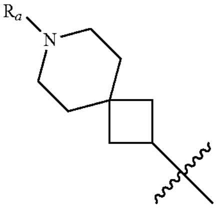

;

$R^a$ is selected from hydrogen, hydroxyl, methyl, -methylenehydroxyl, and —$C(CH_3)_2$—OH.

In certain embodiments according to the present invention, the compound provided by the present invention further has a structure represented by general formula (III-1) or (III-2):

(III-1)

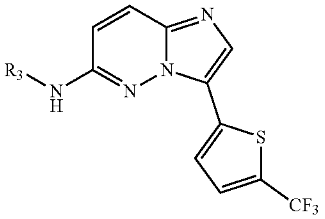

(III-2)

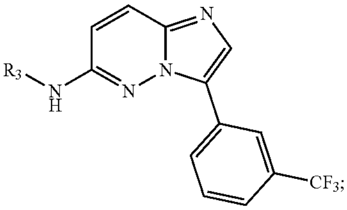

;

wherein $R_3$ is selected from

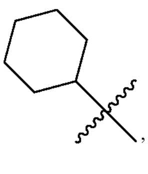

,

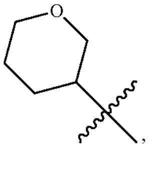

,

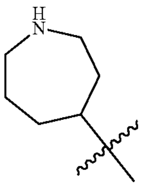

,

-continued

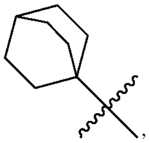, and 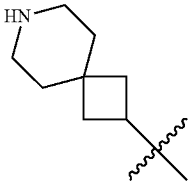, and $R_3$ is optionally substituted with one $R^a$ at a substitution site of C or N;

$R^a$ is selected from hydrogen, hydroxyl, -methylenehydroxyl, and —$C(CH_3)_2$—OH.

In some preferred embodiments, the $R_3$ is selected from:

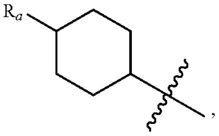, 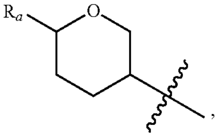, 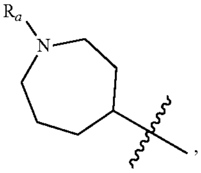, 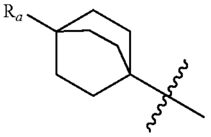, and 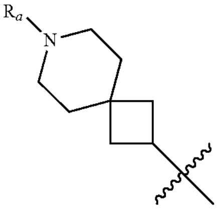.

In some more preferred embodiments, $R_3$ is selected from:

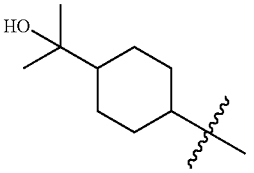, 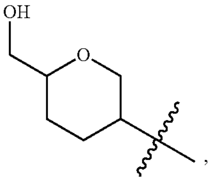, 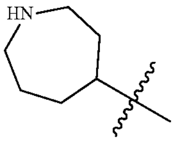, 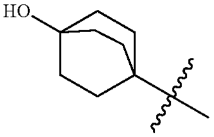, and 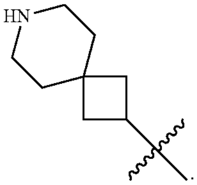.

In some more preferred embodiments, $R_3$ is selected from:

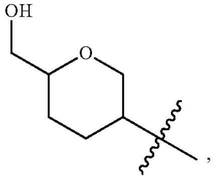, 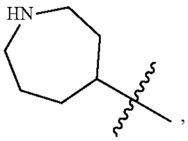, 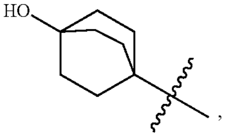, and 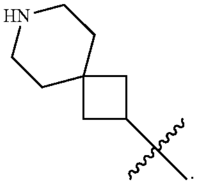.

In certain embodiments according to the present invention, the compound provided by the present invention further has the structure represented by general formula (III-1):

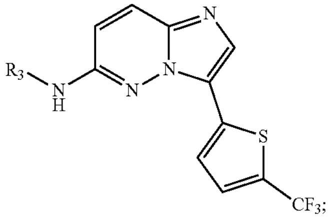

(III-1)

wherein $R_3$ is selected from

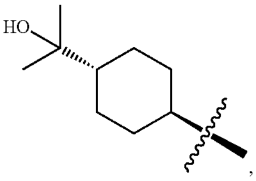, 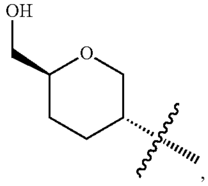, 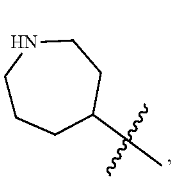, 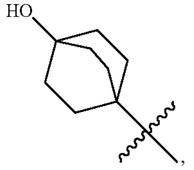, and 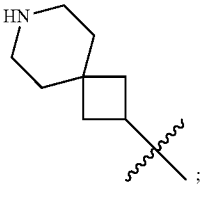;

In certain embodiments according to the present invention, the compound provided by the present invention further has the structure represented by general formula (III-2):

(III-2)

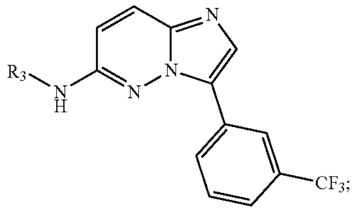

wherein $R_3$ is selected from

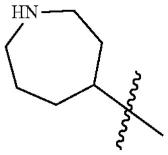

and

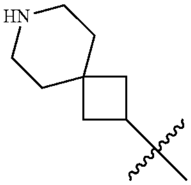

.

In certain embodiments according to the present invention, the compound provided by the present invention further has a structure represented by general formula (IV-1) or (IV-2):

(IV-1)

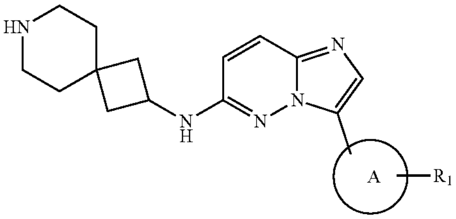

(IV-2)

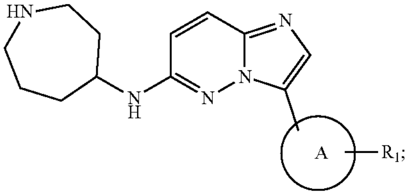

wherein:

ring A is selected from

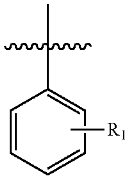

and

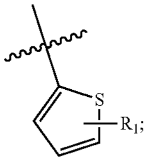

$R_1$ is selected from hydrogen and trifluoromethyl.

In some preferred embodiments, ring A is selected from:

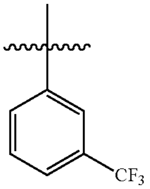

and

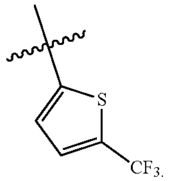

In certain embodiments according to the present invention, the compound having the structure represented by general formula (II) provided by the present invention may also be summarized as follows:

(II)

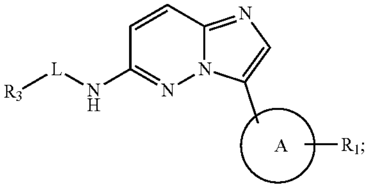

wherein:

ring A is phenyl or 5-membered heteroaryl, the 5-membered heteroaryl comprising 1 or 2 heteroatoms optionally selected from N, O, and S; ring A is substituted with $R_1$;

L is a chemical bond or methylene;

$R_1$ is selected from hydrogen, halogen, hydroxyl, cyano, —$NH_2$, —$C_1$-$C_6$ alkyl, —O($C_1$-$C_6$ alkyl), —NH($C_1$-$C_6$ alkyl), —N($C_1$-$C_6$ alkyl)$_2$, trifluoromethyl, and trifluoromethyloxy;

$R_3$ is selected from 3- to 10-membered monocyclic or bicyclic cycloalkyl or heterocyclyl, the heterocyclyl comprising 1 or 2 heteroatoms selected from N, O, and S;

$R_3$ is optionally substituted with 1-3 $R^a$;

$R^a$ is selected from hydrogen, halogen, hydroxyl, carboxyl, cyano, —$NH_2$, —$C_1$-$C_6$ alkyl, —O($C_1$-$C_6$ alkyl), —NH($C_1$-$C_6$ alkyl), trifluoromethyl, trifluoromethyloxy, and —($C_1$-$C_6$ alkylene)—OH. In some preferred embodiments, the compound having the structure represented by formula (II) may further be as follows:

ring A is selected from phenyl, furyl, thienyl, pyrrolyl, thiazolyl, and pyrazolyl; ring A is substituted with $R_1$;

L is a chemical bond or methylene;

$R_1$ is selected from hydrogen, halogen, hydroxyl, cyano, —$NH_2$, —$C_1$-$C_6$ alkyl, —O($C_1$-$C_6$ alkyl), —NH($C_1$-$C_6$ alkyl), —N($C_1$-$C_6$ alkyl)$_2$, trifluoromethyl, and trifluoromethyloxy;

$R_3$ is selected from 6- to 10-membered monocyclic or bicyclic cycloalkyl or heterocyclyl, the heterocyclyl comprising 1 heteroatom optionally selected from N, O, and S; $R_3$ is optionally substituted with 1-3 $R^a$;

$R^a$ is selected from hydrogen, halogen, hydroxyl, cyano, —$NH_2$, $C_1$-$C_6$ alkyl, —O($C_1$-$C_6$ alkyl), —NH($C_1$-$C_6$ alkyl), and —($C_1$-$C_6$ alkylene)—OH.

In some more preferred embodiments, the compound having the structure represented by general formula (II) may further be as follows:

ring A is selected from

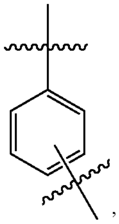 , 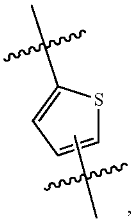 , 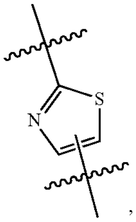 , and 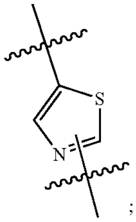 ;

ring A is substituted with $R_1$;

L is a chemical bond or methylene;

$R_1$ is selected from hydrogen and trifluoromethyl;

$R_3$ is selected from

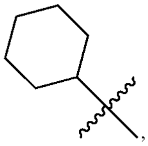 , 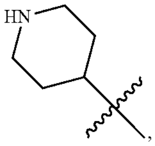 , 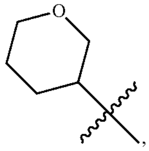 , 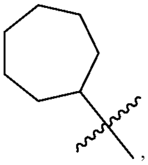 , 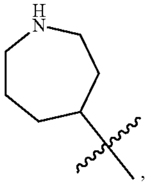 , 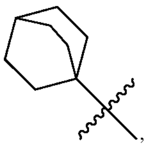 , 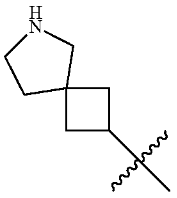 , and 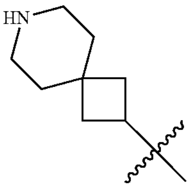 ;

$R_3$ is optionally substituted with 1-3 $R^a$ at a substitution site of C or N;

$R^a$ is selected from hydrogen, hydroxyl, carboxyl, $C_1$-$C_6$ alkyl, and —($C_1$-$C_6$ alkylene)—OH.

In some more preferred embodiments, the compound having the structure represented by general formula (II) may further preferably be as follows:

ring A is selected from

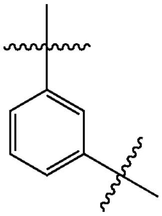 and 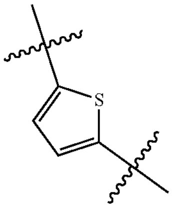 ;

ring A is substituted with $R_1$;

L is a chemical bond or methylene;

$R_1$ is selected from hydrogen and trifluoromethyl;

$R_3$ is selected from

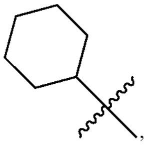 , 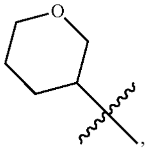 , 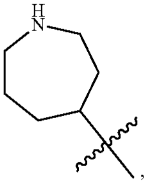 , 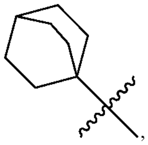 , 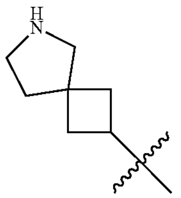 , and 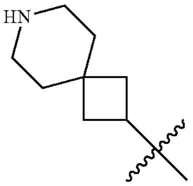 ;

$R_3$ is optionally substituted with 1-2 $R^a$ at a substitution site of C or N;

$R^a$ is selected from hydrogen, hydroxyl, carboxyl, —$C_1$-$C_3$ alkyl, and —($C_1$-$C_3$ alkylene)—OH; other variables are as defined in the present invention.

In some more specific embodiments, when the $R_3$ group comprises a heteroatom N, the substitution site is preferably at the N position. When the $R_3$ group does not comprise a heteroatom or the heteroatom is O, the substitution site is preferably at the meta-position or para-position of the connection site of the $R_3$ group to the L. When the $R_3$ group is of a bridged ring structure, the substitution site is typically at the bridgehead carbon at the other end of the connection site to the L.

In some more specific embodiments, $R^a$ group may be hydrogen, which may also be considered unsubstituted.

In some more specific embodiments, when the $R^a$ group is not hydrogen, it may be hydroxyl, carboxyl, —$C_1$-$C_3$ alkyl, or —($C_1$-$C_3$ alkylene)—OH. Unless otherwise stated, the —$C_1$-$C_3$ alkyl may be methyl, ethyl, n-propyl, isopropyl, or cyclopropyl. Unless otherwise stated, —($C_1$-$C_3$ alkylene)—OH is methylenehydroxyl, ethylenehydroxyl,

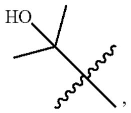, or 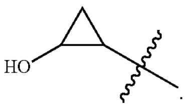.

As a preferred embodiment, ring A is phenyl, pyridinyl, tetrahydropyranyl, or pyrazolyl;

L is a chemical bond or methylene;

$R_1$ is selected from hydrogen, trifluoromethyl, and trifluoromethyloxy;

$R_2$ is selected from hydrogen, methyl, halogen, carboxyl, and cyano;

$R_3$ is selected from monocyclic or bicyclic cycloalkyl or heterocyclyl, and monocyclic or bicyclic aryl or heteroaryl, the heterocyclyl or heteroaryl comprising at least 1 heteroatom selected from N, O, and S; the $R_3$ is optionally substituted with 1-3 $R^a$;

$R^a$ is selected from methyl, isopropyl, carboxyl, and 2-hydroxyisopropyl

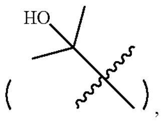,

As a preferred embodiment, ring A is selected from

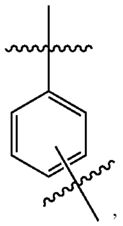, 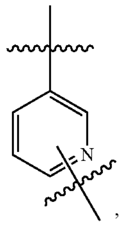, 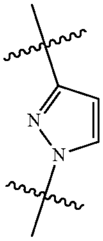, and 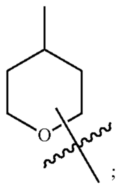;

$R_3$ is selected from

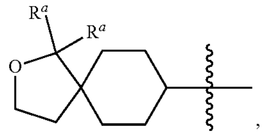, 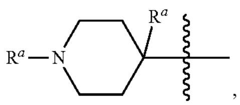, 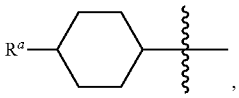, and 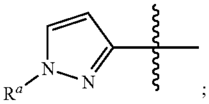;

$R^a$ is selected from methyl, isopropyl, carboxyl, and 2-hydroxyisopropyl.

As a preferred embodiment, $R_3$ is selected from

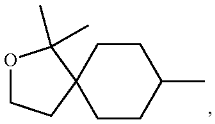, 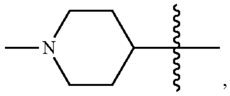, 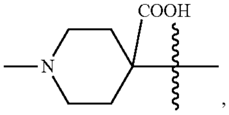, 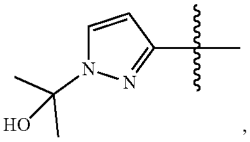, 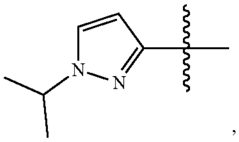, and 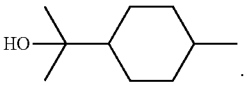.

In certain embodiments according to the present invention, the compound provided by the present invention comprises any one of the following structures:

1

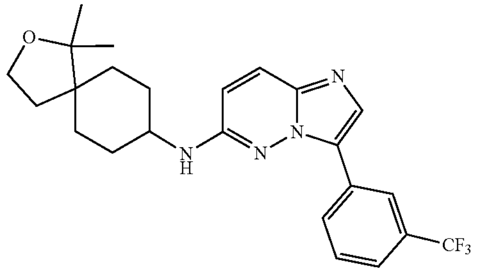

2

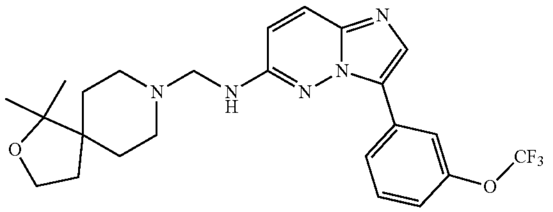

3

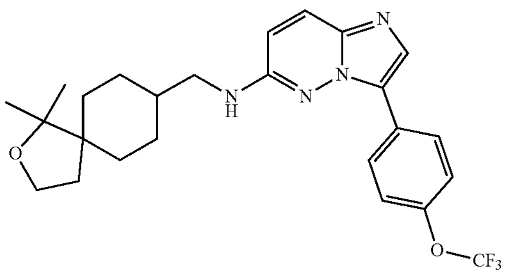

-continued
4
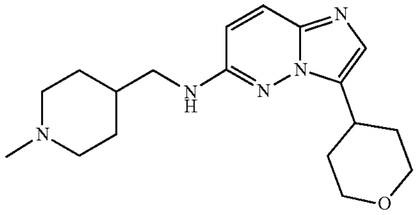
5
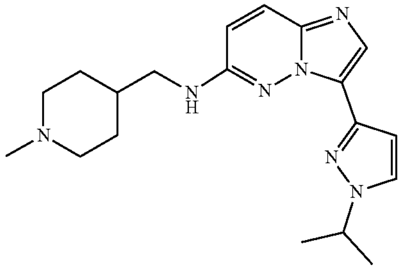
6
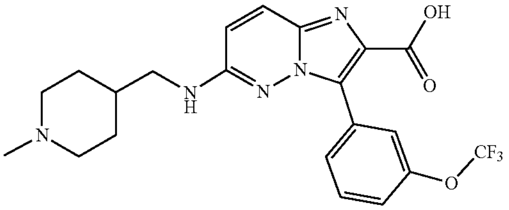
7
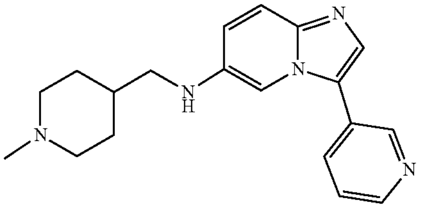
8
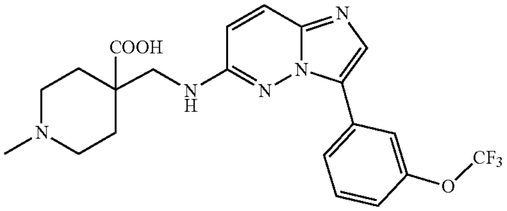
9
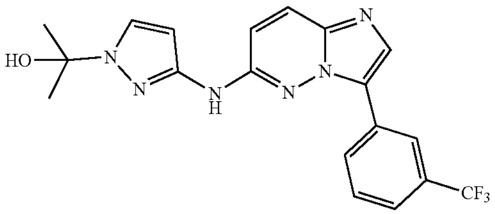
10
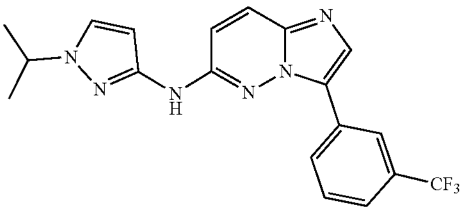
-continued
11
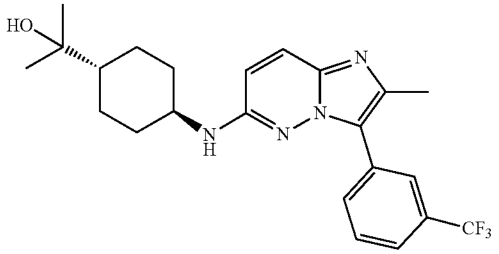
12
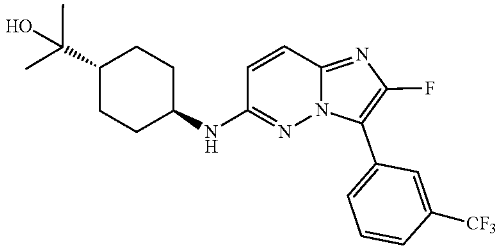
14
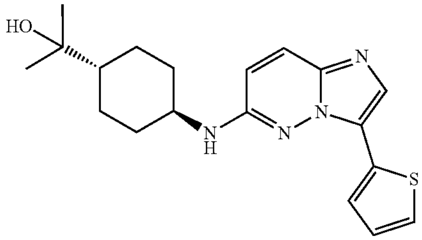
15
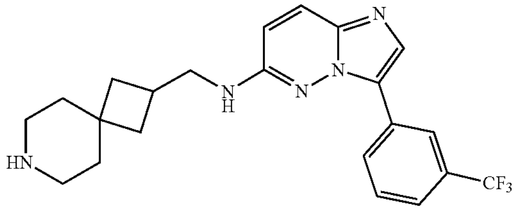
16
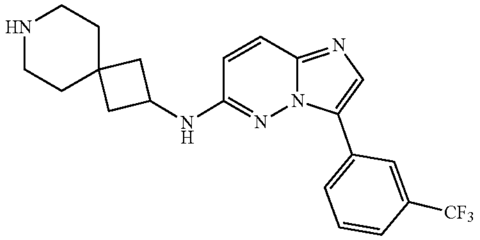
17
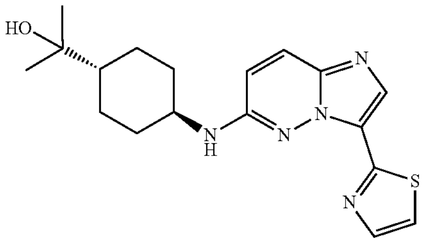

-continued
18
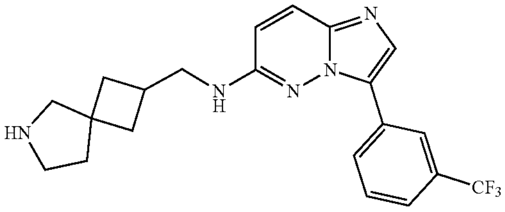
19
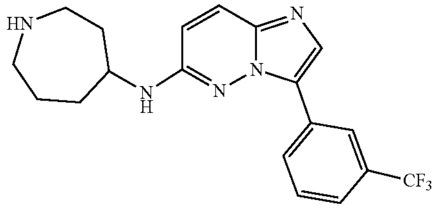
20
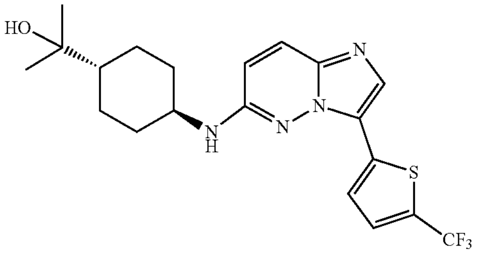
21
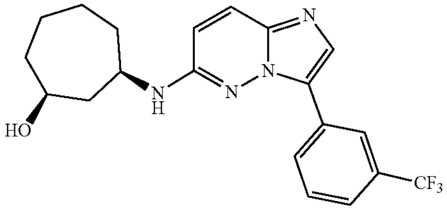
22
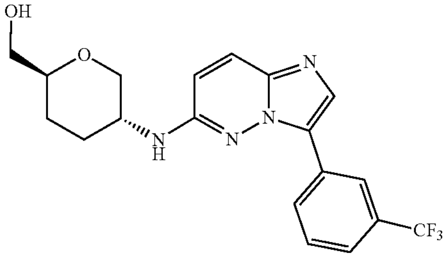
23
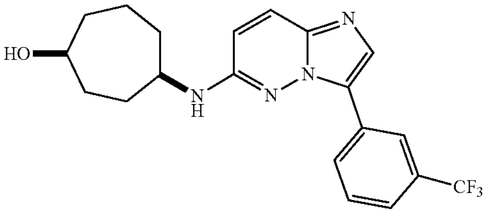
24
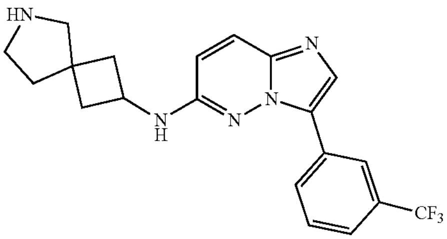
-continued
25
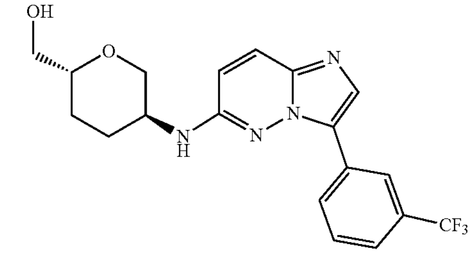
26
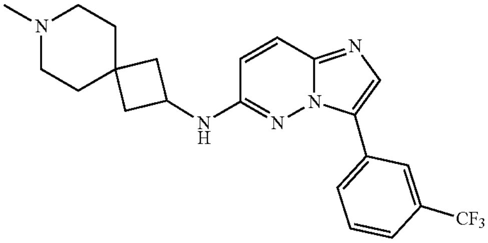
27
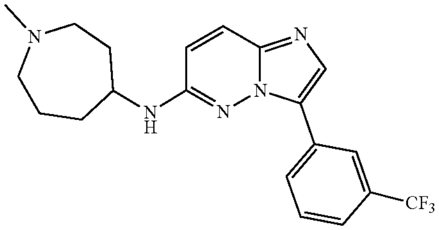
28
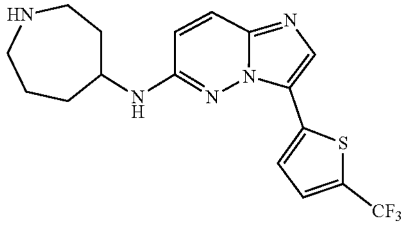
29
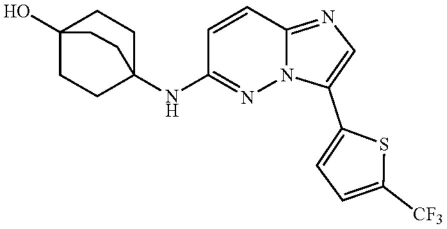
30
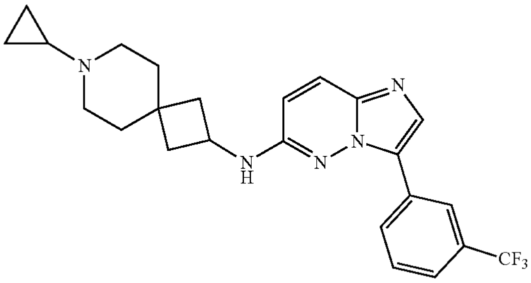

-continued
31
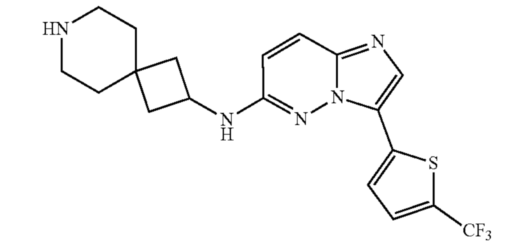
32
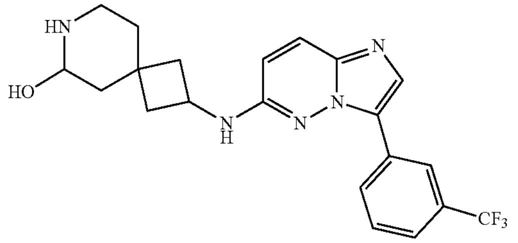
33
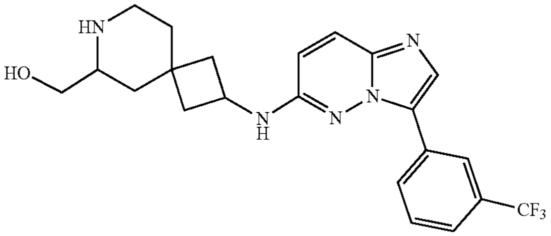
35
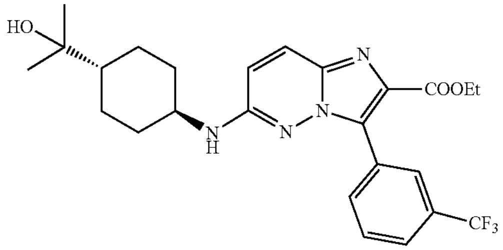
36
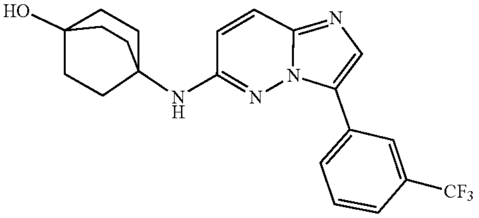
41
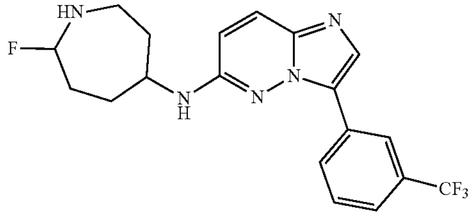
-continued
42
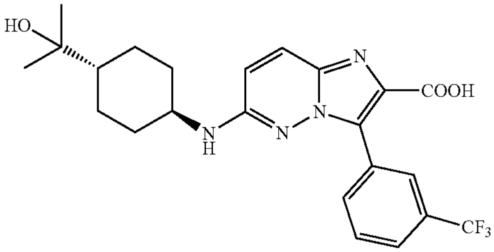
43
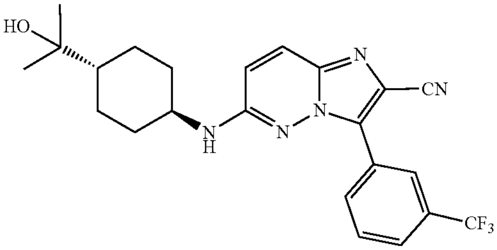
44
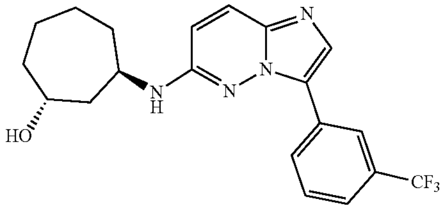
45
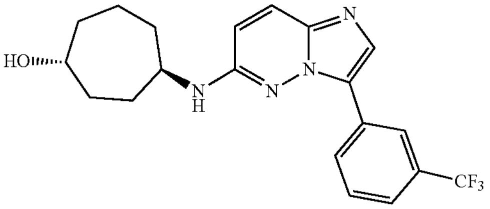
46
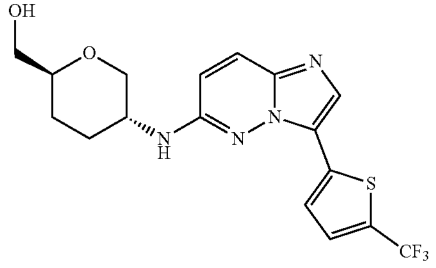
47
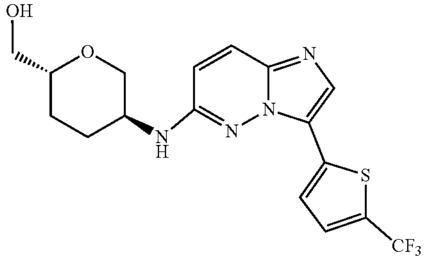

-continued

48

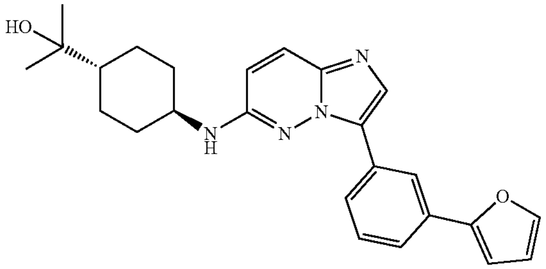

49

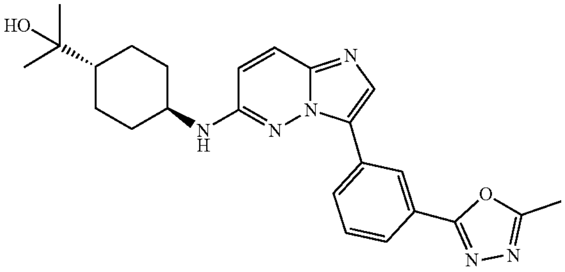

50

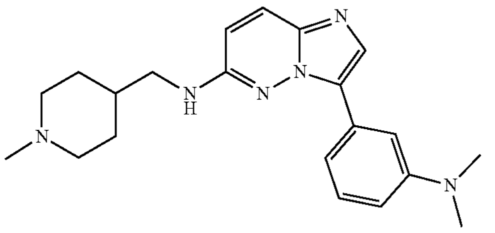

51

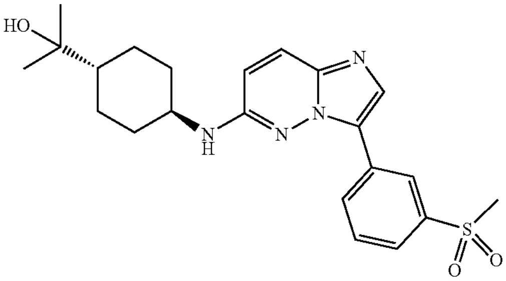

52

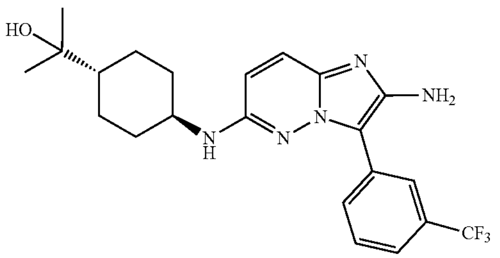

A second aspect of the present invention provides a method for preparing a compound having a structure represented by general formula (II), which comprises the following steps:

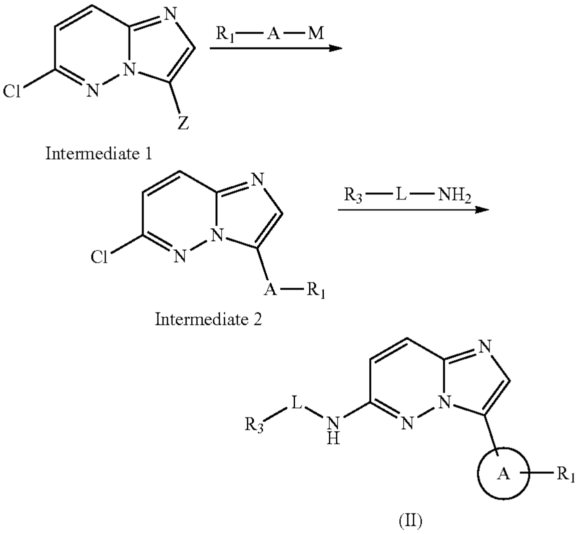

Intermediate 1

Intermediate 2

(II)

wherein, Z is H or I, M is halogen or a boronate group, and other groups are defined in the same way as those in the compound having the structure represented by general formula (II). Intermediate 1 firstly reacts with a compound $R_1$-A-M to give intermediate 2, which then reacts with $R_3$-L-$NH_2$ to give the compound having the structure represented by general formula (II).

In some preferred embodiments, the Z atom in intermediate 1 may be H. When Z is H, M is halogen. In this case, intermediate 1 is subjected to a Heck coupling reaction with $R_1$-A-M to give intermediate 2. In some other preferred embodiments, the Z atom in intermediate 1 may be I. When Z is I, M is a boronate group. In this case, intermediate 1 is subjected to a Suzuki coupling reaction with $R_{1\text{-}a\text{-}M}$ to give intermediate 2.

In some preferred embodiments, intermediate 2 is subjected to a nucleophilic substitution reaction with $R_3$-L-$NH_2$ to give the compound having the structure represented by general formula (II). In some other preferred embodiments, intermediate 2 is subjected to a Buchwald-Hartwig coupling reaction with $R_3$-L-$NH_2$ to give the compound having the structure represented by general formula (II).

A third aspect of the present invention provides a pharmaceutical composition comprising the compound, or the deuteride, the stereoisomer, or the pharmaceutically acceptable salt thereof according to any one of the embodiments described above, and a pharmaceutically acceptable carrier therefor.

A fourth aspect of the present invention provides use of the compound, or the deuteride, the stereoisomer, or the pharmaceutically acceptable salt thereof according to any one of the embodiments described above, or the pharmaceutical composition according to any one of the embodiments described above in the preparation of a medicament for treating and/or preventing a PIM-related disease.

In some preferred embodiments, the PIM-related disease includes an autoimmune disease or a tumor.

In some more preferred embodiments, the PIM-related disease includes an inflammatory bowel disease, a hematological tumor, or a solid tumor;

In some further preferred embodiments, the hematological tumor includes, but is not limited to, acute myeloid leukemia, myelofibrosis, chronic lymphocytic leukemia, and the like; the solid tumor includes, but is not limited to, gastric cancer, prostate cancer, and the like.

A fifth aspect of the present invention provides use of the compound, or the deuteride, the stereoisomer, or the pharmaceutically acceptable salt thereof according to any one of the embodiments described above, or the pharmaceutical composition according to any one of the embodiments described above as a PIM kinase inhibitor.

In some preferred embodiments, the PIM kinase inhibitor is used for treating and/or preventing a PIM-related disease, e.g., an autoimmune disease or a tumor.

In some more preferred embodiments, the PIM-related disease includes an inflammatory bowel disease, a hematological tumor, or a solid tumor;

In some further preferred embodiments, the hematological tumor includes, but is not limited to, acute myeloid leukemia, myelofibrosis, chronic lymphocytic leukemia, and the like; the solid tumor includes, but is not limited to, gastric cancer, prostate cancer, and the like.

A sixth aspect of the present invention provides a method for treating and/or preventing a PIM-related disease, which comprises administering to a subject a therapeutically effective amount of the compound, or the deuteride, the stereoisomer, or the pharmaceutically acceptable salt thereof according to any one of the embodiments described above, or the pharmaceutical composition according to any one of the embodiments described above.

In some preferred embodiments, the PIM-related disease includes an autoimmune disease or a tumor.

In some more preferred embodiments, the PIM-related disease includes an inflammatory bowel disease, a hematological tumor, or a solid tumor;

In some further preferred embodiments, the hematological tumor includes, but is not limited to, acute myeloid leukemia, myelofibrosis, chronic lymphocytic leukemia, and the like; the solid tumor includes, but is not limited to, gastric cancer, prostate cancer, and the like.

The compound provided by the present invention has a good PIM kinase inhibition effect, has stronger cell inhibition activity and lower toxic and side effects compared with a PIM inhibitor TP-3654, and has strong drug efficacy, good pharmacokinetic properties, and high bioavailability. It is a novel ideal PIM inhibitor with high activity and low toxicity, and can be used for treating and/or preventing diseases such as a hematological tumor including acute myeloid leukemia, myelofibrosis, or chronic lymphocytic leukemia, and a solid tumor including gastric cancer or prostate cancer.

DETAILED DESCRIPTION

Definitions

The numerical interval, as used herein, includes endpoint values and any numerical values between the endpoint values. For example, "0-3" may include 0, 1, 2, or 3, and "1-3" may include 1, 2, or 3.

As used herein, "$C_1$-$C_n$" includes $C_1$-$C_2$, $C_1$-$C_3$, . . . , $C_1$-$C_n$. For example, a "$C_1$-$C_6$" group refers to a moiety having 1-6 carbon atoms, that is, the group contains 1 carbon atom, 2 carbon atoms, 3 carbon atoms, 4 carbon atoms, 5 carbon atoms, or 6 carbon atoms. Thus, for example, "$C_1$-$C_4$ alkyl" refers to an alkyl group containing 1-4 carbon atoms, that is, the alkyl is selected from methyl, ethyl, propyl, isopropyl, n-butyl, isobutyl, sec-butyl, and tert-butyl. The numerical ranges herein, e.g., "1-6", refer to integers in the given range.

The term "alkyl" as used herein, alone or in combination, refers to an optionally substituted linear or optionally substituted branched saturated aliphatic hydrocarbon. The "alkyl" herein may preferably have 1-6 carbon atoms, e.g., 1-5 carbon atoms, 1-4 carbon atoms, or 1-3 carbon atoms. Non-limiting examples of the alkyl include methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3 -methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1 -butyl, n-butyl, isobutyl, sec-butyl, tert-butyl, n-pentyl, isopentyl, neopentyl, tert-pentyl, hexyl, and the like. In the groups defined herein, for example, when a numerical range appears for "alkyl", e.g., "$C_1$-$C_6$ alkyl", it means that an alkyl group may be composed of 1 carbon atom, 2 carbon atoms, 3 carbon atoms, 4 carbon atoms, 5 carbon atoms, or 6 carbon atoms. The alkyl herein also encompasses instances where no numerical range is specified. The alkyl may be optionally substituted or unsubstituted. The "alkyl" as used herein in combination refers to an alkyl group connected to another group, for example, an alkyl group in an alkoxy group, which is defined in the same way as when used alone. The term "alkylene" as used herein, alone or in combination, refers to a saturated divalent aliphatic hydrocarbyl obtained by the removal of two hydrogen atoms from a linear or branched saturated aliphatic hydrocarbyl. The "alkylene" herein may preferably have 1-6 carbon atoms, e.g., 1-5 carbon atoms, 1-4 carbon atoms, or 1-3 carbon atoms. Non-limiting examples of the alkylene include $—CH_2$- (i.e., methylene), $—CH_2$-$CH_2$- (i.e., ethylene), $—CH_2$-$CH_2$-$CH_2$-, $—CH(CH_3)CH_2$-, $—C(CH_3)_2$-, $—CH_2$-$C(CH_3)$-$CH_2$, $—CH_2$-$CH_2$-$CH_2$-$CH_2$-, $—CH_2C(CH_3)$-$CH_2$-$CH_2$-, $—CH_2$-$CH_2$-$CH_2$-$CH_2$-, $—CH_2$-$CH_2$-$CH_2$-$CH_2$-$CH_2$-$CH_2$-, and the like. The alkylene may be optionally substituted or unsubstituted.

The term "heteroalkyl" as used herein, alone or in combination, refers to a group obtained by the replacement of a carbon atom in an alkyl group with one or more heteroatoms selected from nitrogen, oxygen, and sulfur, wherein the alkyl group is defined in the same way as the "alkyl" described above.

The term "alkoxy" as used herein, alone or in combination, is denoted as "alkyl—O-". Non-limiting examples of the alkoxy include methoxy, ethoxy, n-propoxy, isopropoxy, n-butoxy, isobutoxy, sec-butoxy, tert-butoxy, and the like. The alkoxy may be optionally substituted or unsubstituted.

The term "cycloalkyl" as used herein, alone or in combination, refers to carbocyclic rings such as saturated monocyclic ring, bicyclic ring, fused ring, bridged ring, and spiro ring. The cycloalkyl herein is preferably $C_3$-$C_{12}$ cycloalkyl, more preferably $C_3$-$C_{10}$ cycloalkyl, and most preferably $C_3$-$C_8$ cycloalkyl. Non-limiting examples of the monocyclic cycloalkyl include, but are not limited to, cyclopropyl, cyclobutyl, cyclopentyl, cyclohexyl, cycloheptyl, cyclooctyl, and other cycloalkyl groups, which may be optionally substituted or unsubstituted.

In the definition of "cycloalkyl", the "spiro ring" refers to an all-carbon polycyclic group of two or more cyclic structures with single rings sharing one carbon atom (referred to as a spiro atom). The spiro ring herein is preferably 6- to 12-membered, and more preferably 8- to 9-membered.

According to the number of Spiro atoms shared by the rings, the spiro ring includes monospiro cycloalkyl, bispiro cycloalkyl, or polyspiro cycloalkyl. The spiro ring herein is preferably monospiro cycloalkyl or bispiro cycloalkyl, and preferably 4-membered/5-membered, 4-membered/6-membered, 5-membered/5-membered, or 5-membered/6-membered spiro cycloalkyl. In the definition of "cycloalkyl", "fused ring" refers to an all-carbon polycyclic group containing two or more cyclic structures with rings sharing a pair of carbon atoms. The fused ring herein is preferably 6- to 12-membered, and more preferably 8- to 9-membered. According to the number of the formed rings, the fused ring may include bicyclic, tricyclic, tetracyclic, or polycyclic fused cycloalkyl. The fused ring herein is preferably bicyclic or tricyclic, and more preferably 5-membered/5-membered, 5-membered/6-membered, or 6-membered/6-membered bicyclic heterocyclyl.

In the definition of "cycloalkyl", "bridged ring" refers to an all-carbon polycyclic group containing two or more cyclic structures with rings sharing two carbon atoms not directly connected. The bridged ring herein is preferably 6- to 12-membered, and more preferably 8- to 9-membered. According to the number of the formed rings, the bridged ring may include bicyclic, tricyclic, tetracyclic, or polycyclic bridged cycloalkyl, and is preferably bicyclic or tricyclic.

The term "heteroaryl" as used herein, alone or in combination, refers to a 5- to 12-membered (preferably 5- to 10-membered, more preferably 5- to 6-membered) monocyclic, bicyclic, or tricyclic ring system in which at least one ring is aromatic and at least one ring contains one or more heteroatoms selected from nitrogen, oxygen, and sulfur. Meanwhile, the heteroaryl has one or more attachment points connected to the rest of the molecule. Examples of the heteroaryl include, but are not limited to, furyl, imidazolyl, isoxazolyl, oxazolyl, pyrrolyl, pyrazolyl, pyridinyl, pyrimidinyl, pyridazinyl, pyrazinyl, thienyl, thiazolyl, and the like; and also include, but are not limited to, the following bicyclic rings: benzimidazolyl, benzofuranyl, benzothienyl, indolyl, oxoindolyl, dihydroindolyl, imidazopyridinyl, pyrazolopyridinyl, pyrazolopyrimidinyl, quinolinyl, isoquinolinyl, quinazolinyl, and the like. The heteroaryl may be optionally substituted or unsubstituted.

The term "heterocyclyl" as used herein, alone or in combination, includes both aliphatic and aromatic heterocyclyl groups in which one or more of the ring-forming atoms are heteroatoms, such as oxygen, nitrogen, or sulfur atom, and includes monocyclic, fused, bridged, and spiro rings. The heterocyclyl herein is preferably 3- to 10-membered monocyclic, bicyclic, or tricyclic heterocyclyl, which may contain 1, 2, or 3 ring atoms selected from nitrogen, oxygen, and/or sulfur. Non-limiting examples of the "heterocyclyl" include morpholinyl, oxetanyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1] octyl, piperazinyl, and the like. The heterocyclyl may be optionally substituted or unsubstituted.

In the definition of "heterocyclyl", "spiro ring" refers to a polycyclic group of two or more cyclic structures with single rings sharing one atom, wherein the rings contain 1 or more double bonds, but none of the rings has a fully conjugated pi-electron aromatic system, wherein one or more of the ring atoms are heteroatoms selected from nitrogen, oxygen, and $S(O)_n$ (wherein n is selected from 0, 1, and 2), and the remaining ring atoms are carbon. The spiro ring herein is preferably 6- to 12-membered, and more preferably 8- to 9-membered. According to the number of spiro atoms shared by the rings, the spiro ring includes monospiro heterocyclyl, bispiro heterocyclyl, or polyspiro heterocyclyl, and is preferably monospiro heterocyclyl or bispiro heterocyclyl, and more preferably 4-membered/4-membered, 4-membered/5-membered, 4-membered/6-membered, 5-membered/5-membered, or 5-membered/6-membered monospiro heterocyclyl.

In the definition of "heterocyclyl", "fused ring" refers to a polycyclic group containing two or more cyclic structures with the rings sharing a pair of atoms, wherein one or more of the rings may contain one or more double bonds, while at least one ring has a fully conjugated pi-electron aromatic system, wherein one or more of the ring atoms are heteroatoms selected from nitrogen, oxygen, and S(O). (wherein n is selected from 0, 1, and 2), and the remaining ring atoms are carbon. The fused ring herein is preferably 6- to 12-membered, and more preferably 8- to 9-membered. According to the number of the formed rings, the fused heterocyclyl may include bicyclic, tricyclic, tetracyclic, or polycyclic fused heterocyclyl, and is preferably bicyclic or tricyclic fused heterocyclyl, and more preferably 5-membered/5-membered or 5-membered/6-membered bicyclic fused heterocyclyl.

In the definition of "heterocyclyl", "bridged ring" refers to a polycyclic group containing two or more cyclic structures with the rings sharing two atoms not directly connected, wherein one or more of the rings may contain one or more double bonds, but none of the rings has a fully conjugated pi-electron aromatic system, wherein one or more of the ring atoms are heteroatoms selected from nitrogen, oxygen, and S(O). (wherein n is selected from 0, 1, and 2), and the remaining ring atoms are carbon. The bridged ring herein is preferably 6- to 12-membered, and more preferably 8- to 9-membered. According to the number of the formed rings, the bridged ring may include bicyclic, tricyclic, tetracyclic, or polycyclic bridged heterocyclyl, and is preferably bicyclic or tricyclic.

The term "halogen" as used herein, alone or in combination, refers to fluorine, chlorine, bromine, or iodine.

The term "hydroxyl" as used herein, alone or in combination, refers to —OH.

The term "cyano" as used herein, alone or in combination, refers to —CN.

The term "methanesulfonyl" as used herein, alone or in combination, refers to $—S(O)_2-CH_3$.

The term "substituted" or "substituted with . . . " as used herein means that one or more hydrogens on one specific atom are replaced with a designated group (e.g., halogen, alkyl, etc.), which results in a stable compound if the normal valency of the specified atom is not exceeded under existing conditions.

The term "pharmaceutically acceptable salt" as used herein is well known in the field to which it belongs to those skilled in the art.

The term "pharmaceutically acceptable" as used herein refers to a substance (e.g., carrier or diluent) that does not affect the biological activity or properties of the compound of the present invention and is relatively non-toxic, that is, the substance can be administered to an individual without causing an undesirable biological response or interacting in an undesirable manner with any of the components contained in the composition.

The term "pharmaceutical composition" as used herein refers to a biologically active compound optionally mixed with at least one pharmaceutically acceptable chemical ingredient including, but not limited to, carriers, stabilizers, diluents, dispersants, suspending agents, thickening agents, and/or excipients.

The term "carrier" as used herein refers to a relatively non-toxic chemical compound or agent that facilitates the introduction of the compound into a cell or tissue.

The term "stereoisomer" as used herein includes, but is not limited to, an enantiomer, a cis-trans isomer, and the like.

The term "enantiomer" as used herein refers to the isomerism caused by different spatial configurations of atoms or groups of atoms (groups) in compounds with identical molecular formulas. Two compounds that are enantiomers of each other are mirror images of each other and cannot be overlapped. The term "cis-trans isomer" as used herein generally refers to the stereoisomerism of compound molecules that are diastereoisomeric due to the different spatial arrangements of groups as a result of the free rotation restriction. Organic molecules containing such isomerism, such as olefins, azo compounds, or alicyclic hydrocarbons, are considered cis-trans isomers. In the present application, the cis-trans isomerism is mainly embodied in the form of alicyclic hydrocarbons. For example, in cyclohexane, the cis-trans isomerism occurs when the cyclohexane is substituted with two substituents. These two substituents result in a "cis" isomer when performing the substitution on the same side of the ring, and result in a "trans" isomer when performing the substitution on different sides.

The compounds of the present invention may contain asymmetric or chiral centers and thus exist in different stereoisomeric forms. It is contemplated that all stereoisomeric forms of the compounds of the present invention, including but not limited to diastereoisomers, enantiomers, atropisomers, and geometric (conformational) isomers, and mixtures thereof, such as racemic mixtures, are within the scope of the present invention.

Unless otherwise indicated, the structures described herein also include all isomers (e.g., diastereoisomers, enantiomers, cis-trans isomers, atropisomers, geometric (conformational) isomeric forms) of such structures, e.g., R and S configurations at various asymmetric centers, (Z) and (E) double bond isomers, cis-trans isomers of aliphatic cyclic hydrocarbons, atropisomers of biphenyl structures (see, Basic Organic Chemistry ($2^{nd}$ Ed.) Vol. 1, Xing Qiyi et al., p104-105; PAC, 1996, 68, 2193. (Basic terminology of stereochemistry (IUPAC Recommendations 1996, on page 2201))), or (Z) and (E) conformational isomers. Thus, individual stereoisomers, as well as mixtures of enantiomers, mixtures of diastereoisomers, atropisomers, and mixtures of geometric (conformational) isomers of the compound of the present invention are all within the scope of the present invention.

In the following examples, the prepared compounds all have the structure represented by general formula (I):

(I)

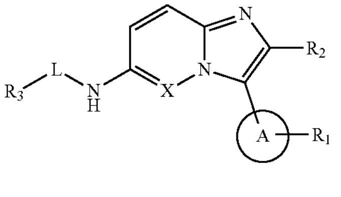

wherein:

- ring A is 5- to 6-membered aryl or 5- to 6-membered heteroaryl, the 5- to 6-membered heteroaryl comprising at least 1 heteroatom selected from N, O, and S;
- X is a C or N atom;
- L is a chemical bond or methylene;
- $R_1$ is selected from hydrogen, halogen, hydroxyl, cyano, —$NH_2$, —$C_1$-$C_6$ alkyl, —O($C_1$-$C_6$ alkyl), —NH($C_1$-$C_6$ alkyl), trifluoromethyl, and trifluoromethyloxy;
- $R_2$ is selected from hydrogen, halogen, hydroxyl, carboxyl, cyano, —$NH_2$, —$C_1$-$C_6$ alkyl, —O($C_1$-$C_6$ alkyl), —NH($C_1$-$C_6$ alkyl), trifluoromethyl, and trifluoromethyloxy;
- $R_3$ is selected from 3- to 10-membered saturated or unsaturated hydrocarbyl (including linear or branched alkyl or heteroalkyl), monocyclic or bicyclic cycloalkyl or heterocycloalkyl, and monocyclic or bicyclic aryl or heteroaryl, the heteroalkyl, heterocyclyl, or heteroaryl comprising at least 1 heteroatom selected from N, O, and S; the $R_3$ is optionally substituted with 1-3 $R^a$;
- the $R^a$ is selected from hydrogen, halogen, hydroxyl, carboxyl, cyano, —$NH_2$,—$C_1$-$C_6$ alkyl, —O($C_1$-$C_6$ alkyl), —NH($C_1$-$C_6$ alkyl), trifluoromethyl, trifluoromethyloxy, and —($C_1$-$C_6$ alkylene)—OH. Part of the compounds also fit into the structure represented by general formula (II):

(II)

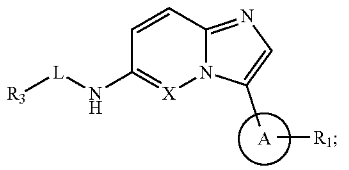

wherein:

- ring A is phenyl or 5-membered heteroaryl, the 5-membered heteroaryl comprising 1 or 2 heteroatoms optionally selected from N, O, and S; ring A is substituted with $R_1$; L is a chemical bond or methylene;
- $R_1$ is selected from hydrogen, halogen, hydroxyl, cyano, —$NH_2$, —$C_1$-$C_6$ alkyl, —O($C_1$-$C_6$ alkyl), —NH($C_1$-$C_6$ alkyl), —N($C_1$-$C_6$ alkyl)$_2$, trifluoromethyl, and trifluoromethyloxy;
- $R_3$ is selected from 3- to 10-membered monocyclic or bicyclic cycloalkyl or heterocyclyl, the heterocyclyl comprising 1 or 2 heteroatom optionally selected from N, O, and S; the $R_3$ is optionally substituted with 1-3 $R^a$;
- $R^a$ is selected from hydrogen, halogen, hydroxyl, carboxyl, cyano, —$NH_2$, —$C_1$-$C_6$ alkyl, -O($C_1$-$C_6$ alkyl), —NH($C_1$-$C_6$ alkyl), trifluoromethyl, trifluoromethyloxy, and —($C_1$-$C_6$ alkylene)—OH.

Generally, the compound having the structure represented by general formula (II) can be synthesized by the following method.

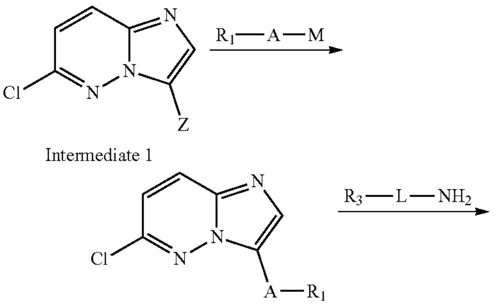

Intermediate 1

Intermediate 2

-continued

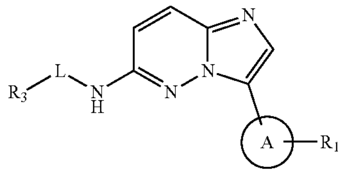

(II)

wherein Z is H or I, M is halogen or a boronate group, and other groups are defined in the same way as those in the compound having the structure represented by general formula (II). Intermediate 1 firstly reacts with a compound $R_1$-A-M to give intermediate 2, which then reacts with $R_3$-L-$NH_2$ to give the compound having the structure represented by general formula (II).

Step 1: synthesis of intermediate 2

When the Z atom of intermediate 1 is H, M is halogen. In this case, intermediate 1 is subjected to a Heck coupling reaction with $R_1$-A-X to give intermediate 2. At this time, the specific reaction conditions are as follows:

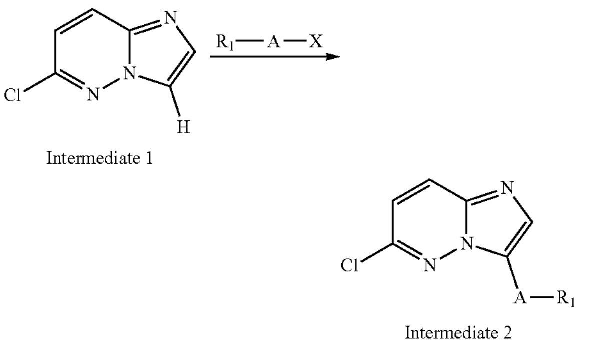

$R_1$-A-X, a Pd catalyst, a carrier, and a base are sequentially added to a solution of intermediate 1 at room temperature under nitrogen atmosphere, and the mixture is reacted at a temperature higher than room temperature. After the reaction is completed as monitored by a method such as TLC or LCMS, intermediate 2 is obtained. The solvent, the Pd catalyst, the carrier, and the base may be selected from common Heck reaction systems. In some specific embodiments, the solvent may be selected from toluene, DMF, NMP, and the like. In some specific embodiments, the Pd catalyst may be palladium chloride, palladium acetate, or tetrakis(triphenylphosphine)palladium(0), and under certain special conditions, copper catalysts such as cuprous iodide may also be used. In some specific embodiments, the carrier may be selected from triphenylphosphine, BINAP, and the like. In some specific embodiments, the base may be triethylamine, potassium carbonate, sodium acetate, or potassium acetate. The reaction temperature is higher than room temperature, or may be selected from the reflux temperature for the solvent or a temperature slightly lower than the reflux temperature, and specifically may be any one of 20-120° C.

When the Z atom in intermediate 1 is I, M is a boronate group. In this case, intermediate 1 is subjected to a Suzuki coupling reaction with $R_1$-A-M to give intermediate 2. At this time, the specific reaction conditions are as follows:

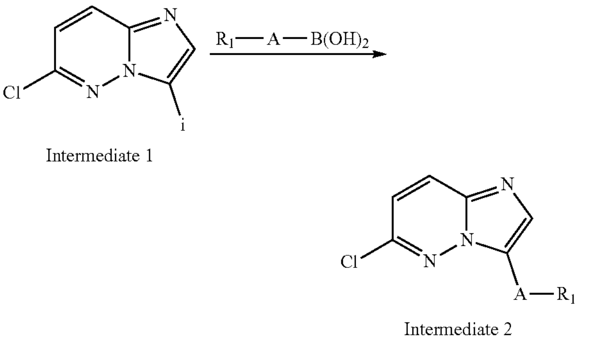

$R_1$-A-$B(OH)_2$, a Pd catalyst, a carrier, and a base are sequentially added to a solution of intermediate 1 at room temperature under nitrogen atmosphere, and the mixture is reacted at a temperature higher than room temperature. After the reaction is completed as monitored by a method such as TLC or LCMS, intermediate 2 is obtained. The solvent, the Pd catalyst, the carrier, and the base may be selected from common Suzuki reaction systems. In some specific embodiments, the solvent may be selected from toluene, dioxane, water, and a combination thereof. In some specific embodiments, the Pd catalyst may be palladium chloride, Pd/C, palladium acetate, tetrakis(triphenylphosphine)palladium (0), or $Pd_2(dba)_3$, and under certain special conditions, nickel catalysts may also be used. In some specific embodiments, the carrier may be selected from triphenylphosphine, BINAP, $PCy_3$, and the like. In some specific embodiments, the base may be potassium carbonate, sodium carbonate, cesium carbonate, or lithium carbonate. The reaction temperature is higher than room temperature, or may be selected from the reflux temperature for the solvent and a temperature slightly lower than the reflux temperature, and specifically may be any one of 80-110° C.

Step 2: synthesis of the compound having the structure represented by general formula (II).

For part of the compounds, a nucleophilic substitution reaction is suitable. At this time, the specific reaction conditions are as follows:

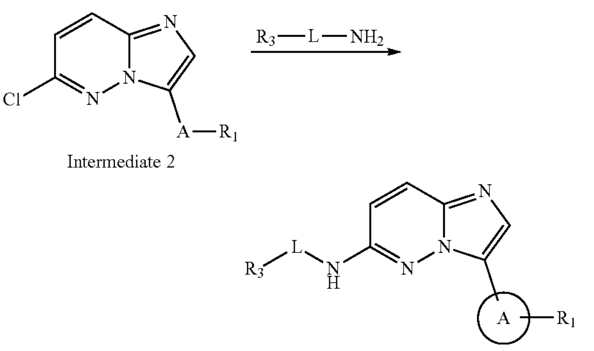

(II)

$R_3$-L-$NH_2$ and a base are sequentially added to a solution of intermediate 2 in dimethyl sulfoxide at room temperature, and the mixture was heated and reacted. After the reaction was completed as monitored by a method such as TLC or LCMS, the compound having the structure represented by general formula (II) is obtained. In some specific embodiments, the base may be selected from cesium fluoride, potassium fluoride, cesium fluoride, N,N-diisopropylethylamine, and a combination thereof, or no base is added. In some specific embodiments, the reaction temperature is generally higher than room temperature, and specifically may be any value of 100-140° C.

For the other part of the compounds, a Buchwald-Hartwig coupling reaction is more suitable. At this time, the specific reaction conditions are as follows:

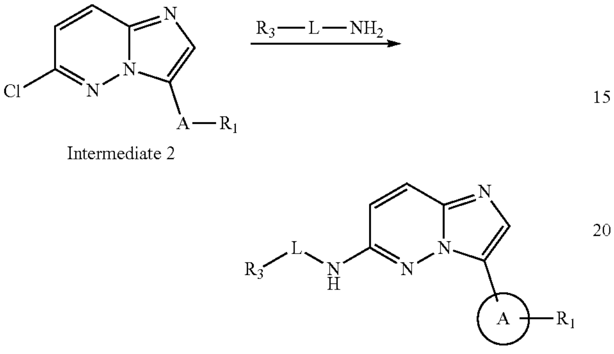

Intermediate 2

(II)

$R_3$-L—$NH_2$, a Pd catalyst, a carrier, and a base are sequentially added to a solution of intermediate 2 at room temperature under nitrogen atmosphere, and the mixture is reacted at a temperature higher than room temperature. After the reaction is completed as monitored by a method such as TLC or LCMS, the compound having the structure represented by general formula (II) is obtained. The solvent, the Pd catalyst, the carrier, and the base may be selected from common Buchwald-Hartwig reaction systems. In some specific embodiments, the solvent may be selected from toluene, dioxane, water, and a combination thereof. In some specific embodiments, the catalyst may be palladium acetate or Pd2(dba)3. In some specific embodiments, the carrier may be selected from $P(t\text{-}Bu)_3$, BINAP, $P(o\text{-}tolyl)_3$, and Xantphos. In certain specific embodiments, the base may be cesium carbonate, potassium tert-butoxide, or sodium tert-butoxide. The reaction temperature is higher than room temperature, or may be selected from the reflux temperature for the solvent and a temperature slightly lower than the reflux temperature, and specifically may be any one of 80-110° C.

The present invention will be further illustrated in detail below with reference to specific examples, but the present invention is not limited thereto.

Part of the preparation conditions used in the examples are as follows:

preparative Pre-HPLC conditions: instrument: GILSON-GX281; wavelength: 220 nm & 254 nm; column type: Waters X-bridge (30×100 mm, 10 μm) or Luna C18 (30×75 mm, 3 μm) or Luna C18 (30×75 mm, 3 μm); mobile phase: A: 10 mM ammonium bicarbonate or $H_2O$ (0.1% formic acid) or $H_2O$ (0.1% trifluoroacetic acid), B: acetonitrile; run time: 15 min; flow rate: 25 mL/min.

The reverse column purification is performed using a C18 reverse silica gel column (Spherical C18, 40-60 μm, 40-120 g) with water/acetonitrile (95/5-30/70) as the mobile phase.

EXAMPLE 1

6-(((1-methylpiperidin-4-yl)methyl)amino)-3-(3-(trifluoromethoxy)phenyl)imidazo[1,2-b]pyridazine-2-carboxylic Acid (compound 6)

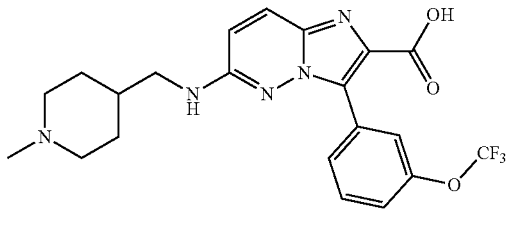

6

(1) Ethyl 3-bromo-6-chloroimidazo [1,2-b] pyridazine-2-carboxylate

Ethyl 6-chloroimidazo[1,2-b]pyridazine-2-carboxylate (1.0 g, 3.92 mmol) was dissolved in dichloromethane (15 mL), followed by the addition of NBS (1.1 g, 5.88 mmol). The reaction system was stirred for reaction at room temperature overnight. Water was added to the reaction solution. The mixed solution was extracted with dichloromethane, followed by liquid separation. The organic phase was washed with saturated brine (10 mL), dried over anhydrous sodium sulfate, and concentrated under reduced pressure. The crude product was purified by reverse phase column chromatography to give ethyl 3-bromo-6-chloroimidazo[1,2-b]pyridazine-2-carboxylate (310 mg, yield: 24%) as a yellow solid. MS (ESI): m/z 305.8 $[M+H]^+$.

(2) Ethyl 6-chloro-3-(3-(trifluoromethoxy)phenyl)imidazo[1,2-b]pyridazine-2-carboxylate Tetrakis(triphenylphosphine)palladium(0) (185 mg, 0.16 mmol) was added to a mixed solution of ethyl 3-bromo-6-chloroimidazol[1,2-b]pyridazine-2-carboxylate (500 mg, 1.64 mmol), (3-(trifluoromethoxy)phenyl)boronic acid (185 mg, 0.16 mmol), and potassium carbonate (375 mg, 4.94 mmol) in dioxane and water (5:1, 12 mL) under nitrogen atmosphere. The reaction system was heated to 90° C. and stirred overnight. The reaction system was directly concentrated under reduced pressure. The crude product was purified by reverse phase column chromatography to give ethyl 6-chloro-3-(3-(trifluoromethoxy)phenyl)imidazo[1,2-b] pyridazine-2-carboxylate (310 mg, yield: 49%) as a yellow solid. MS (ESI): m/z 385.9 $[M+H]^+$.

(3) 6-(((1-methylpiperidin-4-yl)methyl)amino)-3-(3-(trifluoromethoxy)phenyl)imidazo[1,2-b]pyridazine-2-carboxylic Acid Ethyl 6-chloro-3-(3-(trifluoromethoxy)phenyl)imidazo[1,2-b]pyridazine-2-carboxylate (100 mg, 0.26 mmol) was dissolved in toluene (5 mL), followed by the addition of sodium tert-butoxide (75 mg, 0.78 mmol), BINAP (23 mg, 0.05 mmol), tris(dibenzylideneacetone)dipalladium(0) (27 mg, 0.03 mmol), and (1-methylpiperidin-4-yl)methylamine (66 mg, 0.52 mmol). The reaction system was purged with nitrogen and reacted at 100° C. overnight. The reaction solution was filtered, and the filtrate was concentrated to dryness and directly purified by reverse phase column chromatography to give a crude product. The crude product was purified by Prep-HPLC to give 6-(((1-methylpiperidin-4-yl)methyl)amino)-3-(3- (trifluoromethoxy)phenyl)imidazo[1,2-b]pyridazine-2-carboxylic acid (8.5 mg, yield: 7%) as a white solid. MS (ESI): m/z 450.2 $[M+H]^+$. $^1H$ NMR (400 MHz, DMSO-$d_6$) δ 7.77-7.72 (m, 3H), 7.55 (t, J=8.4

Hz, 1H), 7.38 (d, J=8.4 Hz, 1H), 7.28 (t, J=5.6 Hz, 1H), 6.82 (d, J=9.6 Hz, 1H), 2.99 (t, J=6.0 Hz, 2H), 2.87-2.81 (m, 2H), 2.23 (s, 3H), 2.00 (t, J=11.6 Hz, 2H), 1.65-1.58 (m, 3H), 1.24-1.18 (m, 2H).

EXAMPLE 2

N-((1-methylpiperidin-4-yl)methyl)-3-(pyridin-3-yl)imidazo[1,2-a]pyridin-6-amine (compound 7)

7

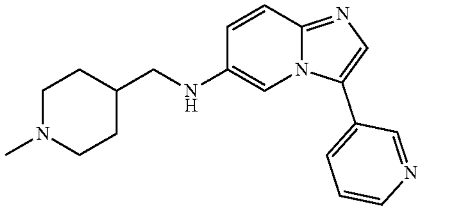

(1) 6-chloro-3-(pyridin-3-yl)imidazo[1,2-a]pyridine

Referring to the procedures in step (2) of Example 1, 3-bromo-6-chloroimidazo[1,2-a]pyridine (200 mg, 0.86 mmol) and pyridin-3-ylboronic acid (105 mg, 0.86 mmol) were used as starting materials to give a product 6-chloro-3-(pyridin-3-yl)imidazo[1,2-a]pyridine (67 mg, yield: 34%) as a yellow oily liquid. MS (ESI): m/z 230 $[M+H]^+$.

(2) N-((1-methylpiperidin-4-yl)methyl)-3-(pyridin-3-yl)imidazo[1,2-a]pyridin-6-amine Referring to the procedures in step (3) of Example 1, 6-chloro-3-(pyridin-3-yl)imidazo[1,2-a]pyridine (67 mg, 0.29 mmol) and (1-methylpiperidin-4-yl)methylamine (37.6 mg, 0.29 mmol) were used as starting materials to give N-((1-methylpiperidin-4-yl)methyl)-3-(pyridin-3-yl)imidazo[1,2-a]pyridin-6-amine (10.9 mg, yield: 11%) as a white solid. MS (ESI): m/z 323.2 $[M+H]^+$. $^1$H NMR (400 MHz, DMSO-$d_6$) δ 9.37 (s, 1H), 8.56 (d, J=8.0 Hz, 1H), 8.49 (s, 1H), 8.06 (s, 1H), 7.78 (d, J=8.0 Hz, 1H), 7.49-7.45 (m, 1H), 7.20 (t, J=6.4 Hz, 1H), 6.76 (d, J=9.6 Hz, 1H), 3.17 (t, J=6.0 Hz, 2H), 2.80 (d, J=11.2 Hz, 2H), 2.14 (s, 3H), 1.84 (t, J=11.2 Hz, 2H), 1.74-1.65 (m, 1H), 1.29-1.20 (m, 2H).

EXAMPLE 3

1-methyl-4-(((3-(3-trifluoromethoxy)phenyl)imidazo[1,2-b]pyridazin-6-yl)amino)methyl)piperidine-4-carboxylic Acid (compound 8)

8

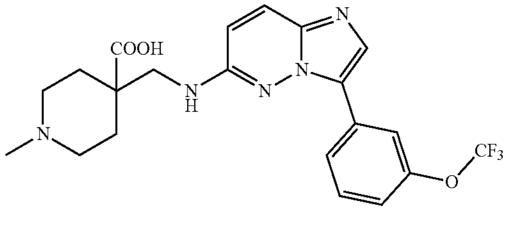

(1) 6-chloro-3-(3-(trifluoromethoxy)phenyl)imidazo[1,2-b]pyridazine

Referring to the procedures in step (2) of Example 1, 3-bromo-6-chloroimidazo[1,2-b]pyridazine (800 mg, 3.44 mmol) and (3-(trifluoromethoxy)phenyl)boronic acid (708.4 mg, 3.44 mmol) were used as starting materials to give a product 6-chloro-3-(3-(trifluoromethoxy)phenyl)imidazo[1,2-b]pyridazine (560.2 mg, yield: 52%) as a yellow solid. MS (ESI): m/z 314.0 $[M+H]^+$.

(2) 1 -(tert-butoxycarbonyl)-4-(((3-(3-(trifluoromethoxy)phenyl)imidazo[1,2-b]pyridazin-6-yl)amino)methyl)piperidine-4-carboxylic Acid Referring to the procedures in step (3) of Example 1, 6-chloro-3-(3-(trifluoromethoxy)phenyl)imidazo[1,2-b]pyridazine (510 mg, 1.63 mmol) and 4-(aminomethyl)piperidine-1,4-dicarboxylic acid 1-tert-butyl 4-ethyl ester (466 mg, 1.63 mmol) were used as starting materials to give 1-(tert-butoxycarbonyl)-4-4(3-(3-(trifluoromethoxy)phenyl)imidazo[1,2-b]pyridazin-6- yl)amino)methyl)piperidine-4-carboxylic acid (240 mg, yield: 28%) as a white solid. MS (ESI): m/z 536.0 $[M+H]^+$.

(3) 4-(((3-(3-(trifluoromethoxy)phenyl)imidazo[1,2-b]pyridazin-6-yl)amino)methyl)piperidine-4-carboxylic Acid 1-(tert-butoxycarbonyl)-4-(((3-(3-(trifluoromethoxy)phenyl)imidazo[1,2-b]pyridazin-6-yl)amino)methyl)piperidine-4-carboxylic acid (150 mg, 1.75 mmol) was dissolved in ethyl acetate (5 mL), and then a hydrochloric acid/ethyl acetate (5 mL) was added to the reaction solution. The reaction system was stirred at room temperature for 2 h. The reaction solution was concentrated under reduced pressure to give 4(((3-(3-(trifluoromethoxy)phenyl)imidazo[1,2-b]pyridazin-6-yl)amino)methyl)piperidine-4-carboxylic acid (122 mg, yield: 99%) as a white solid. MS (ESI): m/z 436.0 $[M+H]^+$.

(4) 1-methyl-4-(((3-(3-(trifluoromethoxy)phenyl)imidazo[1,2-b]pyridazin-6-yl)amino)methyl)piperidine-4-carboxylic Acid 4-(((3-(3-(trifluoromethoxy)phenyl)imidazo[1,2-b]pyridazin-6-yl)amino)methyl)piperidine-4-carboxylic acid (122 mg, 0.28 mmol) was dissolved in methanol (5 mL), followed by the addition of 37% formaldehyde solution (113.5 mg, 1.4 mmol) and sodium cyanoborohydride (35.2 mg, 0.56 mmol). The reaction system was stirred at room temperature overnight. The reaction solution was filtered, and the filtrate was dried by rotary evaporation. The residue was purified by Pre-HPLC to give 1-methyl-4-(((3-(3-(trifluoromethoxy)phenyl)imidazo[1,2-b]pyridazin-6-yl)amino)methyl)piperidine-4-carboxylic acid (35.8 mg, yield: 29%) as a white solid. MS (ESI): m/z 450.3 $[M+H]^+$. $^1$H NMR (400 MHz, DMSO-$d_6$) δ 8.45 (s, 1H), 8.19 (s, 1H), 8.10 (d, J=8.4 Hz, 1H), 8.01 (s, 1H), 7.77 (d, J=10.0 Hz, 1H), 7.56 (t, J=8.0 Hz 1H), 7.29 (d, J=8.0 Hz, 1H), 7.02 (s, 1H), 6.87 (d, J=9.6 Hz, 1H), 3.52 (s, 2H), 2.69 (d, J=10.8 Hz, 2H), 2.19 (s, 3H), 2.16-2.09 (m, 4H), 1.56 (t, J=10.4 Hz, 2H).

EXAMPLE 4

N-(1-isopropyl-1H-pyrazol-3-yl)-3-(3-(trifluoromethyl)phenyl)imidazo[1,2-b]pyridazin-6-amine (Compound 10)

10

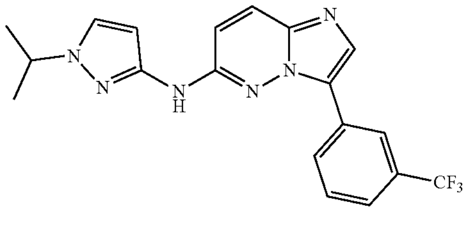

(1) 1 -isopropyl-3 -nitro-1H-pyrazole 3-nitro-1H-pyrazole (1050 mg, 9.2 mmol) and NaH (446 mg, 11.1 mmol) were dissolved in DMF (5 mL). The reaction system was stirred at 0° C. for 0.5 h, and then 2-bromopropane (1250 mg, 10.2 mmol) was added thereto. The reaction system was stirred for reaction at room temperature overnight. The reaction was quenched by adding a small amount of water. The mixed solution was extracted with ethyl acetate, followed by liquid separation. The organic phase was washed with saturated brine, dried over anhydrous sodium sulfate, filtered, concentrated under reduced pressure, and purified by reverse phase column chromatography to give 1-isopropyl-3-nitro-1H-pyrazolo[2,3-b]pyridine (320 mg, yield: 23%) as a colorless oil. MS (ESI): m/z 156.1 $[M+H]^+$.

(2) 1-isopropyl-1H-pyrazol-3-amine 1-isopropyl-3-nitro-1H-pyrazole (200 mg, 1.2 mmol) and Pd/C (100 mg) were added to a methanol (4 mL) solution. The reaction system was heated to 40° C. under hydrogen atmosphere and stirred for reaction overnight. The reaction solution was filtered, and the filtrate was dried by rotatory evaporation to give 1-isopropyl-1H-pyrazol-3-amine (120 mg, yield: 74%) as a colorless oil. MS (ESI): m/z 126.1 $[M+H]^+$.

(3) 6-chloro-3-(3-(trifluoromethyl)phenyl)imidazo[1,2-b]pyridazine

Referring to the procedures in step (2) of Example 1, 3-bromo-6-chloroimidazo[1,2-b]pyridazine (300 mg, 1.2 mmol) and (3-(trifluoromethyl)phenyl)boronic acid (246 mg, 1.2 mmol) were used as starting materials to give 6-chloro-3-(3-(trifluoromethyl)phenyl)imidazo[1,2-b]pyridazine (120 mg, yield: 31%) as a yellow solid. MS (ESI): m/z 298.3 $[M+H]^+$.

(4) N-(1 -is opropyl-1H-pyrazol-3-yl)-3-(3-(trifluoromethyl)phenyl)imidazo[1,2-b]pyridazin-6-amine Referring to the procedures in step (3) of Example 1, 6-chloro-3-(3-(trifluoromethyl)phenyl)imidazo[1,2-b]pyridazine (120 mg, 0.4 mmol) and 1-isopropyl-1H-pyrazol-3-amine (50 mg, 0.4 mmol) were used as starting materials to give N-(1-isopropyl-1H-pyrazol-3-yl)-3-(3-(trifluoromethyl)phenyl)imidazo[1,2-b]pyridazin- 6-amine (15.8 mg, yield: 10%) as a white solid. MS (ESI): m/z 387.2 $[M+H]^+$. $^1H$ NMR(400 MHz, DMSO-$d_6$) 10.01 (s, 1H), 8.58 (s, 1H), 8.32-8.29 (m, 1H), 8.04 (s, 1H), 7.93 (d, J=9.6 Hz, 1H), 7.75-7.70 (m, 2H), 7.62 (s, 1H), 7.03 (d, J=9.6 Hz, 1H), 6.54 (s, 1H), 4.48-4.38 (m, 1H), 1.42-1.40 (m, 6H).

EXAMPLE 5

2-((1r,4r)-4-((2-methyl-3-(3-(trifluoromethyl)phenyl) imidazo[1,2-b]pyridazin-6-yl)amino)cyclohexyl) propanol (compound 11)

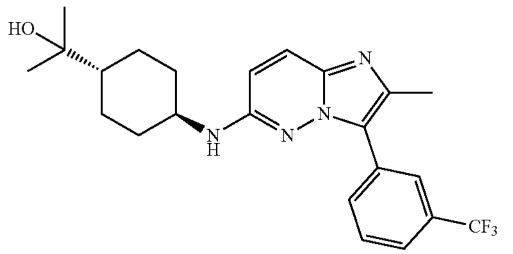

11

(1) 3-bromo-6-chloro-2-methylimidazo[1,2-b]pyridazine 6-chloro-2-methylimidazo[1,2-b]pyridazine (300 mg, 1.8 mmol) and NBS (350 mg, 1.9 mmol) were dissolved in dichloromethane (5 mL). The reaction system was reacted at room temperature overnight. The reaction solution was concentrated under reduced pressure and purified by silica gel column chromatography (PE:EA=3:1) to give 3-bromo-6-chloro-2-methylimidazo[1,2-b]pyridazine (440 mg, yield: 100%) as a white solid. MS (ESI): m/z 245.7 $[M+H]^+$.

(2) 6-chloro-2-methyl-3-(3-(trifluoromethyl)phenyl)imidazo [1,2-b]pyridazine

Referring to the procedures in step (2) of Example 1,3-bromo-6-chloro-2-methylimidazo[1,2-b]pyridazine (450 mg, 1.8 mmol) and 3-(trifluoromethyl)phenyl)boronic acid (279 mg, 1.5 mmol) were used as starting materials to give 6-chloro-2-methyl-3-(3-(trifluoromethyl)phenyl)imidazo[1,2-b]pyridazine (110 mg, yield: 19%) as a white solid. MS (ESI): m/z 311.9 $[M+H]^-$.

(3) 2-((1r,4)-4-((2methyl-3-(3-(trifluoromethyl)phenyl)imidazo[1,2-b]pyridazin-6-yl)amino)cyclohexyl)propanol Referring to the procedures in step (3) of Example 1, 6-chloro-2-methyl-3-(3-(trifluoromethyl)phenyl)imidazo[1,2-b]pyridazine (40 mg, 0.1 mmol) and 2-((1r,4r)-4-aminocyclohexyl)propanol (40 mg, 0.3 mmol) were used as starting materials to give 2-((1r,4r)-4-((2-methyl-3-(3-(trifluoromethyl)phenyl)imidazo[1,2-b]pyridazin-6-yl)amino)cyclohexyl)propanol (23.8 mg, yield: 43%) as a white solid. MS (ESI): m/z 433.4 $[M+H]^+$. $^1H$ NMR (400 MHz, DMSO-$d_6$) δ 8.35 (s, 1H), 7.93 (d, J=7.5 Hz, 1H), 7.75-7.61 (m, 3H), 6.83 (d, J=7.3 Hz, 1H), 6.65 (d, J=9.6 Hz, 1H), 4.02 (s, 1H), 3.54-3.37 (m, 1H), 2.45 (s, 3H), 2.09 (d, J=10.1 Hz, 2H), 1.81 (d, J=12.0 Hz, 2H), 1.27-0.95 (m, 11H).

EXAMPLE 6

2-[(1r,4r)-4-[[3-(2-thienyl)imidazo[1,2-b] pyridazin-6-yl]amino]cyclohexyl]propan-2-ol (compound 14)

14

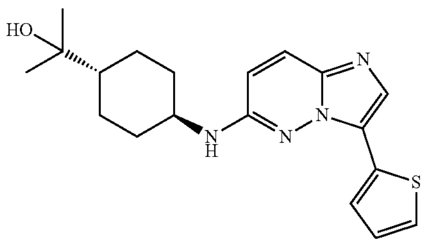

(1) 6-chloro-3-(2-thienyl)imidazo[1,2-b]pyridazine

Referring to the procedures in step (2) of Example 1, 6-chloro-3-iodo-imidazo[1,2-b]pyridazine (0.05 g, 178.9 μmol) and 2-thiopheneboronic acid (27.47 mg, 214.7 μmol) were used as starting materials for 6 batches of reaction in parallel to give 6-chloro-3-(2-thienyl)imidazo[1,2-b]pyridazine (0.2 g, yield: 79.05%) as a yellow solid. $^1H$ NMR (400 MHz, $CDCl_3$) δ 7.71-7.64 (m, 2H), 7.61-7.52 (m, 2H), 7.50-7.43 (m, 2H).

(2) 2-[4-[[3-(2-thienyl)imidazo[1,2-b]pyridazin-6-yl]amino]cyclohexyl]propan-2-ol 2-((1r,4r)-4-aminocyclohexyl)propan-2-ol (6.67 mg, 42.43 μmol), cesium fluoride (6.44 mg, 42.43 μmol), and N,N-diisopropylethylamine (5.48 mg, 42.43 μmol, 7.39 μL) were sequentially added to a solution of 6-chloro-3-(2-thienyl)imidazo[1,2-b]pyridazine (0.005 g, 21.21 μmol) in dimethyl sulfoxide (0.05 mL) at 20° C. After the addition, the reaction system was heated to 100° C. and stirred for 12 h. After LCMS showed that the starting materials were consumed completely and a product was produced, the reaction solution was separated and purified by Prep-HPLC to give 2-[(1r,4r)-4-[[3-(2-thienyl)imidazo[1,2-b]pyridazin- 6-yl]amino]cyclohexyl]propan-2-ol (0.002 g, yield: 26.45%) as a yellow solid. MS (ESI): m/z 357.1 $[M+H]^+$. $^1H$ NMR (400 MHz, $CDCl_3$) δ7.78 (brs, 1H), 7.59 (dd, J=1.1, 3.7 Hz, 2H), 7.30 (d, J=5.3 Hz, 1H), 7.08 (dd, J=3.7, 5.1 Hz, 1H), 6.33 (d, J=9.0 Hz, 1H), 4.17 (brs, 1H), 3.82-3.67 (m, 1H), 2.36 (d, J=11.0 Hz, 2H), 1.92 (d, J=9.4 Hz, 2H), 1.37-1.18 (m, 5H), 1.18 (s, 6H).

EXAMPLE 7

N-(7-azaspiro[3.5]nonan-2-yl)-3-[3-(trifluoromethyl)phenyl]imidazo[1,2-b]pyridazin-6-amine (compound 16)

16

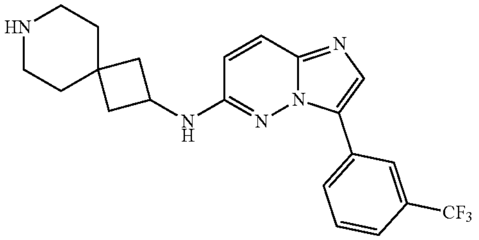

(1) Tert-butyl 2-[[3-[3-(trifluoromethyl)phenyl]imidazo[1,2-b]pyridazin-6-yl]amino]-7-azaspiro[3.5]nonane-7- carboxylate 2-amino-7-boc-7-azaspiro[3.5]nonane (0.66 g, 2.75 mmol) and 6-chloro-3-[3-(trifluoromethyl)phenyl]imidazo[1,2-b]pyridazine (0.6 g, 2.02 mmol) were dissolved in dimethyl sulfoxide (3 mL) at 20° C., and then potassium fluoride (468.42 mg, 8.06 mmol) was added to the reaction solution. After the addition, the reaction solution was heated to 140° C. and stirred at this temperature for 12 h. After TLC showed that the starting materials were completely consumed, the reaction solution was cooled to room temperature and poured into water. The mixed solution was extracted with ethyl acetate. The combined organic phases were concentrated to dryness to give a crude product. The resulting crude product was purified by column chromatography to give tert-butyl 2-[[3-[3-(trifluoromethyl)phenyl]imidazo[1,2-b]pyridazin-6-yl]amino]-7-azaspiro[3.5]nonane-7-carboxylate (0.68 g, yield: 65.24%) as a yellow solid.

(2) N-(7-azaspiro[3.5]nonan-2-yl)-3-[3-(trifluoromethyl)phenyl]imidazo[1,2-b]pyridazin-6-amine Tert-butyl 2-[[3-[3-(trifluoromethyl)phenyl]imidazo[1,2-b]pyridazin-6-yl]amino]-7-azaspiro[3.5]nonane-7-carboxylate (0.68 g, 1.36 mmol) was dissolved in dichloromethane (3 mL) at 25° C., and then hydrochloric acid in dioxane (4 M, 5 mL) was added to the solution. After the addition, the reaction solution was stirred at 25° C. for 0.5 h. After LCMS showed that the starting materials were consumed completely, the reaction solution was adjusted to about pH 8 with aqueous ammonia and then concentrated to dryness to give a crude product. The resulting crude product was purified by Prep-HPLC to give N-(7-azaspiro[3.5]nonan-2-yl)-3-[3-(trifluoromethyl)phenyl]imidazo[1,2-b]pyridazin-6-amine (0.5 g, yield: 91.87%) as a white solid. MS (ESI): m/z 402.1 $[M+H]^+$. $^1H$ NMR (400 MHz, DMSO-$d_6$) δ 8.94 (s, 1H), 8.28 (d, J=6.7 Hz, 1H), 8.07 (s, 1H), 7.79 (d, J=9.7 Hz, 1H), 7.71-7.63 (m, 2H), 7.44 (d, J=6.1 Hz, 1H), 6.72 (d, J=9.7 Hz, 1H), 4.25-4.13 (m, 1H), 2.69-2.62 (m, 2H), 2.60-2.55 (m, 2H), 2.38-2.30 (m, 2H), 1.72-1.61 (m, 2H), 1.56-1.49 (m, 2H), 1.48-1.41 (m, 2H).

EXAMPLE 8

N-(6-azaspiro[3.4]octan-2-ylmethyl)-3-(3-(trifluoromethyl)phenyl)imidazo[1,2-b]pyridazin-6-amine (compound 18)

18

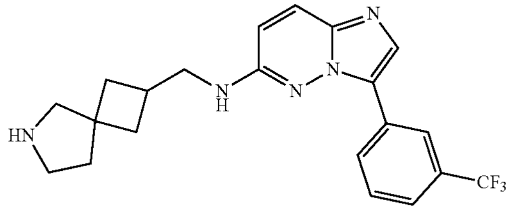

(1) Tert-butyl 2- [[[3-[3-(trifluoromethyl)phenyl]imidazo[1,2-b]pyridazin-6-yl]amino] methyl]-6-azaspiro[3.4]octane-6-carboxylate Referring to the procedures in step (1) of Example 7, 6-chloro-3-[3-(trifluoromethyl)phenyl]imidazo[1,2-b]pyridazine (50 mg, 167.98 μmol) and tert-butyl 2-(aminomethyl)-6-azaspiro[3.4]octane-6-carboxylate (52.48 mg, 218.37 mmol) were used as starting materials to give tert-butyl 2-[[[3-[3-(trifluoromethyl)phenyl]imidazo[1,2-b]pyridazin-6-yl]amino]methyl]-6-azaspiro[3.4]octane-6-carboxylate (45 mg, crude product) as a yellow oil.

(2) N-(6-azaspiro[3.4]octan-2-ylmethyl)-3-(3-(trifluoromethyl)phenyl)imidazo[1,2-b]pyridazin-6-amine Referring to the procedures in step (2) of Example 7, tert-butyl 2-[[[3-[3-(trifluoromethyl)phenyl]imidazo[1,2-b]pyridazin-6-yl]amino]methyl]-6-azaspiro[3.4]octane-6-carboxylate (45 mg, 89.72 μmol) was used as a starting material to give N-(6-azaspiro[3.4]octan-2-ylmethyl)-3-(3-(trifluoromethyl)phenyl)imidazo[1,2- b]pyridazin-6-amine (9.4 mg, yield: 26.10%) as a yellow solid. MS (ESI): m/z 402.0 $[M+H]^+$. $^1H$ NMR (400 MHz, DMSO-$d_6$) δ 8.97 (s, 1H), 8.32 (d, J=7.39 Hz, 1H), 8.09 (s, 1H), 7.79 (d, J=9.66 Hz, 1H), 7.62-7.72 (m, 2H), 7.25 (t, J=5.13 Hz, 1H), 6.76 (d, J=9.66 Hz, 1H), 3.14-3.24 (m, 4H), 2.85-3.00 (m, 3H), 2.56-2.53(m, 1H), 2.00-2.18 (m, 2H), 1.70-1.90 (m, 4H).

EXAMPLE 9

N-(azepan-4-yl)-3-[3-(trifluoromethyl)phenyl]imidazo[1,2-b]pyridazin-6-amine (compound 19)

19

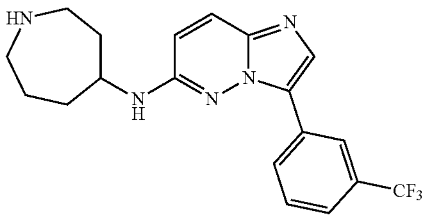

(1) Tert-butyl 4-[[3-[3-(trifluoromethyl)phenyl]imidazo[1,2-b]pyridazin-6-yl]amino]azepane-1-carboxylate Referring to the procedures in step (1) of Example 7, 6-chloro-3-[3-(trifluoromethyl)phenyl]imidazo[1,2-b]pyridazine (50 mg, 167.98 μmol) and tert-butyl azacycloheptane-1-carboxylate (720.0 mg, 3.36 mmol) were used as starting materials to give tert-butyl 4-[[3-[3-(trifluoromethyl)phenyl]imidazo[1,2-b]pyridazin-6-yl]amino]azacycloheptane-1-carboxylate (0.4 g, yield: 50.08%) as a yellow solid.

(2) N-(azepan-4-yl)-3-[3-(trifluoromethyl)phenyl]imidazo[1,2-b]pyridazin-6-amine Referring to the procedures in step (2) of Example 7, tert-butyl 4-[[3-[3-(trifluoromethyl)phenyl]imidazo[1,2-b]pyridazin-6-yl]amino]azepan-1-carboxylate (0.4 g, 105.15 μmol) was used as a starting material to give N-(azepan-4-yl)-3-[3-(trifluoromethyl)phenyl]imidazo[1,2-b]pyridazin-6-amine (0.22 g, yield: 69.67%) as a yellow solid. MS (ESI): m/z 376.1 $[M+H]^+$. $^1H$ NMR (400 MHz, DMSO-$d_6$) δ 8.73 (s, 1H), 8.40 (d, J=7.2 Hz, 1H), 8.08-8.04 (m, 1H), 7.82-7.75 (m, 1H), 7.72-7.63 (m, 2H), 7.14-7.03 (m, 1H), 6.76 (d, J=9.7 Hz, 1H), 3.93 (td, J=3.8, 7.8 Hz, 1H), 2.91-2.76 (m, 3H), 2.73-2.64 (m, 1H), 2.53 (br s, 1H), 2.11-1.94 (m, 2H), 1.79-1.67 (m, 2H), 1.63 (dt, J=4.6, 9.1 Hz, 1H), 1.60- 1.49 (m, 1H).

EXAMPLE 10

2-((1r,4r)-4-4-((3-(5-(trifluoromethyl)thiophen-2-yl)imidazo[1,2-b]pyridazin-6-yl)amino)cyclohexyl)propan-2-ol (compound 20)

20

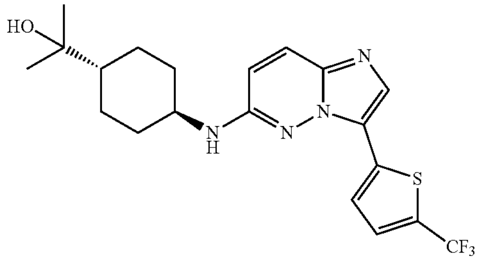

(1) 6-chloro-3[5-(trifluoromethyl)-2-thienyl]imidazo[1,2-b]pyridazine 2-bromo-5-(trifluoromethyl)thiophene (1.81 g, 7.81 mmol), potassium carbonate (1.80 g, 13.02 mmol), and triphenylphosphine (341.59 mg, 1.30 mmol) were sequentially added to a solution of 6-chloroimidazo[1,2-b]pyridazine (1 g, 6.51 mmol) in toluene (10 mL) at 20° C., and then the system was purged 3 times with nitrogen. After purging with nitrogen, palladium acetate (146.19 mg, 651.17 μmol) was added to the reaction system under nitrogen atmosphere. After the addition, the reaction was heated to 120° C. and stirred at 120° C. for 12 h. After TLC showed the reaction was completed and LCMS showed that a product was produced, the reaction solution was cooled to room temperature and poured into water. The mixed solution was extracted with ethyl acetate. The combined organic phases were dried over anhydrous sodium sulfate and filtered, and the filtrate was concentrated to dryness to give 6-chloro-3-[5-(trifluoromethyl)-2-thienyl]imidazo[1,2-b]pyridazine (1.8 g, crude product) as a yellow solid.

(2) 2-((1r,4r)-4-((3-(5-(trifluoromethypthiophen-2-yl)imidazo[1,2-b]pyridazin-6-yl)amino)cyclohexyl)propan-2-ol 2-((1r,4r)-4-aminocyclohexyl)propan-2-ol (310.68 mg, 1.98 mmol), cesium fluoride (500.18 mg, 3.29 mmol), and N,N-diisopropylethylamine (425.56 mg, 3.29 mmol) were sequentially added to a solution of 6-chloro-30[5-(trifluoromethyl)-2-thienyl]imidazo[1,2-b]pyridazine (0.5 g, 1.65 mmol) in dimethyl sulfoxide (5 mL) at 20° C. After the addition, the system was heated to 100° C. and stirred at 100° C. for 12 h. After TLC showed the reaction was completed and LCMS showed that a product was produced, the reaction solution was cooled to room temperature and poured into water. The mixed solution was extracted with ethyl acetate. The organic phase was washed with saturated brine, dried over anhydrous sodium sulfate, and filtered, and then the filtrate was concentrated to dryness to give a crude product. The resulting crude product was purified by Prep-HPLC to give 2-((1r,4r)-4-((3-(5-(trifluoromethypthiophen-2-yl)imidazo[1,2-b]pyridazin-6-yl)amino)cyclohexyl)propan-2-ol (0.18 g, yield: 25.76%) as a white solid. MS (ESI): m/z 425.1 $[M+H]^+$. $^1H$ NMR (400 MHz, DMSO-$d_6$) δ 8.14 (s, 1H), 7.92-7.70 (m, 3H), 7.28 (d, J=6.8 Hz, 1H), 6.73 (d, J=9.7 Hz, 1H), 4.09 (s, 1H), 3.67 (brs, 1H), 2.27 (brs, 2H), 1.94 (brs, 2H), 1.30 (d, J=9.0 Hz, 1H), 1.25-1.14 (m, 4H), 1.07 (s, 6H).

EXAMPLE 11

(1S,3R)-3-[[3-[3-(trifluoromethyl)phenyl]imidazo[1,2-b]pyridazin-6-yl]amino]cycloheptanol (compound 21)

21

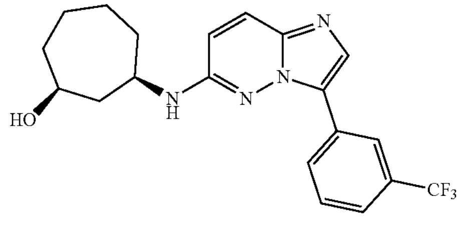

6-chloro-3-[3-(trifluoromethyl)phenyl]imidazo[1,2-b]pyridazine (50 mg, 211.26 μmol) and (1S,3R)-3-aminocycloheptanol (36 mg, 217.31 μmol) were dissolved in dimethyl sulfoxide (1 mL) at 25° C. in an 8 mL reaction flask, followed by the addition of N,N-diisopropylethylamine (68.26 mg, 528.14 μmol) and cesium fluoride (80.22 mg, 528.14 μmol). After the addition, the reaction solution was heated to 140° C. and reacted at this temperature for 12 h. After LCMS showed that the starting materials were consumed completely, the reaction solution was cooled to room temperature and poured into water. The mixed solution was extracted with ethyl acetate. The combined organic phases were concentrated to dryness to give a crude product. The crude product was purified by Prep-HPLC to give (1S,3R)-3-[[3-[3-(trifluoromethyl)phenyl]imidazo[1,2-b]pyridazin-6-yl]amino]cycloheptanol (7 mg, yield: 8.49%) as a white solid. MS (ESI): m/z 391.2 [M+H]$^+$. $^1$H NMR (400 MHz, DMSO-$d_6$) δ 8.71 (s, 1H), 8.42 (d, J=7.4 Hz, 1H), 8.06 (s, 1H), 7.78 (d, J=9.8 Hz, 1H), 7.72-7.64 (m, 2H), 7.10 (d, J=7.5 Hz, 1H), 6.72 (d, J=9.8 Hz, 1H), 4.49 (d, J=4.1 Hz, 1H), 3.88-3.67 (m, 2H), 2.16 (d, J=12.3 Hz, 1H), 2.01-1.81 (m, 2H), 1.69-1.40 (m, 7H).

EXAMPLE 12 cis-4-[[3-[3-(trifluoromethyl)phenyl]imidazo[1,2-b]pyridazin-6-yl]amino]cycloheptanol (compound 23)

23

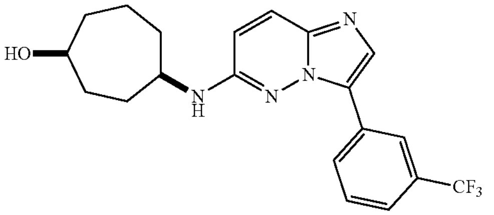

Referring to the procedures in Example 11, cis-4-aminocycloheptanol hydrochloride (36 mg, 217.32 μmol) and 5-(6-chloroimidazo[1,2-b]pyridazin-3-yl)thiazole (50 mg, 211.26 μmol) were used as starting materials to give cis-4-[[3-[3-(trifluoromethyl)phenyl]imidazo[1,2-b]pyridazin-6-yl]amino]cycloheptanol (16.6 mg, yield: 20.13%) as a white solid. MS (ESI): m/z 391.2 [M+H]$^+$. $^1$H NMR (400 MHz, $CDCl_3$) δ 8.68 (s, 1H), 8.18-8.10 (m, 1H), 7.89 (s, 1H), 7.70 (d, J=9.7 Hz, 1H), 7.62-7.55 (m, 2H), 6.46 (d, J=9.7 Hz, 1H), 4.50 (d, J=7.5 Hz, 1H), 4.18-4.02 (m, 2H), 2.21-2.11 (m, 1H), 2.09-2.00 (m, 1H), 1.99-1.92 (m, 2H), 1.90-1.76 (m, 3H), 1.68-1.63 (m, 1H), 1.53-1.39 (m, 2H).

EXAMPLE 13

N-(6-azas piro [3.4]octan-2-yl)-3-(3-(trifluoromethyl)phenyl)imidazo[1,2-b]pyridazin-6-amine (compound 24)

24

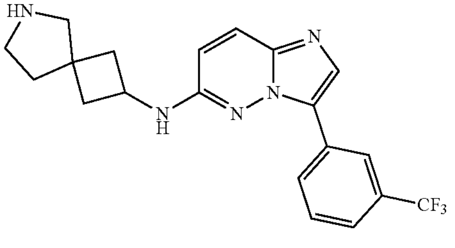

(1) Tert-butyl 2-[[3-[3-(trifluoromethyl)phenyl]imidazo[1,2-b]pyridazin-6-yl]amino]-6-azaspiro[3.4]octane-6- carboxylate Referring to the procedures in step (1) of Example 7, 6-chloro-3-[3-(trifluoromethyl)phenyl]imidazo[1,2-b]pyridazine (0.1 g, 335.95 μmol) and tert-butyl 2-amino-6-azaspiro[3.4]octane-6-carboxylate (98.84 mg, 436.74 μmol) were used as starting materials to give tert-butyl 2-[[3-[3-(trifluoromethyl)phenyl]imidazo[1,2-b] pyridazin-6-yl]amino]-6-azaspiro[3.4]octane-6-carboxylate (0.12 g, crude product) as a yellow oil.

(2) N-(6-azaspiro [3.4]octan-2-yl)-3-(3 -(trifluoromethyl)phenyl)imidazo[1,2-b]pyridazin-6-amine Referring to the procedures in step (2) of Example 7, tert-butyl 2-[[3-[3-(trifluoromethyl)phenyl]imidazo[1,2-b]pyridazin-6-yl] amino]-6-azaspiro [3.4]octane-6-carboxylate (60 mg, 123.07 μmol) was used as a starting material to give N-(6-azaspiro[3.4]octan-2-yl)-3-(3-(trifluoromethyl)phenyl)imidazo[1,2-b]pyridazin-6-amine (5.1 mg, yield: 10.70%) as a yellow solid. MS (ESI): m/z 388.2 [M+H]$^+$. $^1$H NMR (400 MHz, DMSO-$d_6$) δ 8.88 (s, 1H), 8.32-8.39 (m, 1H), 8.08-8.12 (m, 1H), 7.79-7.86 (m, 1H), 7.65-7.74 (m, 2H), 7.53 (d, J=5.99 Hz, 1H), 6.73 (d, J=9.78 Hz, 1H), 4.13-4.24 (m, 1H), 3.49-3.59 (m, 1H), 3.12 (s, 2H), 3.06 (t, J=7.15 Hz, 2H), 2.56 (d, J=3.18 Hz, 2H), 2.00-2.08 (m, 2H), 1.92 (t, J=7.34 Hz, 2H).

EXAMPLE 14

[(2R,5S)-5-[[3-[3-(trifluoromethyl)phenyl]imidazo[1,2-b]pyridazin-6-yl]amino]tetrahydropyran-2-yl]methanol (compound 25)

25

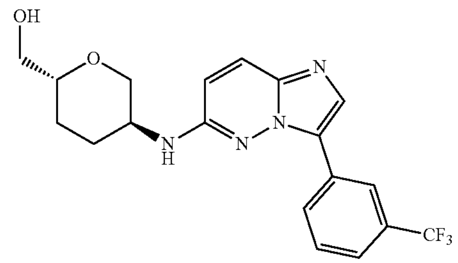

(1) Methyl (2S)-2-(tert-butoxy carbonylamino)hex-5-enoate

The activated zinc powder (44.70 g, 683.6 mmol) and N,N-dimethylformamide (200 mL) were added to reaction flask 1. Then, the reaction system was cooled to 0° C., and a solution of methyl (2R)-2-(tert-butoxycarbonylamino)-3-iodopropionate (45 g, 136.72 mmol) in N,N-dimethylformamide (50 mL) was added dropwise. The reaction system was heated to 20° C., stirred for one hour, and left to stand, and then the supernatant was pipetted for later use. 3-bromopropene (28.12 g, 232.4 mmol) was added to N,N-dimethylformamide (200 mL) containing cuprous bromide (35.30 g, 246.1 mmol) at 20° C. in reaction flask 2. The reaction system was cooled to −15° C., and the reaction supernatant in reaction flask 1 was added dropwise. Then, the reaction system was heated to 20° C. and stirred for 12 h. After TLC (petroleum ether/ethyl acetate=3/1) showed that the starting materials were consumed completely and a new spot was formed, that is, a product was formed, 500 mL of ethyl acetate was added to the reaction system. The reaction system was successively stirred for 15 min, followed by the addition of 500 mL of water for liquid separation. The organic phase was sequentially washed with a 1 M sodium thiosulfate solution (300 mL) and water (300 mL), dried over anhydrous sodium sulfate, filtered, and concentrated completely to give a crude product. The crude product was purified by column chromatography (petroleum ether/ethyl acetate=100/1 to 100% ethyl acetate) to give methyl (2S)-2-(tert-butoxycarbonylamino)hex-5-enoate (20 g, yield: 60.12%) as a colorless oil.

(2) Tert-butyl N-[(1S)-1-(hydroxymethyl)pent-4-enyl]carbamate

Lithium borohydride (1.79 g, 82.20 mmol) was added in portions to tetrahydrofuran (100 mL) at 20° C. under nitrogen atmosphere, and a solution of methyl (2S)-2-(tert-butoxycarbonylamino)hex-5-enoate (20 g, 82.20 mmol) in tetrahydrofuran (60 mL) was slowly added dropwise. Then, the reaction system was stirred at 20° C. for 12 h. After TLC (petroleum ether/ethyl acetate=5/1) showed that the starting materials were consumed completely and a new spot was formed, that is, a product was formed, the reaction was quenched by adding 500 mL of water to the reaction solution. The mixed solution was extracted with ethyl acetate (300 mL×2). The organic phase was washed with 500 mL of saturated brine, dried over anhydrous sodium sulfate, and concentrated under reduced pressure to remove the solvent to give tert-butyl N-[(1S)-1-(hydroxymethyl) pent-4-enyl]carbamate (12 g, yield: 67.81%) as a colorless oil, and the resulting crude product was directly used in the next step. 1H NMR (400 MHz, $CDCl_3$) δ 5.74 (tdd, J=6.6, 10.3, 17.0 Hz, 1H), 5.01-4.88 (m, 2H), 4.59 (brs, 1H), 3.68-3.55 (m, 2H), 3.55-3.41 (m, 1H), 2.11-2.01 (m, 2H), 1.61-1.41 (m, 3H), 1.38 (s, 9H).

(3) Tert-butyl N-[(1S)-1-(hydroxymethyl)-3-(oxiran-2-yl) propyl]carbamate

A solution of tert-butyl N-[(1S)-1-(hydroxymethylpent-4-enyl]carbamate (10 g, 46.45 mmol) in dichloromethane (150 mL) and a solution of potassium dihydrogen phosphate solution (18.96 g, 139.35 mmol) in water (200 mL) were mixed at 20° C., followed by the addition of m-chloroperoxybenzoic acid (8.02 g, 46.45 mmol) at 20° C. The reaction system was stirred for 12 h. After TLC (petroleum ether/ethyl acetate=1/1) showed that the starting materials were consumed completely and a new spot was formed, that is, a product was formed, the reaction solution was subjected to liquid separation to give an organic phase, and the aqueous phase was extracted with dichloromethane (100 mL×2). The organic phases were combined and concentrated under reduced pressure to remove the solvent to give a crude product. The crude product was purified by column chromatography (petroleum ether/ethyl acetate=100/1 to 100% ethyl acetate) to give tert-butyl N-[(1S)-1-(hydroxymethyl)-3-(oxiran-2-yl)propyl]carbamate (4 g, yield: 37.23%) as a yellow oil.

(4) Tert-butyl N-[(3S,6R)-6-(hydroxymethyl)tetrahydropyran-3-yl]carbamate

Camphor-10-sulfonic acid (97.40 mg, 389.1 μmol) was added to a solution of tert-butyl N-[(1S)-1-(hydroxymethyl)-3-(oxiran-2-yl)propyl]carbamate (0.9 g, 3.89 mmol) in dichloromethane (9 mL) at 20° C. The reaction system was stirred at 20° C. for 12 h. After TLC (petroleum ether/ethyl acetate=0/1) showed that the starting materials were consumed completely and a new spot was formed, that is, a product was formed, the reaction solution was concentrated to remove the solvent to give a crude product, which was then purified by column chromatography (petroleum ether/ethyl acetate=100/1 to 100% ethyl acetate) to give tert-butyl N-[(3S,6R)-6-(hydroxymethyptetrahydropyran-3-yl]carbamate (0.28 g, yield: 31.11%) as a white solid. 1H NMR (400 MHz, $CDCl_3$) δ 4.22 (brs, 1H), 4.06-4.02 (m, 1H), 3.58-3.50 (m, 2H), 3.47-3.42 (m, 1H), 3.48-3.42 (m, 1H), 3.33-3.25 (m, 1H), 2.95 (t, J=10.6 Hz, 1H), 2.04 (d, J=12.3 Hz, 1H), 1.88 (d, J=12.7 Hz, 1H), 1.38 (d, J=5.4 Hz, 10H), 1.29-1.21 (m, 1H).

(5) [(2R,5S)-5 -aminotetrahy dropyran-2-yl]methanol hydrochloride

Tert-butyl N-[(3S,6R)-6-(hydroxymethyl)tetrahydropyran-3-yl]carbamate (0.3 g, 1.30 mmol) was added to hydrochloric acid in dioxane (3 mL) at 20° C. The reaction system was stirred at 20° C. for 2 h. After TLC (petroleum ether/ethyl acetate=0/1) showed that the starting materials were consumed completely and a new spot was formed, that is, a product was formed, the reaction solution was concentrated under reduced pressure to remove the solvent to give [(2R,5S)-5-aminotetrahydropyran-2-yl]methanol hydrochloride (0.2 g, yield: 91.98%) as a white solid, and the resulting crude product was directly used in the next step.

(6) [(2R,5S)-5-[[3-[3-(trifluoromethyl)phenyl]imidazo[1,2-b]pyridazin-6-yl]amino]tetrahydropyran-2-yl]methanol Referring to the procedures in step (1) of Example 7, [(2R5S)-5-aminotetrahydropyran-2-yl]methanol hydrochloride (0.10 g, 760 μmol) and 6-chloro-3-[3-(trifluoromethyl) phenyl]imidazo[1,2-b]pyridazine (250 mg, 840.0 μmol) were used as starting materials to give [(2R,5S)-5-[[3-[3-(trifluoromethyl)phenyl]imidazo[1,2-b]pyridazin-6-yl] amino]tetrahydropyran-2-yl]methanol (0.0054 g, yield: 2.84%) as a white solid. MS (ESI): m/z 393.1 $[M+H]^+$. $^1$H NMR (400MHz, DMSO-$d_6$) δ 8.89 (s, 1H), 8.37 (d, J=7.5 Hz, 1H), 8.14 (s, 1H), 7.87 (d, J=9.9 Hz, 1H), 7.81-7.67 (m, 2H), 7.34 (d, J=6.6 Hz, 1H), 7.03 (d, J=9.8 Hz, 1H), 4.68 (t, J=5.4 Hz, 1H), 4.12 (d, J=11.1 Hz, 1H), 3.90 (brs, 1H), 3.69 (d, J=10.6 Hz, 1H), 3.57-3.49 (m, 3H), 2.18 (d, J=13.7 Hz, 1H), 1.94-1.77 (m, 1H), 1.73-1.52 (m, 2H).

EXAMPLE 15

N-(7-methyl-7-azaspiro[3.5]nonan-2-yl)-3-(3-(trifluoromethyl)phenyl)imidazo[1,2-b]pyridazin-6-amine (compound 26)

26

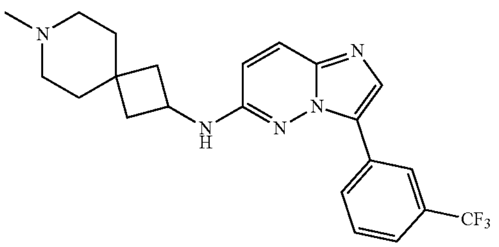

(1) Tert-butyl 2-((3-(3-(trifluoromethyl)phenyl)imidazo[1,2-b]pyridazin-6-yl)amino)-7-azaspiro[3.5]nonane-7-carboxylate Referring to the procedures in step (1) of Example 7, 2-amino-7-Boc-7-azaspiro[3.5]nonane (0.11 g, 457.68 μmol) and 6-chloro-3-[3-(trifluoromethyl)phenyl]imidazo [1,2-b]pyridazine (0.1 g, 335.95 μmol) were used as starting materials to give tert-butyl 2-[[3-[3-(trifluoromethyl)phenyl]imidazo[1,2-b]pyridazin-6-yl]amino]-7- azaspiro[3.5] nonane-7-carboxylate (75 mg, yield: 44.51%) as a yellow solid.

(2) N-(7-methyl-7-azaspiro[3.5]nonan-2-yl)-3-(3-(trifluoromethyl)phenyl)imidazo[1,2-b]pyridazin-6-amine Tert-butyl 2-[[3-[3-(trifluoromethyl)phenyl]imidazo[1,2-b]pyridazin-6-yl]amino]-7-azaspiro[3.5]nonane-7-carboxylate (40 mg, 79.75 μmol) was dissolved in THF (1 mL) at 25° C., followed by the addition of lithium tetrahydroaluminium (7.5 mg, 197.61 μmol) at 25° C. The reaction solution was heated to 30° C. and stirred at 30° C. for 16 h. After LCMS showed that the starting materials were consumed completely, the reaction was quenched by adding sodium sulfate decahydrate to the reaction solution at 25° C. The mixed solution was stirred at 25° C. for 4 h and filtered. The filter cake was rinsed with ethyl acetate, and the filtrate was concentrated to give a crude product. The resulting crude product was purified by Prep-HPLC to give N-(7-methyl-7-azaspiro[3.5]nonan-2-yl)-3-(3-(trifluoromethyl)phenyl)imidazo[1,2-b]pyridazin-6-amine (9 mg, yield: 27.16%) as a light yellow gum. MS (ESI): m/z 416.2 $[M+H]^+$. $^1H$ NMR (400 MHz, $CD_3OD$) δ 8.91 (s, 1H), 8.24-8.15 (m, 1H), 7.93 (s, 1H), 7.71-7.61 (m, 3H), 6.75 (d, J=9.6 Hz, 1H), 4.32 (t, J=7.9 Hz, 1H), 3.55-3.45 (m, 1H), 3.23-3.10 (m, 1H), 2.56-2.37 (m, 4H), 2.28 (s, 3H), 1.84-1.66 (m, 6H).

EXAMPLE 16

N-(1-methylazacycloheptan-4-yl)-3-[3-(trifluoromethyl)phenyl]imidazo[1,2-b]pyridazin-6-amine (compound 27)

27

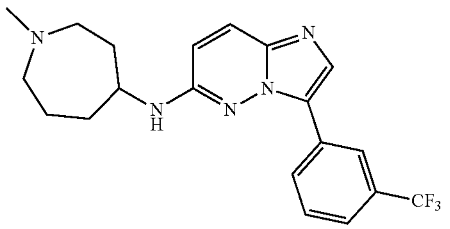

The compound was obtained by further methylation of compound 19.

Acetic acid (399.92 μpg, 6.66 μmol) was added dropwise to a mixed solution of N-(azepan-4-yl)-3-[3-(trifluoromethyl)phenyl]imidazo[1,2-b]pyridazin-6-amine (0.025 g, 66.60 μmol) and paraformaldehyde (12 mg, 99.90 μmol) in dichloromethane (0.3 mL) and methanol (0.3 mL) at 25° C. The reaction system was stirred at 25° C. for 30 min. Then, sodium cyanoborohydride (16.74 mg, 266.39 μmol) was added to the reaction solution. The reaction system was stirred at 25° C. for 12 h. After LCMS showed that the starting materials were consumed completely and a product was produced, the reaction mixture was concentrated under reduced pressure to remove the solvent to give a crude product. The resulting crude product was dissolved in methanol and filtered, and the resulting filtrate was directly purified by Prep-HPLC to give N-(1-methylazepan-4-yl)-3-[3-(trifluoromethyl)phenyl]imidazo[1,2-b]pyridazin-6-amine (11.9 mg, yield: 45.89%) as a yellow oil. MS (ESI): m/z 390.1 $[M+H]^+$. $^1H$ NMR (400 MHz, $CDCl_3$) δ 8.55 (s, 1H), 8.07 (t, J=3.8 Hz, 1H), 7.78 (s, 1H), 7.59 (d, J=9.5 Hz, 1H), 7.48 (d, J=4.9 Hz, 2H), 6.41 (d, J=9.6 Hz, 1H), 4.87 (d, J=8.0 Hz, 1H), 4.17 (tq, J=4.1, 7.9 Hz, 1H), 2.76-2.58 (m, 2H), 2.51-2.41 (m, 2H), 2.33 (s, 3H), 2.10-1.99 (m, 1H), 1.92-1.82 (m, 3H), 1.78-1.57 (m, 2H).

EXAMPLE 17

N-(azepan-4-yl)-3-[5-(trifluoromethyl)-2-thienyl]imidazo[1,2-b] pyrid azin-6-amine (compound 28)

28

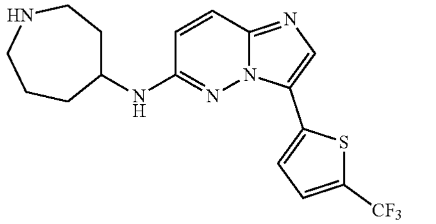

(1) Tert-butyl 4[[3-[5-(trifluoromethyl)-2-thienyl]imidazo[1,2-b]pyridazin-6-yl]amino]azepane-1-carboxylate Referring to the procedures in step (2) of Example 10, 6-chloro-3-[5-(trifluoromethyl)-2-thienyl]imidazo[1,2-b]pyridazine (0.22 g, 724.42 μmol) and tert-butyl 4-aminoazepane-1-carboxylate (186.30 mg, 869.31 μmol) were used as starting materials to give tert-butyl 4-[[3-[5-(trifluoromethyl)-2-thienyl]imidazo[1,2-b]pyridazin-6-yl]amino]azepane-1-carboxylate (0.26 g, yield: 74.53%) as a yellow solid.

(2) N-(azepan-4-yl)-3-[5-(trifluoromethyl)-2-thienyl]imidazo[1,2-b]pyridazin-6-amine Referring to the procedures in step (2) of Example 7, tert-butyl 4-[[3-[5-(trifluoromethyl)-2-thienyl]imidazo[1,2-b]pyridazin-6-yl]amino]azepan-1-carboxylate (0.25 g, 519.17 μmol) was used as a starting material to give N-(azepan-4-yl)-3-[5-(trifluoromethyl)-2-thienyl]imidazo[1,2-b]pyridazin-6-amine (0.12 g, yield: 60.60%) as a yellow solid. MS (ESI): m/z 382.0 $[M+H]^+$. $^1H$ NMR (400 MHz, $CD_3OD$) δ 7.98 (s, 1H), 7.70-7.65 (m, 2H), 7.58 (dd, J=1.1, 4.0 Hz, 1H), 6.77 (d, J=9.8 Hz, 1H), 4.17-4.06 (m, 1H), 3.21-3.11 (m, 1H), 3.09-2.92 (m, 3H), 2.43-2.26 (m, 2H), 2.00-1.70 (m, 4H).

EXAMPLE 18

4-[[3-[5-(trefluoromethyl)-2-thienyl]imidazo[1,2-b]pyridazin-6-yl]amino]bicyclo [2.2.2] octan-1-ol (compound 29)

29

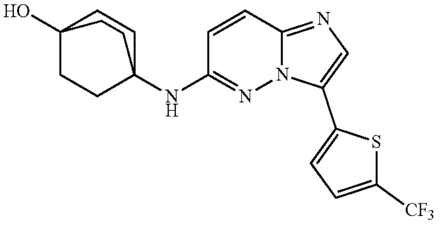

Referring to the procedures in step (2) of Example 10, 6-chloro-3-[5-(trifluoromethyl)-2-thienyl]imidazo[1,2-b]pyridazine (0.03 g, 98.78 μmol) and 4-aminobicyclo[2.2.2]

oct-1-ol hydrochloride (21.06 mg, 118.54 μmol) were used as starting materials to give 4-[[3-[5-(trifluoromethyl)-2-thienyl]imidazo[1,2-b]pyridazin- 6-yl]amino]bicyclo[2.2.2]octan-1-ol (10 mg, yield: 24.79%) as a yellow solid. MS (ESI): m/z 409.0 $[M+H]^+$. $^1H$ NMR (400 MHz, DMSO-$d_6$) δ 8.13 (s, 1H), 7.81-7.69 (m, 3H), 6.89 (s, 1H), 6.76 (d, J=9.8 Hz, 1H), 4.38 (s, 1H), 2.25-2.17 (m, 6H), 1.76-1.66 (m, 6H).

EXAMPLE 19

N-(7-cyclopropyl-7-azaspiro [3.5]nonan-2-yl)-3-(3-(trifluoromethyl)phenyl)imidazo[1,2-b]pyridazin-6-amine (compound 30)

30

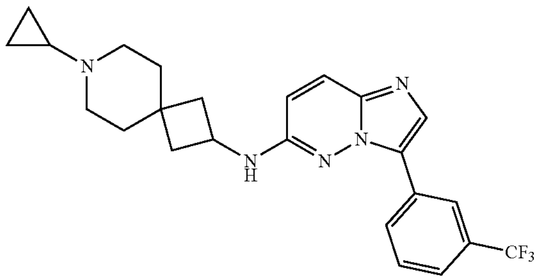

N-(7-azaspiro[3.5]non-2-yl)-3-(3-(trifluoromethyl)phenyl)imidazo[1,2-b]pyridazin-6-amine (60 mg, 149.47 μmol), sodium cyanoborohydride (56.36 mg, 896.80 μmol), and acetic acid (53.85 mg, 896.80 μmol, 51.29 μL) were added to a solution of 1-ethoxy-1-trimethylsilylcyclopropane (156.32 mg, 896.80 μmol, 180.30 μL) in methanol (4 mL) at 25° C. After the addition, the reaction solution was heated to 60° C. and stirred at 60° C. for 12 h. After LCMS showed that the starting materials were consumed completely, the reaction solution was directly purified by Prep-HPLC without treatment to give N-(7-azaspiro [3.5]non-2-yl)-3-(3 -(trifluoromethyl)phenyl)imidazo[1,2-b]pyridazin-6-amine (27 mg, yield: 46.28%) as a white solid. MS (ESI): m/z 442.3 $[M+H]^+$. $^1H$ NMR (400 MHz, $CDCl_3$) δ 8.70 (s, 1H), 8.00 (d, J=6.8 Hz, 1H), 7.81 (s, 1H), 7.62 (d, J=9.6 Hz, 1H), 7.55-7.44 (m, 2H), 6.39 (d, J=9.6 Hz, 1H), 4.46 (d, J=6.0 Hz, 1H), 4.32-4.20 (m, 1H), 2.65-2.34 (m, 6H), 1.72-1.54 (m, 7H), 0.38 (brs, 4H).

EXAMPLE 20

N-(7-azaspiro[3.5]nonan-2-yl)-3-[5-(trifluoromethyl)-2-thienyl]imidazo[1,2-b]pyridazin-6-amine (compound 31)

31

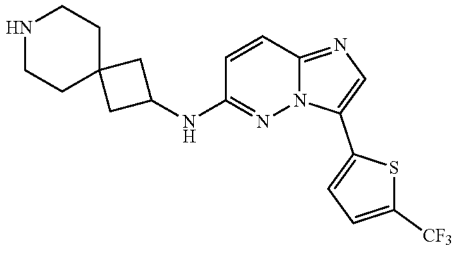

(1) Tert-butyl 2-[[3-[5-(trifluoromethyl)-2-thienyl]imidazo[1,2-b]pyridazin-6-yl]amino]-7-azaspiro[3.5]nonane-7- carboxylate Referring to the procedures in step (2) of Example 10, 6-chloro-3-[5-(trifluoromethyl)-2-thienyl]imidazo[1,2-b]pyridazine (220 mg, 724.42 μmol) and tert-butyl 2-amino-7-azaspiro[3.5]nonane-7-carboxylate (208.93 mg, 869.31 μmol) were used as starting materials to give tert-butyl 2-[[3-[5-(trifluoromethyl)-2-thienyl]imidazo[1,2-b]pyridazin-6-yl]amino]-7-azaspiro[3.5]nonane-7- carboxylate (0.2 g, yield: 54.39%) as a yellow solid.

(2) N-(7-azaspiro[3.5]nonan-2-yl)-3-[5-(trifluoromethyl)-2-thienyl]imidazo[1,2-b]pyridazin-6-amine Referring to the procedures in step (2) of Example 7, tert-butyl 2-[[3-[5-(trifluoromethyl)-2-thienyl]imidazo[1,2-b]pyridazin-6-yl]amino]-7-azaspiro[3.5]nonane-7-carboxylate (0.2 g, 394.03 μmol) was used as a starting material to give N-(7-azaspiro[3.5]nonan-2-yl)-3-[5-(trifluoromethyl)-2-thienyl]imidazo[1,2-b]pyridazin-6-amine (0.134 g, yield: 83.46%) as a white solid. MS (ESI): m/z 408.1 $[M+H]^+$. $^1H$ NMR (400 MHz, DMSO-$d_6$) δ 8.16 (s, 1H), 7.88-7.72 (m, 4H), 6.76 (d, J=9.7 Hz, 1H), 4.38-4.27 (m, 1H), 3.04 (brs, 2H), 2.97-2.90 (m, 2H), 2.55 (brs, 2H), 1.87-1.69 (m, 6H).

EXAMPLE 21

6-(((1r,4r)-4-(2-hydroxypropan-2-yl)cyclohexyl)amino)-3-(3-(trifluoromethyl)phenyl)imidazo[1,2-b]pyridazine-2-carboxylic acid (compound 42)

42

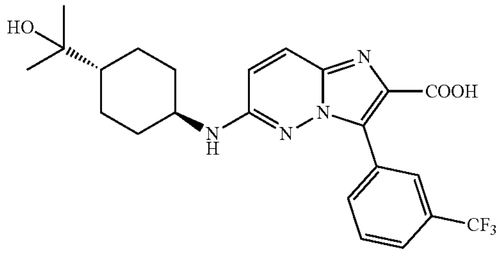

(1) Ethyl 3-bromo-6-chloroimidazo[1,2-b]pyridazine-2-carboxylate

Ethyl 6-chloroimidazo[1,2-b]pyridazine-2-carboxylate (2 g, 8.8 mmol) and NBS (1.9 g, 10.6 mmol) were dissolved in dichloromethane (20 mL). The reaction system was stirred at 40° C. for 48 h. A small amount of water was added. The mixed solution was extracted with ethyl acetate (40 mL×2), followed by liquid separation. The organic phase was dried over anhydrous sodium sulfate, filtered, concentrated under reduced pressure, and purified by reverse phase column chromatography to give ethyl 3-bromo-6-chloroimidazo[1,2-b]pyridazine-2-carboxylate (2.3 g, yield: 88%) as a white solid. MS (ESI): m/z 304.3 $[N+H]^+$.

(2) Referring to the procedures in step (2) of Example 1, ethyl 3-bromo-6-chloroimidazo[1,2-b]pyridazine-2-carboxylate (300 mg, 0.9 mmol) and (3-(trifluoromethyl)phenyl)boronic acid (131 mg, 0.6 mmol) were used as starting materials to give ethyl 6-chloro-3-(3-(trifluoromethyl)phenyl)imidazo[1,2-b]pyridazine-2-carboxylate (60 mg, yield: 16%) as a yellow solid.

(3) Referring to the procedures in step (3) of Example 1, ethyl 6-chloro-3-(3-(trifluoromethyl)phenyl)imidazo[1,2-b]pyridazine-2-carboxylate (60 mg, 0.4 mmol) and 2-((1r,4r)-

4-aminocyclohexyl)propanol (50 mg, 0.4 mmol) were used as starting materials to give 6-(((1r,4r)-4-(2-hydroxypropan-2-yl)cyclohexyl)amino)-3-(3- (trifluoromethyl)phenyl)imidazo[1,2-b]pyridazine-2-carboxylic acid (15.8 mg, yield: 10%) as a white solid. MS (ESI): m/z 463.3 $[M+H]^+$. $^1H$ NMR (400 MHz, DMSO-$d_6$) δ 8.14 (s, 1H), 8.01 (d, J=6.8 Hz, 1H), 7.76 (d, J=7.6 Hz, 2H), 7.67 (t, J=8.0 Hz, 1H), 7.09 (d, J=7.2 Hz, 1H), 6.78 (d, J=9.2 Hz, 1H), 4.01 (s, 1H), 2.03 (d, J=9.8 Hz, 2H), 1.78 (d, J=11.6 Hz, 2H), 1.23-0.90 (m, 11H).

EXAMPLE 22

(1R,3R)-3-((3-(3-(trifluoromethyl)phenyl)imidazo[1,2-b]pyridazin-6-yl)amino)cycloheptanol (compound 44)

44

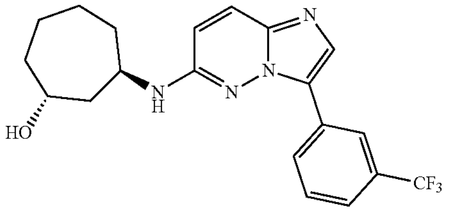

Referring to the procedures in step (2) of Example 10, (1R,3R)-3-aminocycloheptanol hydrochloride (35 mg, 211.28 μmol) and 6-chloro-3-[3-(trifluoromethyl)phenyl]imidazo[1,2-b]pyridazine (62.89 mg, 211.28 μmol) were used as starting materials to give (1R,3R)-3-((3-(3-(trifluoromethyl)phenyl)imidazo[1,2-b]pyridazin-6- yl)amino)cycloheptanol (8.1 mg, yield: 9.82%) as a yellow solid. MS (ESI): m/z 391.1 $[M+H]^+$. $^1H$ NMR (400 MHz, DMSO-$d_6$) δ 8.74 (s, 1H), 8.43 (d, J=7.46 Hz, 1H), 8.06 (s, 1H), 7.77 (d, J=9.66 Hz, 1H), 7.63-7.73 (m, 2H), 7.07 (d, J=7.34 Hz, 1H), 6.76 (d, J=9.66 Hz, 1H), 4.41 (d, J=3.79 Hz, 1H), 4.01-4.09 (m, 1H), 3.86 (dd, J=8.68, 3.67 Hz, 1H), 2.02-2.12 (m, 2H), 1.82-1.96 (m, 2H), 1.65-1.79 (m, 2H), 1.30 -1.56 (m, 4H).

EXAMPLE 23

(1R,4R)-4-((3-(3-(trifluoromethyl)phenyl)imidazo[1,2-b]pyridazin-6-yl)amino)cycloheptanol (compound 45)

45

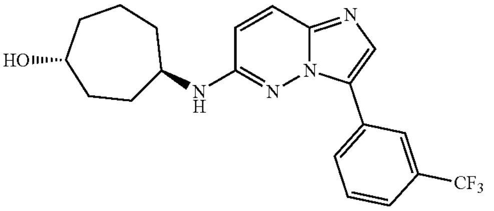

Referring to the procedures in step (1) of Example 7, (1R,4R)-4-aminocycloheptanol hydrochloride (28.90 mg, 174.45 μmol) and 6-chloro-3-[3-(trifluoromethyl)phenyl]imidazo[1,2-b]pyridazine (41.29 mg, 174.45 μmol) were used as starting materials to give 4-[[3-[3-(trifluoromethyl)phenyl]imidazo[1,2-b]pyridazin-6-yl]amino]cycloheptanol 11 mg, yield: 16.15%) as a white solid. MS (ESI): m/z 391.2 $[M+H]^+$. $^1H$ NMR (400 MHz, $CD_3OD$) δ 8.60 (s, 1H), 8.38-8.29 (m, 2H), 7.93 (d, J=9.9 Hz, 1H), 7.87-7.74 (m, 2H), 7.19 (d, J=9.8 Hz, 1H), 4.03-3.97 (m, 1H), 3.92-3.78 (m, 1H), 2.21-2.06 (m, 2H), 2.05-1.93 (m, 2H), 1.73-1.49 (m, 6H).

EXAMPLE 24

[(2S,5R)-5-[[3-[5-(trifluoromethyl)-2-thienyl]imidazo[1,2-b]pyridazin-6-yl]amino]tetrahydropyran-2-yl]methanol (compound 46)

46

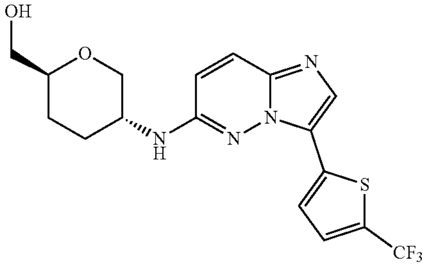

Referring to the procedures in step (1) of Example 7, [(2S,5R)-5-aminotetrahydropyran-2-yl]methanol hydrochloride (Example 28, 30.00 mg, 228.71 μmol) and 6chloro-3-[5-(trifluoromethyl)-2-thienyl]imidazo[1,2-b]pyridazine (76.40 mg, 251.58 μmol) were used as starting materials to give [(2S,5R)-5-[[3-[5-(trifluoromethyl)-2-thienyl]imidazo[1,2-b]pyridazin-6-yl]amino]tetrahydropyran-2-yl]methanol (0.005 g, yield: 5.49%) as a white solid. MS (ESI): m/z 399.0 $[M+H]^+$. $^1H$ NMR (400 MHz, DMSO-$d_6$) δ 8.16 (s, 1H), 7.84 (d, J=9.7 Hz, 1H), 7.81-7.75 (m, 2H), 7.26 (d, J=6.9 Hz, 1H), 6.74 (d, J=9.8 Hz, 1H), 4.72-4.61 (m, 1H), 4.17 (d, J=8.5 Hz, 1H), 3.92 (s, 1H), 3.46-3.39 (m, 1H), 3.30-3.23 (m, 2H), 3.17 (t, J=10.6 Hz, 1H), 1.82 (d, J=11.3 Hz, 1H), 1.53-1.31 (m, 2H), 1.15 (s, 1H).

EXAMPLE 25

[(2R,5S)-5-[[3-[5-(trifluoromethyl)-2-thienyl]imidazo[1,2-b]pyridazin-6-yl]amino]tetrahydropyran-2-yl]methanol (compound 47)

47

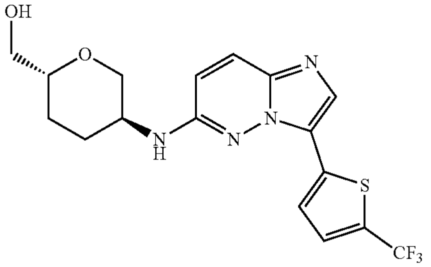

Referring to the procedures in step (1) of Example 7, [(2R,5S)-5-aminotetrahydropyran-2-yl]methanol hydrochloride (Example 14, 30.00 mg, 228.71 μmol) and 6-chloro-3-[5-(trifluoromethyl)-2-thienyl]imidazo[1,2-b]pyridazine (76.40 mg, 251.58 μmol) were used as starting materials to give [(2R,5S)-5[[3-[5-(trifluoromethyl)-2-thienyl]imidazo[1,2-b]pyridazin-6-yl]amino]tetrahydropyran-2-yl]methanol (0.006 g, yield: 6.58%) as a yellow solid. MS (ESI): m/z 399.0 $[M+H]^+$. $^1H$ NMR (400 MHz, $CD_3OD$) δ 8.00 (s, 1H), 7.71 (d, J=9.8 Hz, 2H), 7.58 (d, J=3.9 Hz, 1H), 6.76 (d, J=9.8 Hz, 1H), 4.35 (dd, J=2.3, 10.7 Hz, 1H), 4.08 (d, J=11.2 Hz, 1H), 3.62-3.54 (m, 2H), 3.50 (brs, 1H), 3.29-3.23 (m, 1H), 2.44 (brs, 1H), 1.86 (d, J=9.8 Hz, 1H), 1.62-1.49 (m, 2H).

EXAMPLE 26

N-(7-azas piro [3.5]nonan-2-ylmethyl)-3-[3-(trifluoromethyl)phenyl]imidazo[1,2-b]pyridazin-6-amine (compound 15)

15

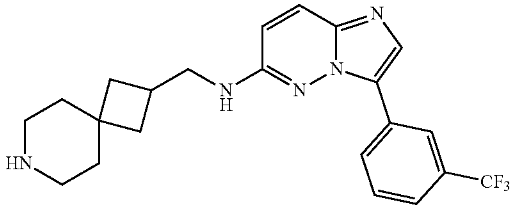

(1) Tert-butyl 2-[[[3-[3-(trifluoromethyl)phenyl]imidazo[1,2-b]pyridazin-6-yl]amino]methyl]-7-azaspiro[3.5]nonane-7-carboxylate Referring to the procedures in step (1) of Example 7, 6-chloro-3-[3-(trifluoromethyl)phenyl]imidazo[1,2-b]pyridazine (0.1 g, 335.95 μmol) and tert-butyl 2-(aminomethyl)-7-azaspiro[3.5]nonane-7-carboxylate (111.09 mg, 436.74 μmol) were used as starting materials to give tert-butyl 2-[[[3-[3-(trifluoromethyl)phenyl]imidazo[1,2-b]pyridazin-6-yl]amino]methyl]-7-azaspiro[3.5]nonane-7-carboxylate (90 mg, crude product) as a yellow oil.

(2) N-(7-azaspiro[3.5]nonan-2-ylmethyl)-3-[3-(trifluoromethyl)phenyl]imidazo[1,2-b]pyridazin-6-amine A solution of tert-butyl 2-[[[3-[3-(trifluoromethyl)phenyl]imidazo[1,2-b]pyridazin-6-yl]amino]methyl]7-azaspiro[3.5]nonane-7-carboxylate (90 mg, 174.56 μmol) in hydrochloric acid/methanol (4 M, 900.00 μL) was stirred at 20° C. for 2 h. After LCMS showed that the starting materials were consumed completely and a product was detected, the reaction solution was concentrated to give a crude product. The resulting crude product was dissolved with methanol, and then water was added. The mixed solution was adjusted to pH>7 with aqueous ammonia. The resulting solution was directly purified by Prep-HPLC to give N-(7-azaspiro[3.5]nonan-2-ylmethyl)-3-[3-(trifluoromethyl)phenyl]imidazo[1,2-b]pyridazin-6-amine (12 mg, yield: 16.55%) as a white solid. MS (ESI): m/z 416.1 $[M+H]^+$. $^1H$ NMR (400 MHz, $CD_3OD$) δ 8.86 (s, 1H), 8.19 (d, J=7.2 Hz, 1H), 7.88 (s, 1H), 7.63-7.57 (m, 3H), 6.72 (d, J=9.5 Hz, 1H), 3.40 (d, J=7.5 Hz, 2H), 2.81-2.76 (m, 2H), 2.72-2.62 (m, 3H), 2.04-1.98 (m, 2H), 1.66-1.61 (m, 2H), 1.59-1.52 (m, 4H).

EXAMPLE 27

2-[(1r,4r)-4-[(3-thiazol-2-ylimidazo[1,2-b]pyridazin-6-yl)amino]cyclohexyl]propan-2-ol (compound 17)

17

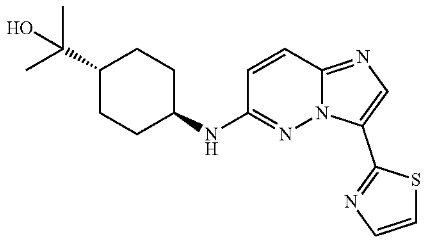

(1) 2-(6-chloroimidazo[1,2-b]pyridazin-3-yl)thiazole

Bis(triphenylphosphine)palladium(II) dichloride (17.58 mg, 25.05 μmol) was added to a solution of 6-chloro-3-iodo-imidazo[1,2-b]pyridazine (0.35 g, 1.25 mmol) and tributyl (thiazol-2-yl)stannane (468.61 mg, 1.25 mmol) in N,N-dimethylformamide (3.5 mL) under nitrogen atmosphere at 25° C. After the addition, the reaction solution was stirred at 110° C. for 6 h. After LCMS showed the starting materials were consumed completely and a product was produced, the reaction solution was poured into 10 mL of water. The mixed solution was extracted with ethyl acetate. The organic phases were combined, washed with saturated brine, dried over anhydrous sodium sulfate, filtered, and concentrated under reduced pressure to give 2-(6-chloroimidazo[1,2-b]pyridazin-3-yl)thiazole (0.22 g, crude product) as a white solid.

(2) 2-[4-[(3-thiazol-2-ylimidazo[1,2-b]pyridazin-6-yl)amino]cyclohexyl]propan-2-ol Referring to the procedures in step (1) of Example 7, 2-((1r,4r)-4-aminocyclohexyl)propan-2-ol (132.88 mg, 845.02 μmol) and 2-(6-chloroimidazo[1,2-b]pyridazin-3-yl)thiazole (200 mg, 845.02 μmol) were used as starting materials to give 2-[(1r,4r)-4-[(3-thiazol-2-ylimidazo[1,2-b]pyridazin-6-yl)amino]cyclohexyl]propan-2-ol (7.5 mg, yield: 2.48%) as a light yellow solid. MS (ESI): m/z 358.2 $[M+H]^+$. $^1H$ NMR (400 MHz, DMSO-$d_6$) δ 8.06 (s, 1H), 7.96 (brs, 1H), 7.87-7.80 (m, 2H), 7.24 (d, J=6.4 Hz, 1H), 6.78 (d, J=9.3 Hz, 1H), 4.10 (s, 1H), 3.70 (brs, 1H), 2.31 (brs, 2H), 1.90 (brs, 2H), 1.23 (d, J=8.4 Hz, 5H), 1.10 (s, 6H).

EXAMPLE 28

[(2S,5R)-5-[[3-[3-(trifluoromethyl)phenyl]imidazo[1,2-b]pyridazin-6-yl]amino]tetrahydropyran-2-yl]methanol (compound 22)

22

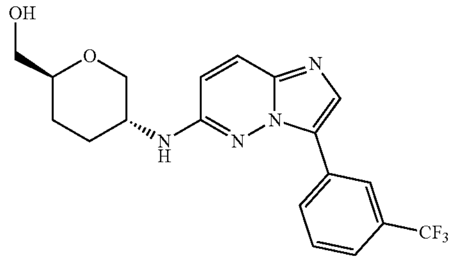

(1) [(2S ,5R)-5 -aminotetrahydropyran-2-yl] methanol hydrochloride

A solution of tert-butyl N-[(3R,6S)-6-(hydroxymethyl)tetrahydropyran-3-yl]carbamate (150 mg, 648.54 μmol) in hydrochloric acid/methanol (4 M, 1.50 mL) was stirred at 20° C. for 1 h. After TLC showed that the starting materials were consumed completely, the reaction solution was concentrated under reduced pressure to give [(2S,5R)-5-amino-tetrahydropyran-2-yl]methanol hydrochloride (85 mg, crude product) as a white solid.

(2) 2-[4-[(3-thiazol-2-ylimidazo[1,2-b]pyridazin-6-yl)amino]cyclohexyl]propan-2-ol Referring to the procedures in step (1) of Example 7, [(2S,5R)-5-aminotetrahydropyran-2-yl]methanol hydrochloride (85 mg, 507.06 μmol) and 6-chloro-3-[3-(trifluoromethyl)phenyl]imidazo[1,2-b]pyridazine (166.03 mg, 557.76 μmol) were used as starting materials to give [(2S,5R)-5-[[3-[3-(trifluoromethyl)phenyl]imidazo[1,2-b]pyridazin-6-yl]amino]tetrahydropyran-2-yl]methanol (9.4 mg, yield: 4.72%) as a white solid product. MS (ESI): m/z 393.2 $[M+H]^+$. $^1H$ NMR (400 MHz, DMSO-$d_6$) δ 8.79 (s, 1H), 8.32 (d, J=7.2 Hz, 1H), 8.06 (s, 1H), 7.80 (d, J=9.7 Hz, 1H), 7.72-7.64 (m, 2H), 7.05 (d, J=7.5 Hz, 1H), 6.72 (d, J=9.7 Hz, 1H), 4.65 (t, J=5.7 Hz, 1H), 4.11-4.05 (m, 1H), 3.88-3.77 (m, 1H), 3.45-3.38 (m, 1H), 3.32-3.27 (m, 2H), 3.11 (t, J=10.5 Hz, 1H), 2.24 (d, J=11.8 Hz, 1H), 1.78 (d, J=12.2 Hz, 1H), 1.51-1.38 (m, 1H), 1.36-1.23 (m, 1H).

EXAMPLE 29

2-((1r,4r)-4-((3-(3-(furan-2-yl)phenyl)imidazo[1,2-b]pyridazin-6-yl)amino)cyclohexyl)propan-2-ol (compound 48)

48

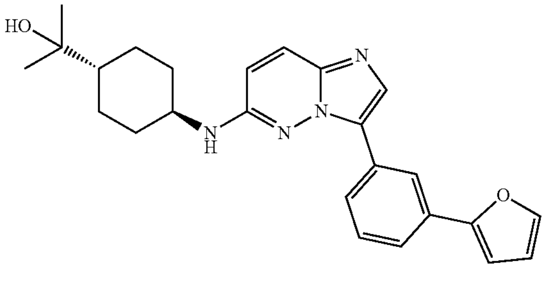

(1) 2-(3-bromophenyl)furan 1-bromo-3-iodobenzene (500 mg, 1.77 mmol) was dissolved in dioxane/water (10 mL/1 mL), and furan-2-boronic acid (237 mg, 2.12 mmol) was added, followed by the addition of potassium carbonate (561 mg, 5.31 mmol) and $PdCl_2$(dppf) (102 mg, 0.089 mmol). The reaction system was stirred at 90° C. for reaction overnight. The reaction solution was directly filtered, concentrated under reduced pressure, and purified by reverse phase column chromatography to give 2-(3-bromophenyl)furan (310 mg, yield: 79%) as a colorless liquid.

(2) 2-(3-(furan-2-yl)phenyl)-4,4,5,5-tetramethyl-1,3,2-dioxaborolane 2-(3-bromophenyl)furan (200 mg, 0.89 mmol) was dissolved in a dioxane solution (10 mL), and then bis(pinacolato)diboron (227 mg, 0.89 mmol), potassium acetate (262 mg, 2.67 mmol), and [1,1'-bis(diphenylphosphino)ferrocene]dichloropalladium(II) (33 mg, 0.05 mmol) were added thereto under nitrogen atmosphere. The mixture system was heated to 90° C. under nitrogen atmosphere and stirred for reaction overnight. The reaction solution was directly used in the next step.

(3) 6-chloro-3-(3-(furan-2-yl)phenyl)imidazo[1,2-b]pyridazine 3-bromo-6-chloroimidazo[1,2-b]pyridazine (206 mg, 0.89 mmol), [1,1'-bis(diphenylphosphino)ferrocene]dichloropalladium(II) (33 mg, 0.045 mmol), and water (1 mL) were added to a solution of 2-(3-(furan-2-yl)phenyl)-4,4,5,5-tetramethyl-1,3,2-dioxaborolane in dioxane (10 mL). The mixed solution was heated to 90° C. under nitrogen atmosphere and stirred overnight. After the reaction was completed as monitored by LCMS, the reaction system was concentrated and then purified by reverse phase column chromatography to give the target product 6-chloro-3-(3-(furan-2-yl)phenyl)imidazo[1,2-b]pyridazine (100 mg, yield: 38%) as a white solid. MS (ESI): m/z 295.9 $[M+H]^+$.

(4) 2-((1r,4r)-4-((3-(3-(furan-2-yl)phenyl)imidazo[1,2-b]pyridazin-6-yl)amino)cyclohexyl)propan-2-ol 6-chloro-3-(3-(furan-2-yl)phenyl)imidazo[1,2-b]pyridazine (100 mg, 0.34 mmol), 2((1r,4r)-4-aminocyclohexyl)propanol (86 mg, 0.68 mmol), and sodium tert-butoxide (98 mg, 1.02 mmol) were dispersed in toluene (5 mL), followed by the addition of BINAP (15 mg, 0.023 mmol) and $Pd_2(dba)_3$ (16 mg, 0.017 mmol). The reaction system was heated to 90° C. under nitrogen atmosphere and stirred for reaction overnight. The reaction solution was concentrated by rotary evaporation, and water (10 mL) was added to the reaction system. The mixed solution was extracted with ethyl acetate (20 mL×2), followed by liquid separation. The organic phase was dried over anhydrous sodium sulfate, filtered, concentrated under reduced pressure, and purified by Prep-HPLC to give 2-((1r,4r)-4-((3-(3-(furan-2-yl)phenyl)imidazo[1,2-b]pyridazin-6-yl)amino)cyclohexyl)propan-2-ol (7.8 mg, yield: 5%) as a white solid. MS (ESI): m/z 417.3 $[M+H]^+$. $^1H$ NMR (400 MHz, DMSO-$d_6$) 8.63 (t, J=1.6 Hz, 1H), 7.97-7.91 (m, 2H), 7.78-7.77 (m, 1H), 7.74 (d, J=10.8 Hz, 1H), 7.68-7.60 (m, 1H), 7.49 (t, J=7.6 Hz, 1H), 6.99-6.95 (m, 1H), 6.92 (d, J=6.8 Hz, 1H), 6.68 (d, J=9.6 Hz, 1H), 6.59 (q, J=1.6 Hz, 1H), 4.02 (s, 1H), 3.65-3.58 (m, 1H), 2.21 (d, J=6.0 Hz, 2H), 1.83 (d, J=11.6 Hz, 2H), 1.23 -1.00 (m, 11H).

EXAMPLE 30

2-((1r,4r)-4-((4-((3-(5-methyl-1,3,4-oxadiazol-2-yl) phenyl)imidazo[1,2-b] pyridazin-6-yl)amino)cyclohexyl)propan-2-ol (compound 49)

49

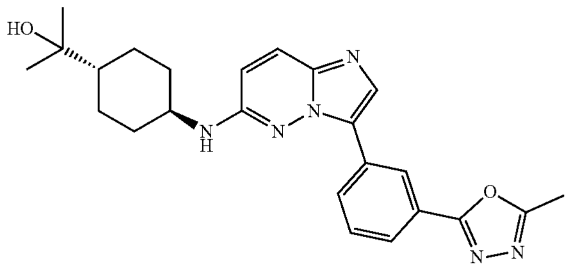

(1) 2-methyl-5-(3-(4,4,5,5-tetramethyl-1,3,2-dioxabenzaldehyde-2-yl)phenyl)-1,3,4-oxadiazole 2-(3-bromophenyl)-5-methyl-1,3,4-oxadiazole (400.0 mg, 1.68 mmol), bis (pinacolato)diboron (414.2 mg, 1.68 mmol), potassium acetate (328.3 mg, 3.36 mol), and [1,1'-bis(diphenylphosphino)ferrocene]dichloropalladium(II) (122.0 mg, 0.17 mmol) were added to a reaction flask, followed by the addition of dioxane (8 mL). The reaction system was heated to 90° C. under nitrogen atmosphere and stirred overnight. The reaction solution was concentrated by rotary evaporation to directly give a crude product 2-methyl-5-(3-(4,4,5,5-tetramethyl-1,3,2-dioxabenzaldehyde-2-yl)phenyl)-1,3,4-oxadiazole (480 mg, yield: 99%). MS (ESI): m/z 287.1 $[M+H]^+$.

(2) 2-(3-(6-chloroimidazo [1,2-b] pyridazin-3-yl)phenyl)-5-methyl-1,3,4-oxadiazole 2-methyl-5-(3-(4,4,5,5-tetramethyl-1,3,2-dioxabenzaldehyde-2-yl)phenyl)-1,3,4-oxadiazole (480 mg, 1.68 mmol), 3-bromo-6-chloroimidazo[1,2-b] pyridazine (389.0 mg, 1.68 mmol), tetrakis (triphenylphosphine)palladium(0) (195.6 mg, 0.17 mmol), and potassium carbonate (460.0 mg, 3.7 mmol) were dissolved in dioxane/water (8 mL/2 mL). The reaction system was heated to 90° C. under nitrogen atmosphere and stirred overnight. The reaction solution was concentrated by rotary evaporation and purified by forward column chromatography (PE/EA=1/1) to give 2-(3-(6-chloroimidazo[1,2-b] pyridazin-3-yl)phenyl)-5-methyl-1,3,4-oxadiazole (110 mg, yield: 21%) as a yellow solid. MS (ESI): m/z 311.9 $[M+H]^+$.

(3) 2-((1r,4r)-4-((3-(3-(5-methyl-1,3,4-oxadiazol-2-yl)phenyl)imidazo[1,2-b]pyridazin-6-yl)amino)cyclohexyl)propan- 2-ol 2-(3-(6-chloroimidazo[1,2-b]pyridazin-3-yl)phenyl)-5-methyl-1,3,4-oxadiazole (110 mg, 0.19 mmol), 2-((1r,4r)-4-aminocyclohexyl)propan-2-ol (30.3 mg, 0.19 mmol), tris(dibenzylideneacetone)dipalladium(0) (17.3 mg, 0.02 mmol), sodium tert-butoxide (55.6 mg, 0.58 mmol), and 4,5-dis(diphenylphosphino)-9,9-dimethylxanthene (22.0 mg, 0.04 mmol) were dissolved in toluene (5 mL). The reaction system was stirred at 110° C. for reaction overnight. The reaction solution was concentrated by rotary evaporation and purified by Pre-HPLC to give 2-((1r,4-((3-(3-(5-methyl-1,3,4-oxadiazol-2- yl)phenyl)imidazo[1,2-b] pyridazin-6-yl)amino)cyclohexyl)propan-2-ol (5.2 mg, yield: 6.2%) as a white solid. MS (ESI): m/z 433.1 $[M+H]^+$. $^1H$ NMR (400 MHz, DMSO-$d_6$) δ 8.89 (s, 1H), 8.42 (s, 1H), 8.23 (d, J=8.4 Hz, 1H), 8.02-7.98 (m, 2H), 7.74 (t, J=8.0 Hz, 1H), 7.55 (d, J=6.8 Hz, 1H), 7.09 (d, J=10.0 Hz, 1H), 3.61-3.54 (m, 1H), 2.60 (s, 3H), 2.18 (d, J=10.0 Hz, 2H), 1.79 (d, J=12.0 Hz, 2H), 1.22-1.13 (m, 3H), 1.05 (d, J=10.8 Hz, 2H), 0.99 (s, 6H).

EXAMPLE 31

3-(3-(dimethylamino)phenyl)-N-((1-methylpiperidin-4-yl)methyl)imidazo[1,2-b]pyridazin-6-amine (compound 50)

50

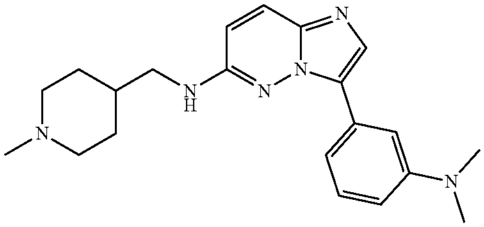

(1) 3-(6-chloroimidazo[1,2-b]pyridazin-3-yl)-N,N-dimethylaniline

Referring to the procedures in step (2) of Example 30, 3-bromo-6-chloroimidazo[1,2-b]pyridazine (100 mg, 0.434 mmol) and (3-(dimethylamino)phenyl)boronic acid (86 mg, 0.521 mmol) were used as starting materials to give 3-(6-chloroimidazo[1,2-b]pyridazin-3-yl)-N,N-dimethylaniline (64 mg, yield: 50.8%) as a white solid.

(2) 3-(3-(dimethylamino)phenyl)-N-((1-methylpiperidin-4-yl)methyl)imidazo[1,2-b]pyridazin-6-amine Referring to the procedures in step (3) of Example 30, 3-(6-chloroimidazo[1,2-b]pyridazin-3-yl)-N,N-dimethylaniline (142 mg, 0.522 mmol) and (1-methylpiperidin-4-yl) methylamine (74 mg, 0.574 mmol) were used as starting materials to give 3-(3-(dimethylamino)phenyl)-N-((1-methylpiperidin-4-yl)methyl)imidazo[1,2-b]pyridazin-6-amine (7.2 mg, yield: 3.9%) as a white solid. MS (ESI): m/z 365.4 $[M+H]^+$. $^1H$ NMR (400 MHz, DMSO-$d_6$) δ 8.26 (s, 1H), 8.34-8.30 (m, 2H), 7.97-7.95 (d, J=9.6 Hz, 1H), 7.64-7.61 (m, 2H), 7.39-7.37 (m, 1H), 7.34-7.30 (m, 1H), 7.05-7.02 (m, 1H), 6.80-6.78 (m, 1H), 3.46-3.43 (m, 2H), 3.25-3.22 (m, 2H), 2.93 (s, 6H), 2.90-2.88 (m, 2H), 2.70-2.66 (d, J=4.8 Hz, 3H), 2.32-1.72 (m, 2H), 1.40-1.37 (m, 2H).

EXAMPLE 32

2-[(1r,4r)-4-[[3-(3-methylsulfonylphenyl)imidazo[1,2-b]pyridazin-6-yl]amino]cyclohexyl]propan-2-ol (compound 51)

51

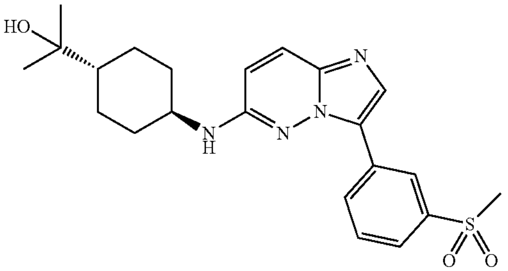

(1) 6-chloro-3-(3-methylsulfonylphenyl)imidazo[1,2-b]pyridazine

Referring to the procedures in step (3) of Example 29, 6-chloro-3-iodo-imidazo[1,2-b]pyridazine (200 mg, 715.65 μmol) and (3-methylsulfonylphenyl)boronic acid (171.77 mg, 858.78 μmol) were used as starting materials to give 6-chloro-3-(3-methylsulfonylphenyl)imidazo[1,2-b]pyridazine (120 mg, yield: 54.48%) as a yellow solid. MS (ESI): m/z 307.9 $[M+H]^+$.

(2) 2-[(1r,4r)-4-[[3-(3 -methylsulfonylphenyl)imidazo[1,2-b] pyridazin-6-yl]amino]cyclohexyl]propan-2-ol Referring to the procedures in step (4) of Example 29, 6-chloro-3-(3-methylsulfonylphenyl)imidazo[1,2-b]pyridazine (60 mg, 194.96 μmol) and 2-((1r,4r)-4-aminocyclohexyl)propan-2-ol (55.18 mg, 350.93 μmol) were used as starting materials to give 2-[(1r,4r)-4-[[3-(3 -methylsulfonylphenyl)imidazo[1,2-b]pyridazin-6-yl]amino]cyclohexyl]propan-2-ol (8.5 mg, yield: 10.17%) as a white solid. MS (ESI): m/z 429.1 $[M+H]^+$. $^1$H NMR (400 MHz, DMSO-$d_6$) δ 8.98 (brs, 1H), 8.33-8.46 (m, 1H), 8.05 (d, J=3.06 Hz, 1H), 7.66-7.93 (m, 3H), 6.99 (d, J=4.77 Hz, 1H), 6.72 (dd, J=9.48, 3.12 Hz, 1H), 4.03 (d, J=2.93 Hz, 1H), 3.65-3.75 (m, 1H), 3.24 (d, J=3.18 Hz, 3H), 2.15 (s, 2H), 1.82 (d, J=2.08 Hz, 2H), 1.16-1.32 (m, 4H), 1.07 (d, J=3.06 Hz, 6H).

EXAMPLE 33

2-[(1r,4r)-4-[[2-amino-3-[3-(trifluoromethyl)phenyl] imidazo[1,2-b] pyridazin-6-yl]amino]cyclohexyl] propan-2-ol (compound 52)

52

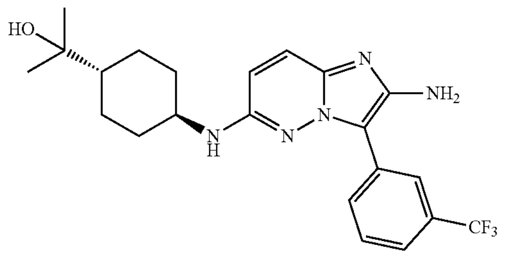

(1) 6-chloro-3-iodo-imidazo[1,2-b]pyridazin-2-amine

N-iodosuccinimide (1.60 g, 7.12 mmol) was added in portions to a solution of 6-chloroimidazo[1,2-b]pyridazin-2-amine (1 g, 5.93 mmol) in N,N-dimethylformamide (20 mL) at 0° C. After the addition, the reaction solution was naturally warmed to 25° C. and stirred at 25° C. for 2 h. The reaction was quenched by slowly pouring the reaction solution into ice water (50 mL). Then, the mixed solution was extracted with ethyl acetate (30 mL×3). The organic phases were combined and washed with saturated brine (30 mL). The organic phase was dried over anhydrous sodium sulfate, filtered, and concentrated to dryness to give a crude product. The resulting crude product was purified by column chromatography (petroleum ether/ethyl acetate=50/1-3/1) to give 6-chloro-3-iodo-imidazo[1,2-b]pyridazin-2-amine (0.6 g, crude product) as a brown solid, which was directly used in the next step.

(2) 6-chloro-3-[3-(trifluoromethyl)phenyl]imidazo[1,2-b]pyridazin-2-amine

[3-(trifluoromethyl)phenyl]boronic acid (212.84 mg, 1.12 mmol), potassium carbonate (281.60 mg, 2.04 mmol), and di-tert-butyl dicarbonate (244.58 mg, 1.12 mmol) were sequentially added to a solution of 6-chloro-3-iodo-imidazo[1,2-b]pyridazin-2-amine (0.3 g, 1.02 mmol) in dioxane (3 mL) at 25° C. The reaction system was purged 3 times with nitrogen. Then, [1,1'-bis(diphenylphosphino)ferrocene]dichloropalladium(II) (74.54 mg, 101.87 μmol) was added to the reaction solution under nitrogen atmosphere. After the addition, the system was heated to 80° C. and stirred at 80° C. for 12 h. The reaction solution was cooled to 25° C. and then filtered, and the filtrate was concentrated to dryness to give a crude product. The resulting crude product was purified by Prep-TLC (100% ethyl acetate) to give 6-chloro-3-[3-(trifluoromethyl)phenyl]imidazo[1,2-b]pyridazin-2-amine (0.1 g, crude product) as a yellow solid, which was directly used in the next step.

(3) 2-[(1r,4r)-4-[[2-amino-3-[3-(trifluoromethyl)phenyl] imidazo[1,2-b]pyridazin-6-yl]amino]cyclohexyl] propan-2-ol 2-((1r,40-4-aminocyclohexyl)propan-2-ol (30.18 mg, 191.89 μmol), N,N-diisopropylethylamine (51.67 mg, 399.77 μmol), and cesium fluoride (60.73 mg, 399.77 μmol) were sequentially added to a solution of 6-chloro-3-[3-(trifluoromethyl)phenyl]imidazo[1,2-b]pyridazin-2-amine (0.05 g, 159.91 μmol) in dimethyl sulfoxide (0.5 mL) at 20° C. The system was heated to 140° C. and stirred for 12 h. The reaction solution was cooled to 20° C. and then diluted with water (3 mL). The resulting solution was extracted with ethyl acetate (2 mL×3). The combined organic phases were washed with saturated brine (2 mL×2), dried over anhydrous sodium sulfate, filtered, and concentrated to give a crude product. The resulting crude product was purified by Prep-HPLC to give 2-[(1r,4r)-4-[[2-amino-3-[3 -(trifluoromethyl) phenyl]imidazo[1,2-b]pyridazin-6-yl]amino]cyclohexyl] propan-2-ol (0.01 g, yield: 12.78%) as a light yellow solid. MS (ESI): m/z 434.1 $[M+H]^+$. $^1$H NMR (400 MHz, $CD_3OD$) δ 8.27-8.48 (m, 1H), 7.95-8.13 (m, 1H), 7.60-7.82 (m, 3H), 6.84-6.94 (m, 1H), 3.53-3.69 (m, 1H), 2.18 (d, J=10.27 Hz, 2H), 1.86-2.04 (m, 2H), 1.18-1.41 (m, 5H), 1.14-1.17 (m, 6H).

EXAMPLE 34

4-[[3-[3-(trifluoromethyl)phenyl]imidazo[1,2-b] pyridazin-6-yl]amino]bicyclo[2.2.2]oct-1-ol (compound 36)

36

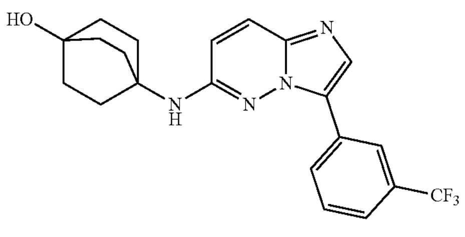

Referring to the procedures in step (1) of Example 7, 4-aminobicyclo[2.2.2]oct-1-ol hydrochloride (21 mg, 120.94 μmol) and 6-chloro-3-[3-(trifluoromethyl)phenyl] imidazo[1,2-b]pyridazine (30 mg, 100.79 μmol) were used as starting materials to give 4-[[3-[3-(trifluoromethyl)phenyl]imidazo[1,2-b]pyridazin-6-yl]amino]bicyclo[2.2.2]oct-1-ol (81 mg, yield: 33.3%) as a yellow solid. MS (ESI): m/z 403.2 $[M+H]^+$. $^1$H NMR (400 MHz, DMSO-$d_6$) δ 8.59 (s, 1H), 8.33-8.24 (m, 1H), 8.05-7.95 (m, 1H), 7.77-7.66 (m, 3H), 6.78-6.71 (m, 1H), 6.68-6.59 (m, 1H), 4.34 (s, 1H), 2.12-2.03 (m, 6H), 1.71-1.62 (m, 6H).

EXAMPLE 35

6-(((1r,4r)-4-(2-hydroxypropan-2-yl)cyclohexyl) amino)-3-(3-(trifluoromethyl)phenyl)imidazo[1,2-b] pyridazine-2-carbonitrile (compound 43)

43

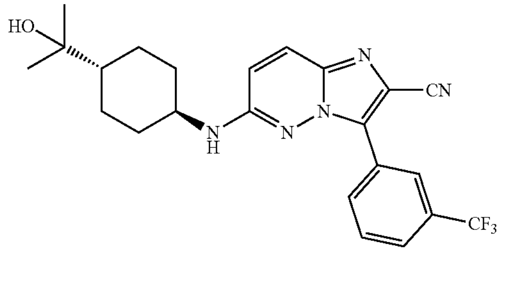

(1) 3-bromo-6-chloroimidazo[1,2-b]pyridazine-2-carboxylic acid

Ethyl 3-bromo-6-chloroimidazo[1,2-b]pyridazine-2-carboxylate (400 mg, 1.32 mmol) was dissolved in tetrahydrofuran/water (8 mL, v/v=3/1), followed by the addition of NaOH (1.81 g, 6.62 mmol). The reaction system was stirred at 25° C. for 2 h. The reaction solution was adjusted to pH 6 with dilute hydrochloric acid and concentrated by rotary evaporation. The resulting solid was added to methanol (5 mL). The mixture was stirred and filtered. The filtrate was concentrated by rotary evaporation to give 3-bromo-6-chloroimidazo[1,2-b]pyridazine-2-carboxylic acid (345 mg, yield: 95%) as a white solid, which was directly used in the next step. MS (ESI): m/z 275.9 $[M+H]^+$.

(2) 3-bromo-6-chloroimidazo[1,2-b]pyridazine-2-carboxamide 3-bromo-6-chloroimidazo[1,2-b]pyridazine-2-carboxylic acid (345 mg, 1.25 mmol) and 2-(7-azabenzotriazole)-N,N,N',N'-tetramethyluronium hexafluorophosphate (570 mg, 1.50 mmol) were dissolved in N,N-dimethylformamide (10 mL), followed by the addition of N,N-diisopropylethylamine (322 mg, 2.50 mmol) and ammonium chloride (100 mg, 1.88 mmol). The reaction system was stirred at room temperature for 1 h. Water (10 mL) was added to the reaction system. The mixed solution was extracted with ethyl acetate (10 mL×2), followed by liquid separation. The organic phase was washed with saturated brine (10 mL), dried over anhydrous sodium sulfate, filtered, concentrated under reduced pressure, and purified by reverse phase column chromatography (acetonitrile/water) to give 3-bromo-6-chloroimidazo [1,2-b]pyridazine-2-carboxamide (276 mg, yield: 80.9%) as a white solid. MS (ESI): m/z 274.9 $[M+H]^+$.

(3) 3-bromo-6-chloroimidazo[1,2-b]pyridazine-2-carbonitrile 3-bromo-6-chloroimidazo[1,2-b]pyridazine-2-carboxamide (276 mg, 1.01 mmol) was dissolved in dichloromethane (5 mL), followed by the addition of methyl N-(triethylammoniumsulfonyl)carbamate (1.24 g, 5.05 mmol). The reaction system was stirred at 25° C. for 16 h. The reaction solution was concentrated by rotary evaporation and purified by reverse phase column chromatography (acetonitrile/water) to give 3-bromo-6-chloroimidazo[1,2-b]pyridazine-2-carbonitrile (86 mg, yield: 33.4%) as a white solid. MS (ESI): m/z 256.9 $[M+H]^+$.

(4) 3 -bromo-64(1 r,40-4-(2-hydroxypropan-2-yl)cyclohexyl)aminoimidazo [1,2-b] pyridazine-2-carbonitrile 3-bromo-6-chloroimidazo[1,2-b]pyridazine-2-carbonitrile (86 mg, 0.33 mmol) was dissolved in dimethyl sulfoxide (5 mL), followed by the addition of 2-((1r, 4r)-4-aminocyclohexyl)propan-2-ol (58 mg, 0.37 mmol), triethylamine (68 mg, 0.62 mmol), and cesium fluoride (102 mg, 0.67 mmol). The reaction system was stirred at 110° C. for 16 h. Water (5 mL) was added to the reaction system. The mixed solution was extracted with ethyl acetate (10 mL×2), followed by liquid separation. The organic phase was washed with saturated brine (10 mL), dried over anhydrous sodium sulfate, filtered, and concentrated under reduced pressure to give 3-bromo-6-41r,40-4-(2-hydroxypropan-2-yl)cyclohexyl)aminoimidazo[1,2-b]pyridazine-2-carbonitrile (90 mg, yield: 70.8%) as a white solid. MS (ESI): m/z 378.1 $[M+H]^+$.

(5) 6-((1r,40-4-(2-hydroxypropan-2-yl)cyclohexy)amino)-3-(3-(trifluoromethyl)phenyl)imidazo [1,2-b]pyridazine-2-carbonitrile 3-bromo-6-((1r,4r)-4-(2-hydroxypropan-2-yl)cyclohexyl) aminoimidazo[1,2-b] pyridazine-2-carbonitrile (90 mg, 0.23 mmol) and (3-(trifluoromethyl)phenyl)boronic acid (49 mg, 0.26 mmol) were dissolved in 1,4-dioxane/water (4 mL, v/v=3/1), and then [1,1'-bis(diphenylphosphino)ferrocene] dichloropalladium(II) (17 mg, 0.02 mmol) and potassium carbonate (65 mg, 0.47 mmol) were added to the solution. The reaction solution was stirred overnight. After the solvent was removed, the reaction solution was directly purified by reverse column chromatography to give a crude product. The crude product was purified by Pre-HPLC to give 6-((1r,4r)-4-(2-hydroxypropan-2-yl)cyclohexyl)amino)-3-(3-(trifluoromethyl)phenyl)imidazo[1,2-b]pyridazine-2-carbonitrile (9.2 mg, yield: 8.7%) as a white solid. MS (ESI): m/z 444.2 $[M+H]^+$. $^1H$ NMR (400 MHz, DMSO-$d_6$) δ 8.55 (s, 1H), 8.22 (d, J=8.8 Hz, 1H), 7.89-7.84 (m, 3H), 7.44-7.42 (d, J=8.4 Hz, 1H), 6.95-6.91 (d, J=13.6 Hz, 1H), 4.07 (s, 1H), 3.50 (br, 1H), 2.11 (d, J=13.6 Hz, 2H), 1.85 (d, J=15.2 Hz, 2H), 1.24-1.10 (m, 5H), 1.05 (s, 6H). The other compounds were prepared according to the process routes described above.

Test Example 1: PIM1/2/3 Kinase Activity Test

1. Experimental Procedures

The efficacy of the compounds on the activity of PIM1/2/3 was tested by utilizing the Mobility shift assay method, with the specific procedures shown as follows: the test compounds were each dissolved in DMSO to be prepared into a 10 mM stock solution; for each of the test compounds, the stock solution was subjected to a 3-fold dilution from an initial concentration of 10 μM to obtain 10 concentrations.

The positive control drug TP-3654 was commercially available or prepared according to Example 31 of the patent WO2013013188.

PIM1, PIM2, and PIM3 (all three kinases are from Carna) were each prepared with 1× Kinase buffer into a kinase solution at a concentration that was 2.5 times the final concentration. 10 μL of kinase solution at a concentration that was 2.5 times the final concentration was added to each of the compound wells and the positive control well, and 10 μL of 1× Kinase buffer was added to the negative control well. The plate was centrifuged at 1000 rpm for 30 s, mixed well by shaking, and then incubated at room temperature for 10 min. A mixed solution of ATP and Kinase substrate 20 (from GL) at a concentration that was 25/15 times the final concentration was prepared with 1× Kinase buffer. The reaction was started by adding 15 μL of the mixed solution of ATP and Kinase substrate 20 at a concentration that was 25/15 times the final concentration. The 384-well plate was centrifuged at 1000 rpm for 30 s, mixed well by shaking, and then incubated at room temperature for 60 min. 30 μL of stop assay buffer was added to stop the kinase reaction. The plate was centrifuged at 1000 rpm for 30 s and mixed well by shaking. The conversion rates were read using Caliper EZ Reader.

2. Calculation for Results

The $IC_{50}$ values of the test compounds for kinase activity were obtained by adopting a fitted dose-response curve of analytic software GraphPad Prism 5. The results for the test compounds are shown in Table 1, where A+ indicates that the value is <2 nM, A indicates that the value is 2-10 nM, B indicates that the value is 10-100 nM, C indicates that the value is 100-1000 nM, D indicates that the value is 1000-10000 nM, and E indicates that the value is >10000 nM.

TABLE 1

Results for PIM1/2/3 kinase activity test

| Compound | PIM1 (IC50 nM) | PIM2 (IC50 nM) | PIM3 (IC50 nM) |
|---|---|---|---|
| 14 | B | C | C |
| 15 | B | D | C |
| 16 | A | C | B |
| 17 | C | C | C |
| 18 | B | C | C |
| 19 | A | C | B |
| 20 | A+ | C | B |
| 21 | C | D | D |
| 22 | B | D | D |
| 23 | C | E | D |
| 24 | C | D | C |
| 25 | C | E | D |
| 26 | B | D | C |
| 27 | B | C | C |
| 28 | A+ | C | B |
| 29 | A+ | B | B |
| 30 | B | E | D |
| 31 | A+ | C | B |
| 42 | C | E | D |
| 43 | C | E | E |
| 44 | C | E | E |
| 45 | B | D | D |
| 46 | A | D | C |
| 47 | B | E | D |
| 48 | B | E | C |
| 50 | C | E | D |
| 51 | C | D | E |
| TP-3654 | B | C | C |

Test Example 2: Cell Inhibitory Activity Test

The EPOR-JAK2-V617F gene was transferred into Ba/F3 wild-type cells by a retrovirus packaging system to obtain a stably transfected cell line Ba/F3-EPOR-JAK2-V617F, which was used for the cell inhibitory activity ICso test of the compounds (reference: *Blood.* 2010; 115(15): 3109-3117). The specific procedures were as follows:

Cells were seeded in a 96-well plate, treated with the test compounds from DMSO stock solutions (final concentration of DMSO is 0.2%), and cultured at 37° C. with 5% $CO_2$ for 72 h. Then, the cell proliferation inhibitory activity was assayed by the CTG (Cell-Titer Glo) method. For each of the test compounds, the stock solution was subjected to a 3-fold dilution from an initial concentration of 10 μM to obtain 9 concentrations. The dose-response relationship curve was fitted by using Graphpad 7.0 analysis software, and $IC_{50}$ values were obtained.

The results showed that the cell inhibitory activity of the most compounds are stronger than or equal to that of the PIM inhibitor TP-3654. The cell inhibitory activity $IC_{50}$ of some of the preferred compounds are significantly better (according to order-of-magnitude difference) than that of the PIM inhibitor TP-3654 (TP-3654 was prepared according to Example 31 of the patent WO2013013188). The results of part of the test compounds are shown in Table 2, where ++++ indicates that the value is 0-50 nM, +++ indicates that the value is 50-100 nM, ++ indicates that the value is 100-150 nM, and + indicates that the value is >150 nM.

TABLE 2

Results for data on cell inhibitory activity test

| Compound | Cell activity $IC_{50}$ (nM) Ba/F3-EPOR-JAK2-V617F (72 h CTG) |
|---|---|
| 16 | + |
| 20 | ++++ |
| 28 | +++ |
| 29 | ++++ |
| 31 | +++ |
| 46 | ++ |
| TP-3654 | + |

Test Example 3: Pharmacokinetic Test

1. Experimental Procedures

Experimental animals: BALB/c mice, female; weight: 19-25 g.

Preparation of test sample: the target compound was prepared into solutions at 0.4 mg/mL (for intravenous administration) and 5.0 mg/mL (for oral administration) for later use. Route of administration: oral administration/intravenous injection. Dosing volume and frequency: 5 mL/kg (intravenous injection) or 10 mL/kg (oral administration), single dose.

Sample collection: blood was collected at the following time points: 5 min, 15 min, 30 min, 1 hr, 2 hr, 4 hr, 8 hr, and 24 hr after the administration.

2. Sample Analysis and Results

Sample analysis: the collected samples were detected by using an LC-MS/MS method. The model of the instrument used was AB Sciex 5500.

Pharmacokinetic data analysis: the resulting plasma concentration data were fitted and calculated according to a non-compartmental model. Part of the results are summarized in Table 3.

TABLE 3

Results for pharmacokinetic test

| Dose (mg/kg) | Route of administration | Pharmacokinetic parameters (unit) | compound 29 | compound 20 | compound 46 | TP-3654 |
|---|---|---|---|---|---|---|
| 2 | Intravenous | CL (L/hr/kg) | 2.38 | 1.86 | 3.95 | 3.11 |
| | injection | Vss (L/kg) | 1.38 | 1.85 | 1.47 | 5.58 |
| | N = 3 | Terminal $t_{1/2}$ (hr) | 0.42 | 1.06 | 0.26 | 1.24 |
| | | $AUC_{last}$(hr × ng/mL) | 859 | 1086 | 523 | 652 |

TABLE 3-continued

| Results for pharmacokinetic test | | | | | | |
|---|---|---|---|---|---|---|
| Dose (mg/kg) | Route of administration | Pharmacokinetic parameters (unit) | compound 29 | compound 20 | compound 46 | TP-3654 |
| 50 | Oral administration N = 3 | $T_{max}$ (hr) | 0.33 | 1.33 | 0.50 | 1.00 |
| | | $C_{max}$ (ng/mL) | 6667 | 3980 | 10607 | 2550 |
| | | Terminal $t_{1/2}$ (hr) | 1.41 | 3.50 | 0.91 | 1.33 |
| | | $AUC_{last}$(hr × ng/mL) | 7651 | 18086 | 11771 | 6805 |
| | | F(%) | 35.7 | 66.6 | 89.9 | 42.3 |

Note:
1. The intravenous administration formulation is 10% DMSO/50% PEG400/40% (23% HPBCD).
2. The oral formulation are 10% Tween 20 + 90% (0.5% MC) (compound 29 or 46 or TP-3654) and 5% Tween 20 + 5% solutol + 90% (0.5% MC) (compound 20).

The test results showed that the compounds of the present invention had good pharmacokinetic characteristics, the exposure of the test compounds in animals through oral administration (Cmax and AUC) are higher than that of TP-3654, and the bioavailability of the test compounds are higher than that of TP-3654.

In addition, the compounds of the present invention were tested for toxic and side effects. The compounds were each administrated to nude mice once a day for 30 consecutive days. The result showed that the compounds had less toxic and side effects and were well tolerated in animals, with the highest dosage tested being 150 mg/kg/day.

Unless otherwise defined, all terms used herein have the meanings commonly understood by those skilled in the art.

The embodiments described in the present invention are for illustrative purposes only and are not intended to limit the scope of the present invention, and various other substitutions, alterations, and modifications may be made by those skilled in the art within the scope of the present invention. Therefore, the present invention is not limited to the embodiments described above, but is limited only by the claims.

The invention claimed is:

1. A compound having a structure represented by general formula (II):

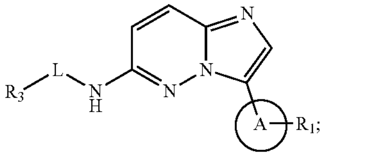

(II)

or a deuterated compound, a stereoisomer, or a pharmaceutically acceptable salt thereof;

wherein:

ring A and $R_1$ form the following structure:

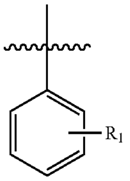

or

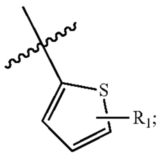

L is a chemical bond or methylene;

$R_1$ is hydrogen or trifluoromethyl, when ring A and $R_1$ form the following structure:

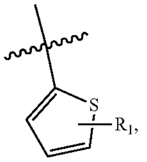

$R_3$ is selected from the group consisting of

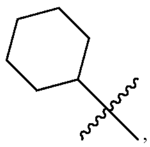

,

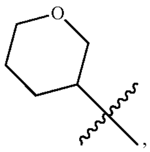

,

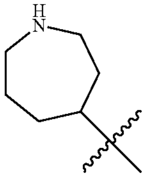

,

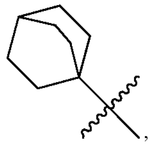

, and

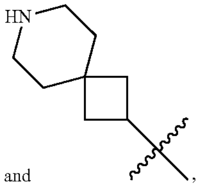

, the $R_3$ is optionally substituted with one $R^a$ at a substitution site of C or N;

when ring A and $R_1$ form the following structure:

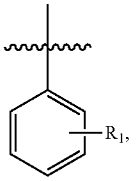

$R_3$ is

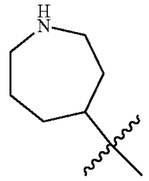

, or

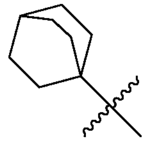

;

the $R_3$ is optionally substituted with one $R^a$ at a substitution site of C or N;

the $R^a$ is selected from the group consisting of hydrogen, halogen, hydroxyl, —$C_1$-$C_6$ alkyl, and —($C_1$-$C_6$ alkylene)—OH.

2. The compound, or the deuterated compound, the stereoisomer, or the pharmaceutically acceptable salt thereof according to claim 1, the compound has a structure represented by general formula (III-1)

(III-1)

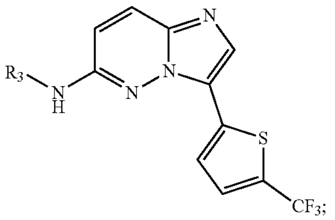

wherein:

$R_3$ is selected from

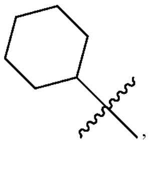

,

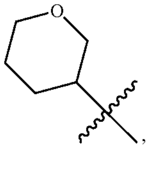

,

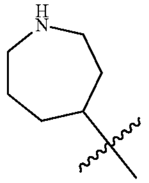

,

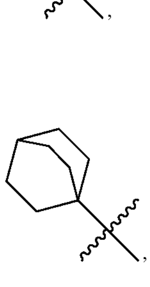

, and

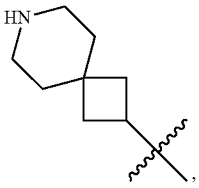

, and the $R_3$ is optionally substituted with one $R^a$ at a substitution site of C or N;

$R^a$ is selected from hydrogen, hydroxyl,-methylenehydroxyl, and —$C(CH_3)_2$—OH.

3. The compound, or the deuterated compound, the stereoisomer, or the pharmaceutically acceptable salt thereof according to claim 2, wherein $R_3$ is selected from:

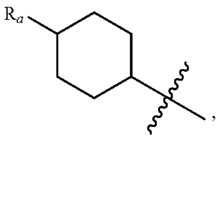

,

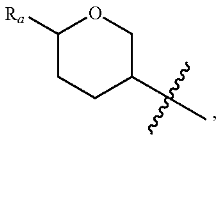

,

-continued

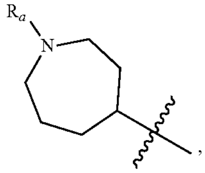

,

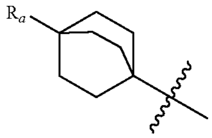

, and

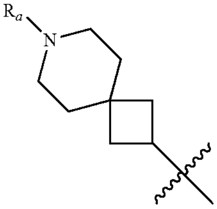

.

4. The compound, or the deuterated compound, the stereoisomer, or the pharmaceutically acceptable salt thereof according to claim 2, wherein $R_3$ is selected from:

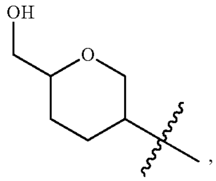

,

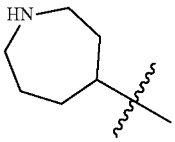

,

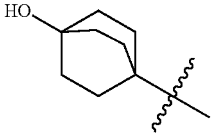

, and

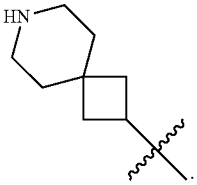

.

5. The compound, or the deuterated compound, the stereoisomer, or the pharmaceutically acceptable salt thereof according to claim 2, the compound has a structure represented by general formula (III-1):

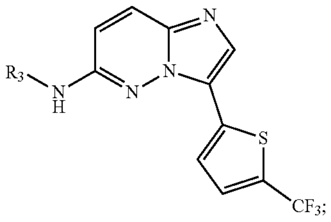

wherein $R_3$ is selected from

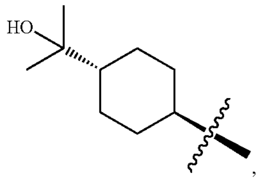,
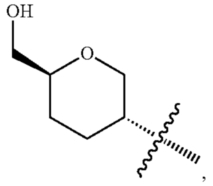,
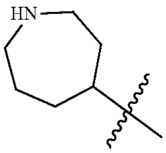,
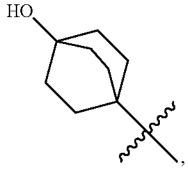, and
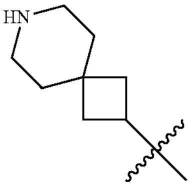;

6. The compound, or the deuterated compound, the stereoisomer, or the pharmaceutically acceptable salt thereof according to claim 1, the compound has a structure represented by general formula (III-2):

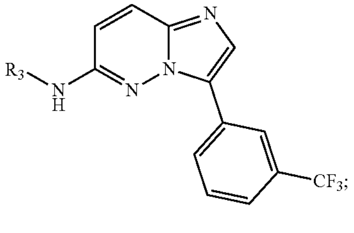

wherein $R_3$ is

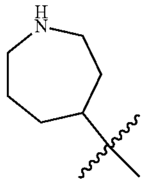
or,
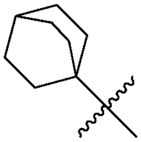, and the $R_3$ is optionally substituted with one $R^a$ at a substitution site of C or N; and $R^a$ is selected from hydrogen, hydroxyl,-methylenehydroxyl, and —$C(CH_3)_2$—OH.

7. The compound, or the deuterated compound, the stereoisomer, or the pharmaceutically acceptable salt thereof according to claim 1, the compound has a structure represented by general formula (IV-1) or (IV-2):

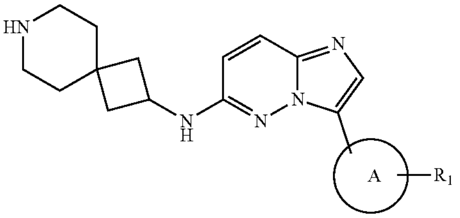

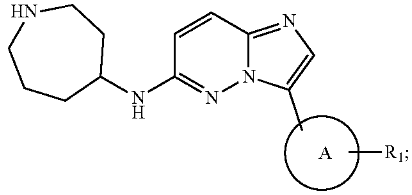

wherein:

ring A and R1 form the following structure:

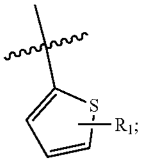

and $R_1$ is selected from hydrogen and trifluoromethyl.

8. The compound, or the deuterated compound, the stereoisomer, or the pharmaceutically acceptable salt thereof according to claim 7, wherein ring A forms the following structure

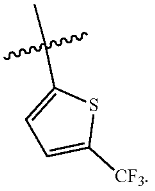 [SMILES: *c1ccc(C(F)(F)F)s1]

9. The compound, or the deuterated compound, the stereoisomer, or the pharmaceutically acceptable salt thereof according to claim 1, wherein the compound is selected from the following structures:

14

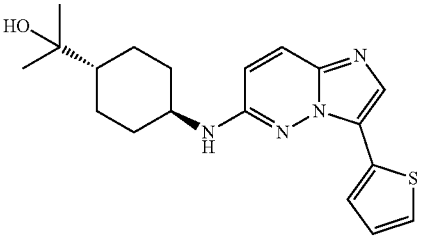

-continued

20

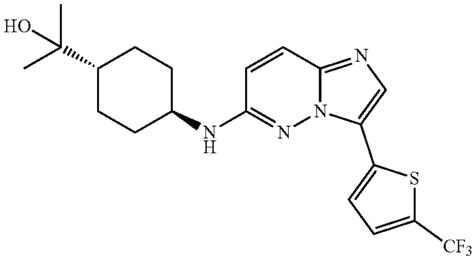

27

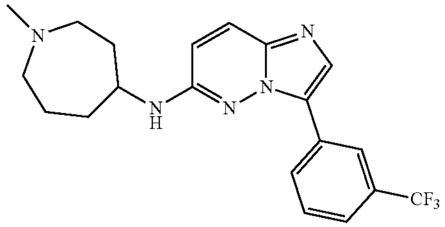

28

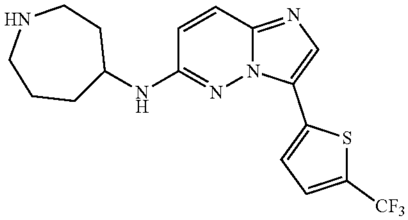

29

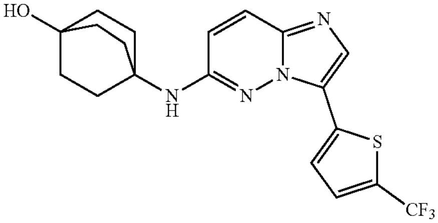

31

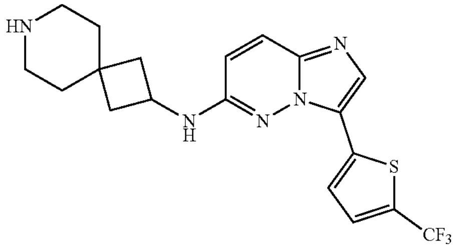

36

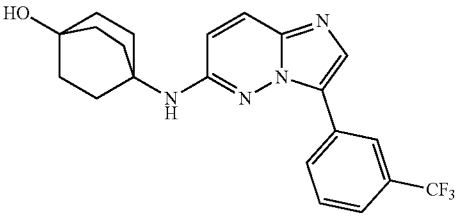

-continued

46

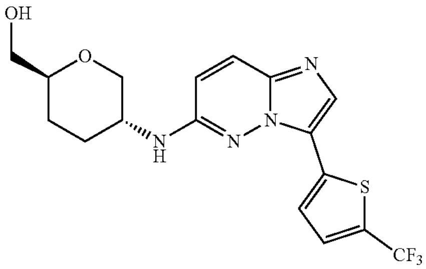

47

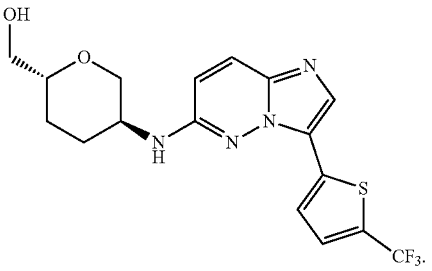

10. A pharmaceutical composition comprising the compound, or the deuterated compound, the stereoisomer, or the pharmaceutically acceptable salt thereof according to claim 1, and a pharmaceutically acceptable carrier therefor.

11. A method for treating and/or preventing a PIM-related disease, comprising administering a therapeutically effective amount of the compound, or the deuterated compound, the stereoisomer, or the pharmaceutically acceptable salt thereof according to claim 1 or a pharmaceutical composition comprising the compound, or the deuteride, the stereoisomer, or the pharmaceutically acceptable salt thereof according to claim 1 to a subject in need thereof.

12. The method according to claim 11, wherein the PIM-related disease comprises an autoimmune disease or a tumor.

13. The method according to claim 11, wherein the PIM-related disease comprises an inflammatory bowel disease, a hematological tumor, or a solid tumor.

14. The method according to claim 13, wherein the hematological tumor includes, but is not limited to, acute myeloid leukemia, myelofibrosis, or chronic lymphocytic leukemia; the solid tumor includes, but is not limited to, gastric cancer or prostate cancer.

15. The compound, or the deuterated compound, the stereoisomer, or the pharmaceutically acceptable salt thereof according to claim 3, wherein $R_3$ is selected from:

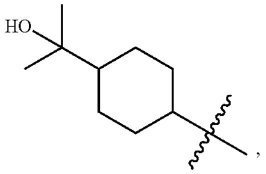 ,
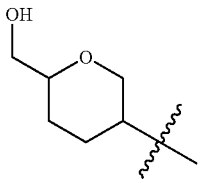 ,
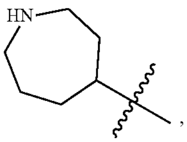 ,
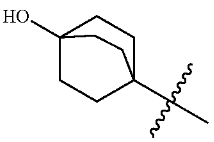 , and

-continued

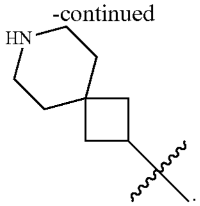

16. The compound, or the deuterated compound, the stereoisomer, or the pharmaceutically acceptable salt thereof according to claim 6, wherein $R_3$ is:

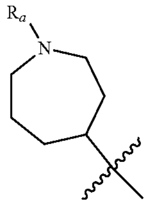
or,
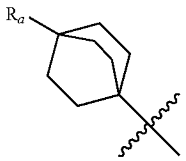
,

17. The compound, or the deuterated compound, the stereoisomer, or the pharmaceutically acceptable salt thereof according to claim 16, wherein $R_3$ is:

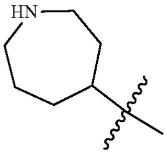
, or
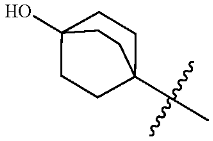
,

18. The compound, or the deuterated compound, the stereoisomer, or the pharmaceutically acceptable salt thereof according to claim 6, wherein $R_3$ is:

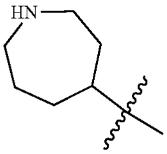
or
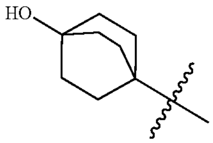
,

19. The compound, or the deuterated compound, the stereoisomer, or the pharmaceutically acceptable salt thereof according to claim 6, the compound has a structure represented by general formula (III-2):

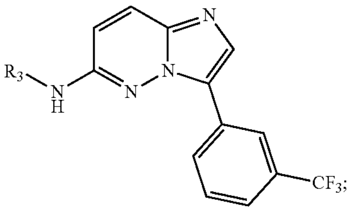

wherein $R_3$ is

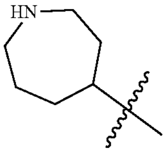 [SMILES: *C1CCCNCC1]

20. The compound, or the deuterated compound, the stereoisomer, or the pharmaceutically acceptable salt thereof according to claim 1, the compound has a structure represented by general formula (IV-2):

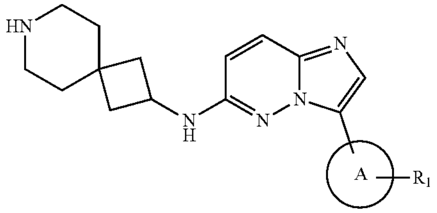

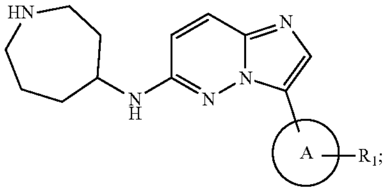

wherein:

ring A and R1 form the following structure:

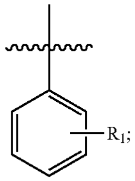

$R_1$ is selected from hydrogen and trifluoromethyl.

21. The compound, or the deuterated compound, the stereoisomer, or the pharmaceutically acceptable salt thereof according to claim 20, wherein ring A and $R_1$ form the following structure:

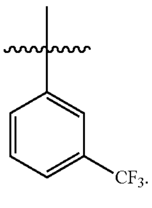 [SMILES: *c1cccc(C(F)(F)F)c1]

* * * * *